(12) United States Patent
Johns et al.

(10) Patent No.: US 10,538,495 B2
(45) Date of Patent: Jan. 21, 2020

(54) MODULATORS OF INDOLEAMINE 2,3-DIOXYGENASE

(71) Applicant: GLAXOSMITHKLINE INTELLECTUAL PROPERTY DEVELOPMENT LIMITED, Brentford, Middlesex (GB)

(72) Inventors: Brian Alvin Johns, Research Triangle Park, NC (US); Wieslaw Mieczyslaw Kazmierski, Research Triangle Park, NC (US); Martha Alicia De La Rosa, Research Triangle Park, NC (US); Vicente Samano, Research Triangle Park, NC (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 16/094,910

(22) PCT Filed: May 11, 2017

(86) PCT No.: PCT/IB2017/052774
§ 371 (c)(1),
(2) Date: Oct. 19, 2018

(87) PCT Pub. No.: WO2017/195149
PCT Pub. Date: Nov. 16, 2017

(65) Prior Publication Data
US 2019/0119223 A1    Apr. 25, 2019

Related U.S. Application Data

(60) Provisional application No. 62/335,094, filed on May 12, 2016.

(51) Int. Cl.
| | | |
|---|---|---|
| C07D 257/04 | (2006.01) |
| C07D 403/12 | (2006.01) |
| C07F 9/6524 | (2006.01) |
| C07D 401/04 | (2006.01) |
| C07D 401/10 | (2006.01) |
| C07D 405/12 | (2006.01) |
| C07D 417/12 | (2006.01) |
| C07C 323/63 | (2006.01) |
| C07D 249/06 | (2006.01) |
| C07D 249/08 | (2006.01) |
| C07D 271/06 | (2006.01) |
| C07C 323/42 | (2006.01) |
| C07C 323/45 | (2006.01) |
| C07D 285/08 | (2006.01) |
| C07D 401/12 | (2006.01) |
| C07D 413/12 | (2006.01) |

(52) U.S. Cl.
CPC .......... *C07D 257/04* (2013.01); *C07C 323/42* (2013.01); *C07C 323/45* (2013.01); *C07C 323/63* (2013.01); *C07D 249/06* (2013.01); *C07D 249/08* (2013.01); *C07D 271/06* (2013.01); *C07D 285/08* (2013.01); *C07D 401/04* (2013.01); *C07D 401/10* (2013.01); *C07D 401/12* (2013.01); *C07D 403/12* (2013.01); *C07D 405/12* (2013.01); *C07D 413/12* (2013.01); *C07D 417/12* (2013.01); *C07F 9/6524* (2013.01)

(58) Field of Classification Search
CPC ............................ C07D 257/04; C07C 323/42
See application file for complete search history.

(56) References Cited

FOREIGN PATENT DOCUMENTS

| WO | WO 2014/150646 A1 | 9/2014 |
| WO | WO 2015/002918 A1 | 1/2015 |
| WO | WO 2015/031295 A1 | 3/2015 |

OTHER PUBLICATIONS

Database WPI, Week 197523, Thomson Scientific, London, GB; AN 1975-38406W. XP002771067, & JP S50 4070 A, Jan. 16, 1975 (Abstract).
Database WPI, Week 197452, Thomson Scientific, London, GB; AN 1974-89432V. XP002771068, & JP S49 80064 A, Aug. 2, 1974.
Patani, et al. "Bioisosterism: A Rational Approach in Drug Design", Chemical Reviews, 96(8): 3147-3176, Jan. 1, 1996.
F.D. King. "Bioisosteres, Conformational Restriction, and Pro-Drugs—Case History: An Example of Conformational Restriction Approach". King, F.D. (Ed.), Medicinal Chemistry: Principles and Practice, 206-225, Jan. 1, 1994.

*Primary Examiner* — Golam M Shameem
(74) *Attorney, Agent, or Firm* — Robert H. Brink; Kathryn A. Lutomski; Edward R. Gimmi

(57) ABSTRACT

Provided are IDO inhibitor compounds of Formula I and pharmaceutically acceptable salts thereof, their pharmaceutical compositions, their methods of preparation, and methods for their use in the prevention and/or treatment of diseases.

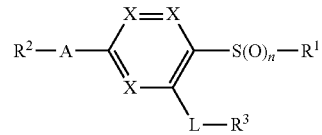

Formula I

2 Claims, No Drawings

MODULATORS OF INDOLEAMINE 2,3-DIOXYGENASE

This application is a § 371 of International Application No. PCT/IB2017/052774, filed 11 May 2017, which claims the benefit of U.S. Provisional Application No. 62/335,094, filed 12 May 2016.

FIELD OF THE INVENTION

Compounds, methods and pharmaceutical compositions for the prevention and/or treatment of HIV; including the prevention of the progression of AIDS and general immunosuppression, by administering certain indoleamine 2,3-dioxygenase compounds in therapeutically effective amounts are disclosed. Methods for preparing such compounds and methods of using the compounds and pharmaceutical compositions thereof are also disclosed.

BACKGROUND OF THE INVENTION

Indoleamine-2,3-dioxygenase 1 (IDO1) is a heme-containing enzyme that catalyzes the oxidation of the indole ring of tryptophan to produce N-formyl kynurenine, which is rapidly and constitutively converted to kynurenine (Kyn) and a series of downstream metabolites. IDO1 is the rate limiting step of this kynurenine pathway of tryptophan metabolism and expression of IDO1 is inducible in the context of inflammation. Stimuli that induce IDO1 include viral or bacterial products, or inflammatory cytokines associated with infection, tumors, or sterile tissue damage. Kyn and several downstream metabolites are immunosuppressive: Kyn is antiproliferative and proapoptotic to T cells and NK cells (Munn, Shafizadeh et al. 1999, Frumento, Rotondo et al. 2002) while metabolites such as 3-hydroxy anthranilic acid (3-HAA) or the 3-HAA oxidative dimerization product cinnabarinic acid (CA) inhibit phagocyte function (Sekkai, Guittet et al. 1997), and induce the differentiation of immunosuppressive regulatory T cells (Treg) while inhibiting the differentiation of gut-protective IL-17 or IL-22-producing CD4+ T cells (Th17 and Th22) (Favre, Mold et al. 2010). IDO1 induction, among other mechanisms, is likely important in limiting immunopathology during active immune responses, in promoting the resolution of immune responses, and in promoting fetal tolerance. However in chronic settings, such as cancer, or chronic viral or bacterial infection, IDO1 activity prevents clearance of tumor or pathogen and if activity is systemic, IDO1 activity may result in systemic immune dysfunction (Boasso and Shearer 2008, Li, Huang et al. 2012). In addition to these immunomodulatory effects, metabolites of IDO1 such as Kyn and quinolinic acid are also known to be neurotoxic and are observed to be elevated in several conditions of neurological dysfunction and depression. As such, IDO1 is a therapeutic target for inhibition in a broad array of indications, such as to promote tumor clearance, enable clearance of intractable viral or bacterial infections, decrease systemic immune dysfunction manifest as persistent inflammation during HIV infection or immunosuppression during sepsis, and prevent or reverse neurological conditions.

IDO1 and Persistent Inflammation in HIV Infection:

Despite the success of antiretroviral therapy (ART) in suppressing HIV replication and decreasing the incidence of AIDS-related conditions, HIV-infected patients on ART have a higher incidence of non-AIDS morbidities and mortality than their uninfected peers. These non-AIDS conditions include cancer, cardiovascular disease, osteoporosis, liver disease, kidney disease, frailty, and neurocognitive dysfunction (Deeks 2011). Several studies indicate that non-AIDS morbidity/mortality is associated with persistent inflammation, which remains elevated in HIV-infected patients on ART as compared to peers (Deeks 2011). As such, it is hypothesized that persistent inflammation and immune dysfunction despite virologic suppression with ART is a cause of these non-AIDS-defining events (NA-DEs).

HIV infects and kills CD4+ T cells, with particular preference for cells like those CD4+ T cells that reside in the lymphoid tissues of the mucosal surfaces (Mattapallil, Douek et al. 2005). The loss of these cells combined with the inflammatory response to infection result in a perturbed relationship between the host and all pathogens, including HIV itself, but extending to pre-existing or acquired viral infections, fungal infections, and resident bacteria in the skin and mucosal surfaces. This dysfunctional host:pathogen relationship results in the over-reaction of the host to what would typically be minor problems as well as permitting the outgrowth of pathogens among the microbiota. The dysfunctional host:pathogen interaction therefore results in increased inflammation, which in turn leads to deeper dysfunction, driving a vicious cycle. As inflammation is thought to drive non-AIDS morbidity/mortality, the mechanisms governing the altered host:pathogen interaction are therapeutic targets.

IDO1 expression and activity are increased during untreated and treated HIV infection as well as in primate models of SIV infection (Boasso, Vaccari et al. 2007, Favre, Lederer et al. 2009, Byakwaga, Boum et al. 2014, Hunt, Sinclair et al. 2014, Tenorio, Zheng et al. 2014). IDO1 activity, as indicated by the ratio of plasma levels of enzyme substrate and product (Kyn/Tryp or K:T ratio), is associated with other markers of inflammation and is one of the strongest predictors of non-AIDS morbidity/mortality (Byakwaga, Boum et al. 2014, Hunt, Sinclair et al. 2014, Tenorio, Zheng et al. 2014). In addition, features consistent with the expected impact of increased IDO1 activity on the immune system are major features of HIV and SIV induced immune dysfunction, such as decreased T cell proliferative response to antigen and imbalance of Treg:Th17 in systemic and intestinal compartments (Favre, Lederer et al. 2009, Favre, Mold et al. 2010). As such, we and others hypothesize that IDO1 plays a role in driving the vicious cycle of immune dysfunction and inflammation associated with non-AIDS morbidity/mortality. Thus, we propose that inhibiting IDO1 will reduce inflammation and decrease the risk of NADEs in ART-suppressed HIV-infected persons.

IDO1 and Oncology

IDO expression can be detected in a number of human cancers (for example; melanoma, pancreatic, ovarian, AML, CRC, prostate and endometrial) and correlates with poor prognosis (Munn 2011). Multiple immunosuppressive roles have been ascribed to the action of IDO, including the induction of Treg differentiation and hyper-activation, suppression of Teff immune response, and decreased DC function, all of which impair immune recognition and promote tumor growth (Munn 2011). IDO expression in human brain tumors is correlated with reduced survival. Orthotropic and transgenic glioma mouse models demonstrate a correlation between reduced IDO expression and reduced Treg infiltration and a increased long term survival (Wainwright, Balyasnikova et al. 2012). In human melanoma a high proportion of tumors (33 of 36 cases) displayed elevated IDO suggesting an important role in establishing an immunosuppressive tumor microenvironment (TME) characterized by the expansion, activation and recruitment of MDSCs in a Treg-dependent manner (Holmgaard, Zamarin et al. 2015). Additionally, host IDO expressing immune cells have been identified in the draining lymph nodes and in the tumors themselves (Mellor and Munn 2004). Hence, both tumor and host-derived IDO are believed to contribute to the immune suppressed state of the TME.

The inhibition of IDO was one of the first small molecule drug strategies proposed for re-establishment of an immunogenic response to cancer (Mellor and Munn 2004). The d-enantiomer of 1-methyl tryptophan (D-1MTor indoximod) was the first IDO inhibitor to enter clinical trials. While this compound clearly does inhibit the activity of IDO, it is a very weak inhibitor of the isolated enzyme and the in vivo mechanism(s) of action for this compound are still being elucidated. Investigators at Incyte optimized a hit compound obtained from a screening process into a potent and selective inhibitor with sufficient oral exposure to demonstrate a delay in tumor growth in a mouse melanoma model (Yue, Douty et al. 2009). Further development of this series led to INCB204360 which is a highly selective for inhibition of IDO-1 over IDO-2 and TDO in cell lines transiently transfected with either human or mouse enzymes (Liu, Shin et al. 2010). Similar potency was seen for cell lines and primary human tumors which endogenously express IDO1 (IC50s~3-20 nM). When tested in co-culture of DCs and naïve $CD4^+CD25^-$ T cells, INCB204360 blocked the conversion of these T cells into $CD4^+FoxP3^+$ Tregs. Finally, when tested in a syngeneic model (PAN02 pancreatic cells) in immunocompetent mice, orally dosed INCB204360 provided a significant dose-dependent inhibition of tumor growth, but was without effect against the same tumor implanted in immune-deficient mice. Additional studies by the same investigators have shown a correlation of the inhibition of IDO1 with the suppression of systemic kynurenine levels and inhibition of tumor growth in an additional syngeneic tumor model in immunocompetent mice. Based upon these preclinical studies, INCB24360 entered clinical trials for the treatment of metastatic melanoma (Beatty, O'Dwyer et al. 2013).

In light of the importance of the catabolism of tryptophan in the maintenance of immune suppression, it is not surprising that overexpression of a second tryptophan metabolizing enzyme, TDO2, by multiple solid tumors (for example, bladder and liver carcinomas, melanomas) has also been detected. A survey of 104 human cell lines revealed 20/104 with TDO expression, 17/104 with IDO1 and 16/104 expressing both (Pilotte, Larrieu et al. 2012). Similar to the inhibition of IDO1, the selective inhibition of TDO2 is effective in reversing immune resistance in tumors overexpressing TDO2 (Pilotte, Larrieu et al. 2012). These results support TDO2 inhibition and/or dual TDO2/IDO1 inhibition as a viable therapeutic strategy to improve immune function.

Multiple pre-clinical studies have demonstrated significant, even synergistic, value in combining IDO-1 inhibitors in combination with T cell checkpoint modulating mAbs to CTLA-4, PD-1, and GITR. In each case, both efficacy and related PD aspects of improved immune activity/function were observed in these studies across a variety of murine models (Balachandran, Cavnar et al. 2011, Holmgaard, Zamarin et al. 2013, M. Mautino 2014, Wainwright, Chang et al. 2014). The Incyte IDO1 inhibitor (INCB204360, epacadostat) has been clinically tested in combination with a CTLA4 blocker (ipilimumab), but it is unclear that an effective dose was achieved due to dose-limited adverse events seen with the combination. In contrast recently released data for an on-going trial combining epacadostat with Merck's PD-1 mAb (pembrolizumab) demonstrated improved tolerability of the combination allowing for higher doses of the IDO1 inhibitor. There have been several clinical responses across various tumor types which is encouraging. However, it is not yet known if this combination is an improvement over the single agent activity of pembrolizumab (Gangadhar, Hamid et al. 2015). Similarly, Roche/Genentech are advancing NGL919/GDC-0919 in combination with both mAbs for PD-L1 (MPDL3280A, Atezo) and OX-40 following the recent completion of a phase 1a safety and PK/PD study in patients with advanced tumors.

IDO1 and Chronic Infections

IDO1 activity generates kynurenine pathway metabolites such as Kyn and 3-HAA that impair at least T cell, NK cell, and macrophage activity (Munn, Shafizadeh et al. 1999, Frumento, Rotondo et al. 2002) (Sekkai, Guittet et al. 1997, Favre, Mold et al. 2010). Kyn levels or the Kyn/Tryp ratio are elevated in the setting of chronic HIV infection (Byakwaga, Boum et al. 2014, Hunt, Sinclair et al. 2014, Tenorio, Zheng et al. 2014), HBV infection (Chen, Li et al. 2009), HCV infection (Larrea, Riezu-Boj et al. 2007, Asghar, Ashiq et al. 2015), and TB infection (Suzuki, Suda et al. 2012) and are associated with antigen-specific T cell dysfunction (Boasso, Herbeuval et al. 2007, Boasso, Hardy et al. 2008, Loughman and Hunstad 2012, Ito, Ando et al. 2014, Lepiller, Soulier et al. 2015). As such, it is thought that in these cases of chronic infection, IDO1-mediated inhibition of the pathogen-specific T cell response plays a role in the persistence of infection, and that inhibition of IDO1 may have a benefit in promoting clearance and resolution of infection.

IDO1 and Sepsis

IDO1 expression and activity are observed to be elevated during sepsis and the degree of Kyn or Kyn/Tryp elevation corresponded to increased disease severity, including mortality (Tattevin, Monnier et al. 2010, Darcy, Davis et al. 2011). In animal models, blockade of IDO1 or IDO1 genetic knockouts protected mice from lethal doses of LPS or from mortality in the cecal ligation/puncture model (Jung, Lee et al. 2009, Hoshi, Osawa et al. 2014). Sepsis is characterized by an immunosuppressive phase in severe cases (Hotchkiss, Monneret et al. 2013), potentially indicating a role for IDO1 as a mediator of immune dysfunction, and indicating that pharmacologic inhibition of IDO1 may provide a clinical benefit in sepsis.

IDO1 and Neurological Disorders

In addition to immunologic settings, IDO1 activity is also linked to disease in neurological settings (reviewed in Lovelace Neuropharmacology 2016(Lovelace, Varney et al. 2016)). Kynurenine pathway metabolites such as 3-hydroxykynurenine and quinolinic acid are neurotoxic, but are balanced by alternative metabolites kynurenic acid or picolinic acid, which are neuroprotective. Neurodegenerative and psychiatric disorders in which kynurenine pathway metabolites have been demonstrated to be associated with disease include multiple sclerosis, motor neuron disorders such as amyotrophic lateral sclerosis, Huntington's disease, Parkinson's disease, Alzheimer's disease, major depressive disorder, schizophrenia, anorexia (Lovelace, Varney et al. 2016). Animal models of neurological disease have shown some impact of weak IDO1 inhibitors such as 1-methyltryptophan on disease, indicating that IDO1 inhibition may provide clinical benefit in prevention or treatment of neurological and psychiatric disorders.

It would therefore be an advance in the art to discover IDO inhibitors that effective the balance of the aforementioned properties as a disease modifying therapy in chronic HIV infections to decrease the incidence of non-AIDS morbidity/mortality; and/or a disease modifying therapy to prevent mortality in sepsis; and/or an immunotherapy to enhance the immune response to HIV, HBV, HCV and other chronic viral infections, chronic bacterial infections, chronic fungal infections, and to tumors; and/or for the treatment of depression or other neurological/neuropsychiatric disorders.

Asghar, K., M. T. Ashiq, B. Zulfiqar, A. Mahroo, K. Nasir and S. Murad (2015). "Indoleamine 2,3-dioxygenase expression and activity in patients with hepatitis C virus-induced liver cirrhosis." Exp Ther Med 9(3): 901-904.

Balachandran, V. P., M. J. Cavnar, S. Zeng, Z. M. Bamboat, L. M. Ocuin, H. Obaid, E. C. Sorenson, R. Popow, C. Ariyan, F. Rossi, P. Besmer, T. Guo, C. R. Antonescu, T. Taguchi, J. Yuan, J. D. Wolchok, J. P. Allison and R. P. Dematteo (2011). "Imatinib potentiates antitumor T cell responses in gastrointestinal stromal tumor through the inhibition of Ido." Nature Medicine 17(9): 1094-1100.

Beatty, G. L., P. J. O'Dwyer, J. Clark, J. G. Shi, R. C. Newton, R. Schaub, J. Maleski, L. Leopold and T. Gajewski (2013). "Phase I study of the safety, pharmacokinetics (PK), and pharmacodynamics (PD) of the oral inhibitor of indoleamine 2,3-dioxygenase (IDO1) INCB024360 in patients (pts) with advanced malignancies." ASCO Meeting Abstracts 31(15_suppl): 3025.

Boasso, A., A. W. Hardy, S. A. Anderson, M. J. Dolan and G. M. Shearer (2008). "HIV-induced type I interferon and tryptophan catabolism drive T cell dysfunction despite phenotypic activation." PLoS One 3(8): e2961.

Boasso, A., J. P. Herbeuval, A. W. Hardy, S. A. Anderson, M. J. Dolan, D. Fuchs and G. M. Shearer (2007). "HIV inhibits CD4+ T-cell proliferation by inducing indoleamine 2,3-dioxygenase in plasmacytoid dendritic cells." Blood 109(8): 3351-3359.

Boasso, A. and G. M. Shearer (2008). "Chronic innate immune activation as a cause of HIV-1 immunopathogenesis." Clin Immunol 126(3): 235-242.

Boasso, A., M. Vaccari, A. Hryniewicz, D. Fuchs, J. Nacsa, V. Cecchinato, J. Andersson, G. Franchini, G. M. Shearer and C. Chougnet (2007). "Regulatory T-cell markers, indoleamine 2,3-dioxygenase, and virus levels in spleen and gut during progressive simian immunodeficiency virus infection." J Virol 81(21): 11593-11603.

Byakwaga, H., Y. Boum, 2nd, Y. Huang, C. Muzoora, A. Kembabazi, S. D. Weiser, J. Bennett, H. Cao, J. E. Haberer, S. G. Deeks, D. R. Bangsberg, J. M. McCune, J. N. Martin and P. W. Hunt (2014). "The kynurenine pathway of tryptophan catabolism, CD4+ T-cell recovery, and mortality among HIV-infected Ugandans initiating antiretroviral therapy." J Infect Dis 210(3): 383-391.

Chen, Y. B., S. D. Li, Y. P. He, X. J. Shi, Y. Chen and J. P. Gong (2009). "Immunosuppressive effect of IDO on T cells in patients with chronic hepatitis B*." Hepatol Res 39(5): 463-468.

Darcy, C. J., J. S. Davis, T. Woodberry, Y. R. McNeil, D. P. Stephens, T. W. Yeo and N. M. Anstey (2011). "An observational cohort study of the kynurenine to tryptophan ratio in sepsis: association with impaired immune and microvascular function." PLoS One 6(6): e21185.

Deeks, S. G. (2011). "HIV infection, inflammation, immunosenescence, and aging." Annu Rev Med 62: 141-155.

Favre, D., S. Lederer, B. Kanwar, Z. M. Ma, S. Proll, Z. Kasakow, J. Mold, L. Swainson, J. D. Barbour, C. R. Baskin, R. Palermo, I. Pandrea, C. J. Miller, M. G. Katze and J. M. McCune (2009). "Critical loss of the balance between Th17 and T regulatory cell populations in pathogenic SIV infection." PLoS Pathog 5(2): e1000295.

Favre, D., J. Mold, P. W. Hunt, B. Kanwar, P. Loke, L. Seu, J. D. Barbour, M. M. Lowe, A. Jayawardene, F. Aweeka, Y. Huang, D. C. Douek, J. M. Brenchley, J. N. Martin, F. M. Hecht, S. G. Deeks and J. M. McCune (2010). "Tryptophan catabolism by indoleamine 2,3-dioxygenase 1 alters the balance of TH17 to regulatory T cells in HIV disease." Sci Transl Med 2(32): 32ra36.

Frumento, G., R. Rotondo, M. Tonetti, G. Damonte, U. Benatti and G. B. Ferrara (2002). "Tryptophan-derived catabolites are responsible for inhibition of T and natural killer cell proliferation induced by indoleamine 2,3-dioxygenase." J Exp Med 196(4): 459-468.

Gangadhar, T., O. Hamid, D. Smith, T. Bauer, J. Wasser, J. Luke, A. Balmanoukian, D. Kaufman, Y. Zhao, J. Maleski, L. Leopold and T. Gajewski (2015). "Preliminary results from a Phase I/II study of epacadostat (incb024360) in combination with pembrolizumab in patients with selected advanced cancers." Journal for ImmunoTherapy of Cancer 3(Suppl 2): O7.

Holmgaard, R. B., D. Zamarin, Y. Li, B. Gasmi, D. H. Munn, J. P. Allison, T. Merghoub and J. D. Wolchok (2015). "Tumor-Expressed IDO Recruits and Activates MDSCs in a Treg-Dependent Manner." Cell Reports 13(2): 412-424.

Holmgaard, R. B., D. Zamarin, D. H. Munn, J. D. Wolchok and J. P. Allison (2013). "Indoleamine 2,3-dioxygenase is a critical resistance mechanism in antitumor T cell immunotherapy targeting CTLA-4." Journal of Experimental Medicine 210(7): 1389-1402.

Hoshi, M., Y. Osawa, H. Ito, H. Ohtaki, T. Ando, M. Takamatsu, A. Hara, K. Saito and M. Seishima (2014). "Blockade of indoleamine 2,3-dioxygenase reduces mortality from peritonitis and sepsis in mice by regulating functions of CD11b+ peritoneal cells." Infect Immun 82(11): 4487-4495.

Hotchkiss, R. S., G. Monneret and D. Payen (2013). "Sepsis-induced immunosuppression: from cellular dysfunctions to immunotherapy." Nat Rev Immunol 13(12): 862-874.

Hunt, P. W., E. Sinclair, B. Rodriguez, C. Shive, B. Clagett, N. Funderburg, J. Robinson, Y. Huang, L. Epling, J. N. Martin, S. G. Deeks, C. L. Meinert, M. L. Van Natta, D. A. Jabs and M. M. Lederman (2014). "Gut epithelial barrier dysfunction and innate immune activation predict mortality in treated HIV infection." J Infect Dis 210(8): 1228-1238.

Ito, H., T. Ando, K. Ando, T. Ishikawa, K. Saito, H. Moriwaki and M. Seishima (2014). "Induction of hepatitis B virus surface antigen-specific cytotoxic T lymphocytes can be up-regulated by the inhibition of indoleamine 2,3-dioxygenase activity." Immunology 142(4): 614-623.

Jung, I. D., M. G. Lee, J. H. Chang, J. S. Lee, Y. I. Jeong, C. M. Lee, W. S. Park, J. Han, S. K. Seo, S. Y. Lee and Y. M. Park (2009). "Blockade of indoleamine 2,3-dioxygenase protects mice against lipopolysaccharide-induced endotoxin shock." J Immunol 182(5): 3146-3154.

Larrea, E., J. I. Riezu-Boj, L. Gil-Guerrero, N. Casares, R. Aldabe, P. Sarobe, M. P. Civeira, J. L. Heeney, C. Rollier, B. Verstrepen, T. Wakita, F. Borras-Cuesta, J. J. Lasarte and J. Prieto (2007). "Upregulation of indoleamine 2,3-dioxygenase in hepatitis C virus infection." J Virol 81(7): 3662-3666.

Lepiller, Q., E. Soulier, Q. Li, M. Lambotin, J. Barths, D. Fuchs, F. Stoll-Keller, T. J. Liang and H. Barth (2015). "Antiviral and Immunoregulatory Effects of Indoleamine-2,3-Dioxygenase in Hepatitis C Virus Infection." J Innate Immun 7(5): 530-544.

Li, L., L. Huang, H. P. Lemos, M. Mautino and A. L. Mellor (2012). "Altered tryptophan metabolism as a paradigm for good and bad aspects of immune privilege in chronic inflammatory diseases." *Front Immunol* 3: 109.

Liu, X., N. Shin, H. K. Koblish, G. Yang, Q. Wang, K. Wang, L. Leffet, M. J. Hansbury, B. Thomas, M. Rupar, P. Waeltz, K. J. Bowman, P. Polam, R. B. Sparks, E. W. Yue, Y. Li, R. Wynn, J. S. Fridman, T. C. Burn, A. P. Combs, R. C. Newton and P. A. Scherle (2010). "Selective inhibition of IDO1 effectively regulates mediators of antitumor immunity." *Blood* 115(17): 3520-3530.

Loughman, J. A. and D. A. Hunstad (2012). "Induction of indoleamine 2,3-dioxygenase by uropathogenic bacteria attenuates innate responses to epithelial infection." *J Infect Dis* 205(12): 1830-1839.

Lovelace, M. D., B. Varney, G. Sundaram, M. J. Lennon, C. K. Lim, K. Jacobs, G. J. Guillemin and B. J. Brew (2016). "Recent evidence for an expanded role of the kynurenine pathway of tryptophan metabolism in neurological diseases." *Neuropharmacology.*

M. Mautino, C. J. L., N. Vahanian, J. Adams, C. Van Allen, M. D. Sharma, T. S. Johnson and D. H. Munn (2014). "Synergistic antitumor effects of combinatorial immune checkpoint inhibition with anti-PD-1/PD-L antibodies and the IDO pathway inhibitors NLG919 and indoximod in the context of active immunotherapy." April 2014 *AACR Meeting* Poater #5023.

Mattapallil, J. J., D. C. Douek, B. Hill, Y. Nishimura, M. Martin and M. Roederer (2005). "Massive infection and loss of memory CD4+ T cells in multiple tissues during acute SIV infection." *Nature* 434(7037): 1093-1097.

Mellor, A. L. and D. H. Munn (2004). "IDO expression by dendritic cells: Tolerance and tryptophan catabolism." *Nature Reviews Immunology* 4(10): 762-774.

Munn, D. H. (2011). "Indoleamine 2,3-dioxygenase, Tregs and cancer." *Current Medicinal Chemistry* 18(15): 2240-2246.

Munn, D. H., E. Shafizadeh, J. T. Attwood, I. Bondarev, A. Pashine and A. L. Mellor (1999). "Inhibition of T cell proliferation by macrophage tryptophan catabolism." *J Exp Med* 189(9): 1363-1372.

Pilotte, L., P. Larrieu, V. Stroobant, D. Colau, E. Dolušić, R. Frédérick, E. De Plaen, C. Uyttenhove, J. Wouters, B. Masereel and B. J. Van Den Eynde (2012). "Reversal of tumoral immune resistance by inhibition of tryptophan 2,3-dioxygenase." *Proceedings of the National Academy of Sciences of the United States of America* 109(7): 2497-2502.

Sekkai, D., O. Guittet, G. Lemaire, J. P. Tenu and M. Lepoivre (1997). "Inhibition of nitric oxide synthase expression and activity in macrophages by 3-hydroxyanthranilic acid, a tryptophan metabolite." *Arch Biochem Biophys* 340(1): 117-123.

Suzuki, Y., T. Suda, K. Asada, S. Miwa, M. Suzuki, M. Fujie, K. Furuhashi, Y. Nakamura, N. Inui, T. Shirai, H. Hayakawa, H. Nakamura and K. Chida (2012). "Serum indoleamine 2,3-dioxygenase activity predicts prognosis of pulmonary tuberculosis." *Clin Vaccine Immunol* 19(3): 436-442.

Tattevin, P., D. Monnier, O. Tribut, J. Dulong, N. Bescher, F. Mourcin, F. Uhel, Y. Le Tulzo and K. Tarte (2010). "Enhanced indoleamine 2,3-dioxygenase activity in patients with severe sepsis and septic shock." *J Infect Dis* 201(6): 956-966.

Tenorio, A. R., Y. Zheng, R. J. Bosch, S. Krishnan, B. Rodriguez, P. W. Hunt, J. Plants, A. Seth, C. C. Wilson, S. G. Deeks, M. M. Lederman and A. L. Landay (2014). "Soluble markers of inflammation and coagulation but not T-cell activation predict non-AIDS-defining morbid events during suppressive antiretroviral treatment." *J Infect Dis* 210(8): 1248-1259.

Wainwright, D. A., I. V. Balyasnikova, A. L. Chang, A. U. Ahmed, K.-S. Moon, B. Auffinger, A. L. Tobias, Y. Han and M. S. Lesniak (2012). "IDO Expression in Brain Tumors Increases the Recruitment of Regulatory T Cells and Negatively Impacts Survival." *Clinical Cancer Research* 18(22): 6110-6121.

Wainwright, D. A., A. L. Chang, M. Dey, I. V. Balyasnikova, C. K. Kim, A. Tobias, Y. Cheng, J. W. Kim, J. Qiao, L. Zhang, Y. Han and M. S. Lesniak (2014). "Durable therapeutic efficacy utilizing combinatorial blockade against IDO, CTLA-4, and PD-L1 in mice with brain tumors." *Clinical Cancer Research* 20(20): 5290-5301.

Yue, E. W., B. Douty, B. Wayland, M. Bower, X. Liu, L. Leffet, Q. Wang, K. J. Bowman, M. J. Hansbury, C. Liu, M. Wei, Y. Li, R. Wynn, T. C. Burn, H. K. Koblish, J. S. Fridman, B. Metcalf, P. A. Scherle and A. P. Combs (2009). "Discovery of potent competitive inhibitors of indoleamine 2,3-dioxygenase with in vivo pharmacodynamic activity and efficacy in a mouse melanoma model." *Journal of Medicinal Chemistry* 52(23): 7364-7367.

SUMMARY OF THE INVENTION

Briefly, in one aspect, the present invention discloses compounds of Formula I

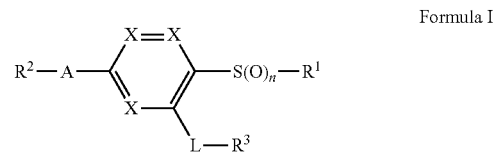

Formula I or a pharmaceutically acceptable salt thereof wherein:

n is 0, 1, or 2;

either each X is CH to form a benzene ring, or one X is N while the other two are CH to form a pyridine ring;

$R^1$ is $C_{1-6}$alkyl optionally substituted with a methoxy, a 4 to 6-membered heterocycle containing 1 or heteroatoms selected from N, S, and O, or phenyl;

A is $C_{1-4}$alkylene, $C_{2-4}$alkenylene, a benzene ring, or pyridine ring;

$R^2$ is cyano, $C(O)NH_2$, $CO_2H$, $C(NH)NH$—OH, or a 4 to 6-membered heterocycle or heteroaryl containing 1 to 4 heteroatoms selected from N, S, and O, wherein said heterocycle or heteroaryl may optionally be substituted by a substituent selected from the group consisting of halogen, $C_{3-6}$cycloalkyl, $CH_2OH$, $CH_2OC_{1-3}$alkyl, $C_{1-3}$alkyleneOC(O)$C_{1-4}$alkyl, $C_{1-3}$alkyl optionally substituted by 1-3 halogens, and wherein said $CH_2OH$ is optionally converted into a prodrug by converting the $CH_2OH$ group to a $CH_2OC(O)CH_3$, $CH_2OC(O)C(C_{1-4}alkyl)_3$, or $OP(O)(OH)_2$ group, or $OP(O)(OC_{1-4}alkyl)_2$ group;

L is a linking group selected from $NHC(O)C_{1-3}$alkylene, NHC(O)NH, NH, NHC(O), NHC(O)O;

$R^3$ is $C_{1-3}$alkyl, $OC_{1-3}$alkyl, $C_{3-6}$cycloalkyl, phenyl, or a 4 to 6-membered heterocycle or heteroaryl containing 1 to 4 heteroatoms selected from N, S, and O; and wherein said $C_{3-6}$cycloalkyl, phenyl, heterocycle, or heteroaryl, may optionally be substituted by one to three substituents selected from the group consisting of halogen, cyano, $C_{1-3}$alkyl optionally substituted by 1-3 halogens, $C_{3-6}$cycloalkyl, SO$_2$CH$_3$, —OCH$_3$, CH$_2$OH, C$_{3-6}$cycloalkyl, CH$_2$OC$_{1-4}$alkyl, C(O)OC$_{1-4}$alkyl, C(O)CH$_3$, and OCH$_3$, or two substituents bonded to adjacent atoms may join together to form a fused 5 or 6 membered ring optionally containing 1 or two heteroatoms selected from O, S, and N, fused to said C$_{3-6}$cycloalkyl, phenyl, heterocycle, or heteroaryl. In another aspect, the present invention discloses pharmaceutical compositions comprising a compound of Formula I or a pharmaceutically acceptable salt thereof.

In another aspect, the present invention discloses a method for treating diseases or conditions that would benefit from inhibition of IDO.

DETAILED DESCRIPTION OF REPRESENTATIVE EMBODIMENTS

Preferably n is 0.

Preferably, when one X is N, said N is positioned adjacent to the carbon atom to which the depicted S is bonded.

Preferably, R$^1$ is C$_{1-6}$alkyl. Most preferably, R$^1$ is t-butyl.

Preferably, when A is a benzene ring or a pyridine ring, R$^2$ is ortho to the depicted X-containing ring in Formula I. Preferably, when A is C$_{1-4}$alkylene, A is ethylene or isopropylene.

Preferably A is a benzene or pyridine ring. Most preferably A is a benzene ring.

Preferably, R$^2$ is a 5-membered heterocycle or heteroaryl containing 1 to 4 heteroatoms selected from N, S, and O, wherein said heterocycle or heteroaryl may optionally be substituted by a substituent selected from the group consisting of halogen, C$_{3-6}$cycloalkyl, CH$_2$OH, CH$_2$OC$_{1-3}$alkyl, C$_{1-3}$alkyleneOC(O)C$_{1-4}$alkyl, C$_{1-3}$alkyl optionally substituted by 1-3 halogens, and wherein said CH$_2$OH is optionally converted into a prodrug by converting the CH$_2$OH group to a CH$_2$OC(O)CH$_3$, CH$_2$OC(O)C(C$_{1-4}$alkyl)$_3$, or OP(O)(OH)$_2$ group, or OP(O)(OC$_{1-4}$alkyl)$_2$ group. Most preferably R$^2$ is a tetrazole ring optionally substituted by CH$_2$OH and wherein said CH$_2$OH is optionally converted into a prodrug by converting the CH$_2$OH group to a CH$_2$OC(O)CH$_3$, CH$_2$OC(O)C(C$_{1-4}$alkyl)$_3$, or OP(O)(OH)$_2$ group, or OP(O)(OC$_{1-4}$alkyl)$_2$ group.

Preferably L is NHC(O)C$_{1-3}$alkylene. Most preferably L is NHC(O)CH$_2$.

Preferably R$^3$ is phenyl, or a 4 to 6-membered heterocycle or heteroaryl containing 1 to 4 heteroatoms selected from N, S, and O; and wherein said phenyl, heterocycle, or heteroaryl, may optionally substituted by one to three substituents selected from the group consisting of halogen, cyano, C$_{1-3}$alkyl optionally substituted by 1-3 halogens, C$_{3-6}$cycloalkyl, SO$_2$CH$_3$, —OCH$_3$, CH$_2$OH, C$_{3-6}$cycloalkyl, CH$_2$OC$_{1-4}$alkyl, C(O)OC$_{1-4}$alkyl, C(O)CH$_3$, and OCH$_3$, or two substituents bonded to adjacent atoms may join together to form a fused 5 or 6 membered ring optionally containing 1 or two heteroatoms selected from O, S, and N, fused to said C$_{3-6}$cycloalkyl, phenyl, heterocycle, or heteroaryl. Most preferably, R$^3$ is phenyl, or a 4 to 6-membered heterocycle or heteroaryl containing 1 to 4 heteroatoms selected from N, S, and O; and wherein said phenyl, heterocycle, or heteroaryl, may optionally substituted by one to three C$_{1-3}$alkyl groups each of which is optionally substituted by 1-3 halogens.

In particular, it is expected that the compounds and composition of this invention will be useful for prevention and/or treatment of HIV; including the prevention of the progression of AIDS and general immunosuppression. It is expected that in many cases such prevention and/or treatment will involve treating with the compounds of this invention in combination with at least one other drug thought to be useful for such prevention and/or treatment. For example, the IDO inhibitors of this invention may be used in combination with other immune therapies such as immune checkpoints (PD1, CTLA4, ICOS, etc.) and possibly in combination with growth factors or cytokine therapies (IL21, IL-7, etc.).

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or ACN are preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In another embodiment of the invention, there is provided a compound of Formula I, wherein the compound or salt of the compound is used in the manufacture of a medicament for use in the treatment immunosuppression in a human.

In another embodiment of the invention, there is provided a pharmaceutical composition comprising a pharmaceutically acceptable diluent and a therapeutically effective amount of a compound as defined in Formula I.

In one embodiment, the pharmaceutical formulation containing a compound of Formula I or a salt thereof is a formulation adapted for parenteral administration. In another embodiment, the formulation is a long-acting parenteral formulation. In a further embodiment, the formulation is a nano-particle formulation.

The present invention is directed to compounds, compositions and pharmaceutical compositions that have utility as novel treatments for immunosuppresion. While not wanting to be bound by any particular theory, it is thought that the present compounds are able to inhibit the enzyme that catalyzes the oxidative pyrrole ring cleavage reaction of I-Trp to N-formylkynurenine utilizing molecular oxygen or reactive oxygen species.

Therefore, in another embodiment of the present invention, there is provided a method for the prevention and/or treatment of HIV; including the prevention of the progression of AIDS and general immunosuppression.

EXAMPLES

The following examples serve to more fully describe the manner of making and using the above-described invention. It is understood that these examples in no way serve to limit the true scope of the invention, but rather are presented for illustrative purposes. In the examples and the synthetic schemes below, the following abbreviations have the following meanings. If an abbreviation is not defined, it has its generally accepted meaning.

ACN=acetonitrile
AIBN=azobisisobutyronitrile
aq.=aqueous
μL or uL=microliters
μM or uM=micromolar
NMR=nuclear magnetic resonance
boc=tert-butoxycarbonyl
br=broad
Cbz=Benzyloxycarbonyl
CDI=1,1'-carbonyldiimidazole
d=doublet
δ=chemical shift
° C.=degrees celsius
DCM=dichloromethane
dd=doublet of doublets
DHP=dihydropyran
DIAD=diisopropyl azodicarboxylate
DIEA or DIPEA=N,N-diisopropylethylamine
DMAP=4-(dimethylamino)pyridine
DMEM=Dulbeco's Modified Eagle's Medium
DMF=dimethylformamide
EtOAc=ethyl acetate
h or hr=hours
HATU=1-[Bis(dimethylamino)methylene]-1H-1,2,3-triazolo[4,5-b]pyridinium 3-oxid hexafluorophosphate
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)
KHMDS=potassium bis(trimethylsilyl)amide
LCMS=liquid chromatography-mass spectrometry
m=multiplet
M=molar
$M+H^+$=parent mass spectrum peak plus $H^+$
MeOH=methanol
mg=milligram
min=minutes
mL=milliliter
mM=millimolar
mmol=millimole
MS=mass spectrum
MTBE=methyl tert-butyl ether
N=normal
NFK=N-formylkynurenine
NBS=N-bromosuccinimide
nm=nanomolar
NMP=N-methyl-2-pyrrolidone
PE=petroleum ether
ppm=parts per million
q.s.=sufficient amount
s=singlet
RT=room temperature
Rf=retardation factor
sat.=saturated
t=triplet
TEA=triethylamine
tetrakis=tetrakis(triphenylphosphine)palladium(0)
TFA=trifluoroacetic acid
TFAA=trifluoroacetic anhydride
THF=tetrahydrofuran $^1$H NMR spectra were recorded on a Bruker Ascend 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Waters ACQUITY UPLC with SQ Detectors using a Waters BEH C18, 2.1×50 mm, 1.7 μm using a gradient elution method.

Solvent A: 0.1% formic acid (FA) in water;

Solvent B: 0.1% FA in acetonitrile;

30% B for 0.5 min followed by 30-100% B over 2.5 min.

Scheme I: Synthesis of N-(4-(tert-butylthio)-2'-(2H-tetrazol-5-yl)-[1,1'-biphenyl]-3-yl)-2-(p-tolyl)acetamide -continued

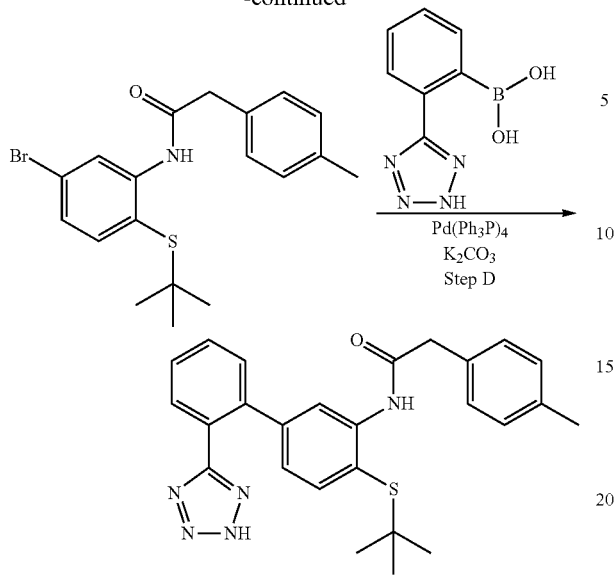

Example 1: N-(4-(tert-butylthio)-2'-(2H-tetrazol-5-yl)-[1,1'-biphenyl]-3-yl)-2-(p-tolyl)acetamide

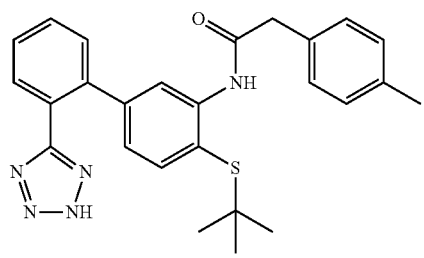 [SMILES: Cc1ccc(CC(=O)Nc2cc(-c3ccccc3-c3nn[nH]n3)ccc2SC(C)(C)C)cc1]

Step A (4-Bromo-2-nitrophenyl)(tert-butyl)sulfane

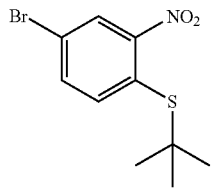

To a solution of 4-bromo-1-fluoro-2-nitrobenzene (5.53 g, 24.39 mmol) in acetonitrile (100 mL) was added cesium carbonate (7.23 g, 22.18 mmol) followed by 2-methylpropane-2-thiol (2.50 mL, 22.18 mmol) and the mixture was stirred at ambient temperature for 18 h and then at 70° C. for 5 h. The mixture was filtered washing the solid with EtOAc. The filtrate was concentrated and purified on silica gel (EtOAc/hexanes 0-5%) to provide (4-bromo-2-nitrophenyl)(tert-butyl)sulfane (6.01 g, 18.64 mmol, 84% yield) as a yellow oil. $^1$H NMR (400 MHz, CHLOROFORM-d): δ ppm 1.32 (s, 9H), 7.55-7.60 (m, 1H), 7.61-7.67 (m, 1H), 7.81 (d, J=1.95 Hz, 1H).

Step B

5-Bromo-2-(tert-butylthio)aniline

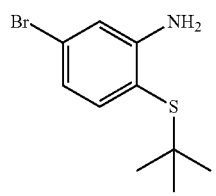

To a solution of (4-bromo-2-nitrophenyl)(tert-butyl)sulfane (6.01 g, 20.71 mmol) in ethanol (140 mL) was added zinc (12.31 g, 188 mmol), ammonium chloride (10.07 g, 188 mmol) and water (28.0 mL) and the mixt. was stirred at ambient temperature for 2 h. The mixture was filtered and concentrated and the residue was partitioned between EtOAc and water. The organic phase was dried ($Na_2SO_4$), concentrated and dried to provide the desired product (4.97 g, 18.15 mmol, 96% yield) as a yellow solid. LCMS (M+H)$^+$: m/z=260.05. $^1$H NMR (400 MHz, CHLOROFORM-d): δ ppm 1.31 (s, 9H), 6.81 (dd, J=8.20, 2.15 Hz, 1H), 6.93 (d, J=1.95 Hz, 1H), 7.21 (d, J=8.20 Hz, 1H).

Step C

N-(5-Bromo-2-(tert-butylthio)phenyl)-2-(p-tolyl)acetamide

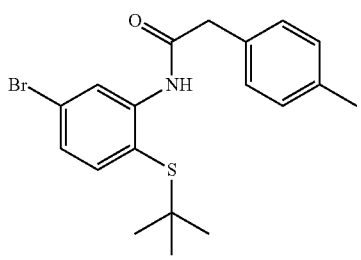 [SMILES: Cc1ccc(CC(=O)Nc2cc(Br)ccc2SC(C)(C)C)cc1]

To a mixture of 5-bromo-2-(tert-butylthio)aniline (1.31 g, 4.78 mmol), 2-(p-tolyl)acetic acid (0.79 g, 5.26 mmol) and DIEA (2.08 mL, 11.96 mmol) in EtOAc (35 mL) was added 2,4,6-tripropyl-1,3,5,2,4,6-trioxatriphosphinane 2,4,6-trioxide (3.65 g, 5.74 mmol) (50%/EtOAc) and the mixture was stirred at ambient temperature for 18 h. The mixture was washed with water and the organic phase was dried ($Na_2SO_4$), concentrated and dried to provide the desired product (1.62 g, 4.13 mmol, 86% yield) as a yellow solid. LCMS (M+1)$^+$: m/z=392.2. $^1$H NMR (400 MHz, CHLOROFORM-d): δ ppm 1.01 (s, 9H), 2.38 (s, 3H), 3.76 (s, 2H), 7.12-7.20 (m, 1H), 7.28 (s, 6H), 8.83 (d, J=2.07 Hz, 1H).

Step D

N-(4-(tert-butylthio)-2'-(2H-tetrazol-5-yl)-[1,1'-biphenyl]-3-yl)-2-(p-tolyl)acetamide

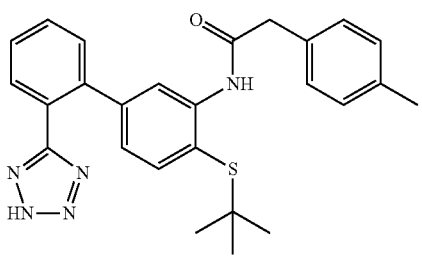 [SMILES: Cc1ccc(CC(=O)Nc2cc(-c3ccccc3-c3nn[nH]n3)ccc2SC(C)(C)C)cc1]

A solution of N-(5-bromo-2-(tert-butylthio)phenyl)-2-(p-tolyl)acetamide (1.61 g, 4.10 mmol) in DMF (30 mL) was degassed with a stream of nitrogen while sequentially adding (2-(2H-tetrazol-5-yl)phenyl)boronic acid (2.34 g, 12.31 mmol), potassium carbonate (2.27 g, 16.41 mmol), water (6.00 mL) and tetrakis(triphenylphosphine) palladium(0) (0.47 g, 0.410 mmol) and then placed in a pre-heated oil bath at 100° C. The temperature was increased to 130° C. and the mixture was stirred under nitrogen atmosphere for 2 h. Water was added and 1N HCl/water was added to pH~4-5. The solid was filtered washing with water. The solid was dissolved in EtOAc and the org. phase was dried (Na$_2$SO$_4$), concentrated and purified on silica gel (EtOAc/dichloromethane 0-40%) to provide the title compound (1.32 g, 2.88 mmol, 70.3% yield) as a light pink solid. LCMS (M+1)$^+$: m/z=458.4. $^1$H NMR (400 MHz, DMSO-d$_6$): δ ppm 1.01 (s, 9H), 2.31 (s, 3H), 3.72 (s, 2H), 6.71 (dd, J=8.01, 1.76 Hz, 1H), 7.20-7.25 (m, 2H), 7.26-7.31 (m, 2H), 7.34 (d, J=7.81 Hz, 1H), 7.54-7.65 (m, 2H), 7.67-7.75 (m, 2H), 8.21 (s, 1H), 8.96 (s, 1H).

Examples 2 and 3: N-(4-(tert-butylsulfinyl)-2'-(2H-tetrazol-5-yl)-[1,1'-biphenyl]-3-yl)-2-(p-tolyl)acetamide and N-(4-(tert-butylsulfonyl)-2'-(2H-tetrazol-5-yl)-[1,1'-biphenyl]-3-yl)-2-(p-tolyl)acetamide Example 2

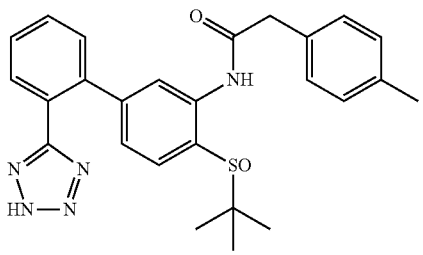

Example 3

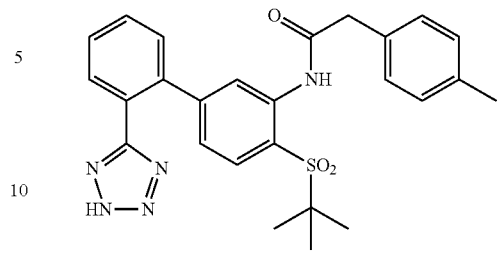

To a solution of N-(4-(tert-butylthio)-2'-(2H-tetrazol-5-yl)-[1,1'-biphenyl]-3-yl)-2-(p-tolyl)acetamide (44 mg, 0.087 mmol) in acetic acid (0.5 mL)/dichloromethane (0.5 mL) was added dropwise a 3% solution of potassium permanganate (0.2 mL, 0.038 mmol). After 1 h at ambient temperature more 3% solution of potassium permanganate (0.1 mL, 0.019 mmol) was added. After 15 min saturated Na$_2$S$_2$O$_3$/water was added followed by addition of saturated NaHCO$_3$/water. The mixture was extracted with EtOAc and the organic phase was dried (Na$_2$SO$_4$), concentrated and purified by HPLC (RP C18, MeCN/water 10-100%, 0.1% formic acid) to provide N-(4-(tert-butylsulfinyl)-2'-(2H-tetrazol-5-yl)-[1,1'-biphenyl]-3-yl)-2-(p-tolyl)acetamide (24.8 mg, 0.052 mmol, 60.5% yield) and N-(4-(tert-butylsulfonyl)-2'-(2H-tetrazol-5-yl)-[1,1'-biphenyl]-3-yl)-2-(p-tolyl)acetamide (12.6 mg, 0.026 mmol, 29.7% yield). Example 2: LCMS (M+1)$^+$: m/z=474.4. $^1$H NMR (400 MHz, DMSO-d$_6$): δ ppm 0.98 (s, 9H), 2.28 (s, 3H), 3.55 (s, 2H), 6.94 (d, J=8.01 Hz, 1H), 7.10-7.25 (m, 4H), 7.38 (d, J=8.20 Hz, 1H), 7.53-7.66 (m, 2H), 7.67-7.78 (m, 3H), 10.41 (br. s., 1H). Example 3: LCMS (M+1)$^+$: m/z=490.3. $^1$H NMR (400 MHz, DMSO-d$_6$): δ ppm 1.09 (s, 9H), 2.29 (s, 3H), 3.69 (s, 2H), 6.96 (d, J=8.20 Hz, 1H), 7.13-7.26 (m, 4H), 7.56-7.69 (m, 3H), 7.70-7.82 (m, 2H), 8.31 (s, 1H), 9.78 (s, 1H).

Example 4: 4'-(tert-Butylthio)-3'-(2-(p-tolyl)acetamido)-[1,1'-biphenyl]-2-carboxylic acid

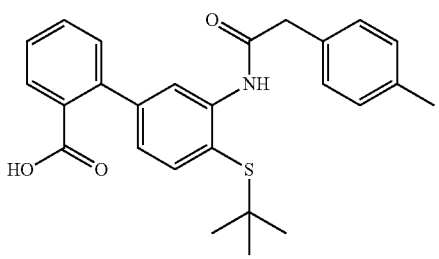 [SMILES: Cc1ccc(CC(=O)Nc2cc(-c3ccccc3C(=O)O)ccc2SC(C)(C)C)cc1]

This compound was prepared following the procedure described in Step D (Scheme I) from 2-boronobenzoic acid. LCMS (M+1)$^+$: m/z=434.4. $^1$H NMR (400 MHz, DMSO-d$_6$): δ ppm 1.04 (s, 9H), 2.31 (s, 3H), 3.75 (s, 2H), 7.03 (dd, J=7.91, 1.86 Hz, 1H), 7.21-7.26 (m, 2H), 7.29-7.34 (m, 2H), 7.38 (d, J=7.42 Hz, 1H), 7.44-7.52 (m, 2H), 7.56-7.63 (m, 1H), 7.75 (d, J=7.03 Hz, 1H), 8.35 (d, J=1.76 Hz, 1H), 9.01 (s, 1H), 12.80 (br. s., 1H).

Example 5: N-(4-(tert-butylthio)-2'-(2H-tetrazol-5-yl)-[1,1'-biphenyl]-3-yl)-2-(pyrazin-2-yl)acetamide

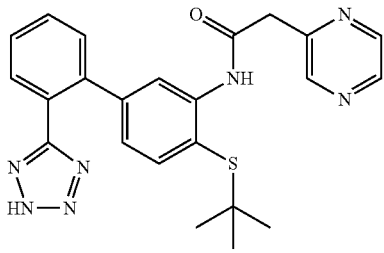 [SMILES: CC(C)(C)Sc1ccc(-c2ccccc2-c2nn[nH]n2)cc1NC(=O)Cc1cnccn1]

This compound was prepared from 2-(pyrazin-2-yl)acetic acid following the procedure described in Step C and D (Scheme I). LCMS (M+1)⁺: m/z=446.4. $^1$H NMR (400 MHz, DMSO-$d_6$): δ ppm 1.16 (s, 9H), 4.05 (s, 2H), 6.76 (d, J=7.87 Hz, 1H), 7.40 (d, J=8.06 Hz, 1H), 7.59 (dd, J=18.86, 7.33 Hz, 2H), 7.66-7.75 (m, 2H), 8.09 (s, 1H), 8.61 (d, J=2.38 Hz, 1H), 8.67 (s, 1H), 8.73 (s, 1H), 9.64 (s, 1H).

Example 6: N-(4-(tert-butylthio)-2'-(2H-tetrazol-5-yl)-[1,1'-biphenyl]-3-yl)-2-(pyridin-4-yl)acetamide

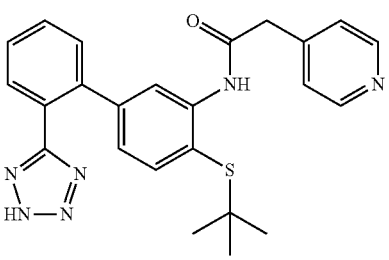 [SMILES: CC(C)(C)Sc1ccc(-c2ccccc2-c2nn[nH]n2)cc1NC(=O)Cc1ccncc1]

This compound was prepared from 2-(pyridin-4-yl)acetic acid following the procedure described in Step C and D (Scheme I). LCMS (M+1)⁺: m/z=445.4. $^1$H NMR (400 MHz, DMSO-$d_6$): δ ppm 1.10 (s, 9H), 3.84 (s, 2H), 6.77 (dd, J=8.06, 1.65 Hz, 1H), 7.39 (d, J=7.14 Hz, 3H), 7.53-7.64 (m, 2H), 7.69 (d, J=7.33 Hz, 2H), 8.01 (s, 1H), 8.56 (d, J=3.48 Hz, 2H), 9.23 (s, 1H).

Example 7: N-(4-(tert-butylthio)-2'-(2H-tetrazol-5-yl)-[1,1'-biphenyl]-3-yl)-2-(4-cyanophenyl)acetamide

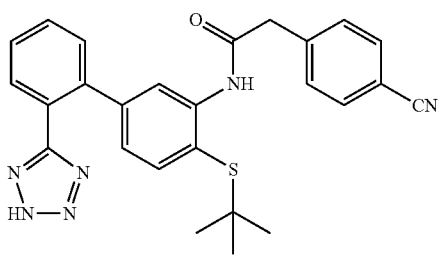 [SMILES: CC(C)(C)Sc1ccc(-c2ccccc2-c2nn[nH]n2)cc1NC(=O)Cc1ccc(C#N)cc1]

This compound was prepared from 2-(4-cyanophenyl)acetic acid following the procedure described in Step C and D (Scheme I). LCMS (M+1)⁺: m/z=469.4. $^1$H NMR (400 MHz, DMSO-$d_6$): δ ppm 1.09 (s, 9H), 3.91 (s, 2H), 6.77 (d, J=7.87 Hz, 1H), 7.39 (d, J=7.87 Hz, 1H), 7.52-7.64 (m, 4H), 7.69 (d, J=7.14 Hz, 2H), 7.86 (d, J=8.24 Hz, 2H), 8.02 (s, 1H), 9.18 (s, 1H).

Example 8: N-(4-(tert-butylthio)-2'-(2H-tetrazol-5-yl)-[1,1'-biphenyl]-3-yl)-2-(3-methylisoxazol-5-yl)acetamide

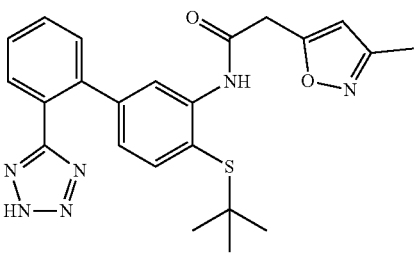 [SMILES: Cc1cc(CC(=O)Nc2cc(-c3ccccc3-c3nn[nH]n3)ccc2SC(C)(C)C)on1]

This compound was prepared from 2-(3-methylisoxazol-5-yl)acetic acid following the procedure described in Step C and D (Scheme I). LCMS (M+1)⁺: m/z=449.4. $^1$H NMR (400 MHz, DMSO-$d_6$): δ ppm 1.18 (s, 9H), 2.24 (s, 3H), 4.05 (s, 2H), 6.34 (s, 1H), 6.80 (dd, J=8.01, 1.76 Hz, 1H), 7.43 (d, J=8.01 Hz, 1H), 7.55-7.67 (m, 2H), 7.70 (d, J=7.42 Hz, 2H), 8.00 (s, 1H), 9.39 (s, 1H).

Example 9: N-(4-(tert-butylthio)-2'-(2H-tetrazol-5-yl)-[1,1'-biphenyl]-3-yl)-2-(pyrimidin-5-yl)acetamide

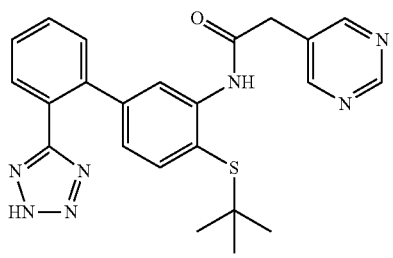

This compound was prepared from 2-(pyrimidin-5-yl)acetic acid following the procedure described in Step C and D (Scheme I). LCMS (M+1)⁺: m/z=446.3. $^1$H NMR (400 MHz, DMSO-$d_6$): δ ppm 1.16 (s, 9H), 3.89 (s, 2H), 6.79 (d, J=7.87 Hz, 1H), 7.42 (d, J=7.87 Hz, 1H), 7.58 (dd, J=19.59, 7.33 Hz, 3H), 7.69 (d, J=7.14 Hz, 2H), 7.93 (s, 1H), 8.79 (s, 2H), 9.11 (s, 1H), 9.42 (s, 1H).

Example 10: N-(4-(phenylthio)-2'-(2H-tetrazol-5-[1,1'-biphenyl]-3-yl)-2-(p-tolyl)acetamide

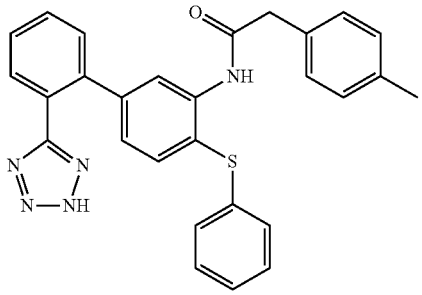

This compound was synthesized starting from 4-bromo-1-fluoro-2-nitrobenzene and thiophenol following Steps A-D (Scheme I) to provide the desired product as a trifluoroacetic acid salt. LCMS (M+1)+: m/z=478.36. ¹H NMR (400 MHz, DMSO-d₆): δ ppm 2.26 (s, 3H), 3.5 (br s, 1H), 3.57 (s, 2H), 6.82 (d, J=8.00 Hz, 1H), 7.02-7.10 (m, 4H), 7.12 (d, J=7.31 Hz, 2H), 7.19-7.39 (m, 4H), 7.51-7.75 (m, 5H), 9.37 (s, 1H).

Scheme II: Synthesis of N-(4-((3-methoxypropyl)thio)-2'-(2H-tetrazol-5-yl)-[1,1'-biphenyl]-3-yl)-2-(p-tolyl)acetamide

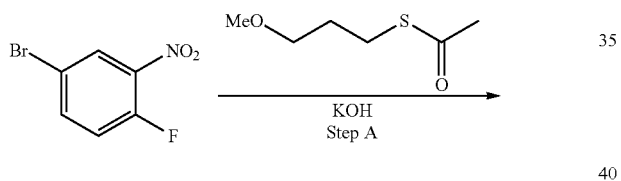

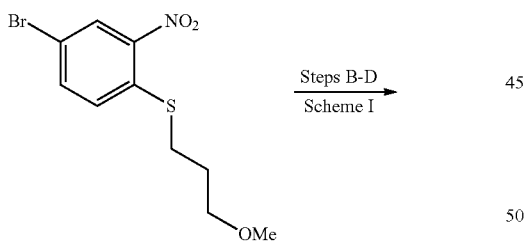

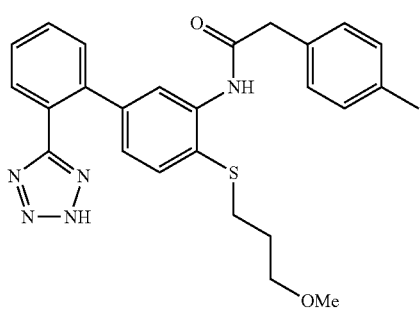 [SMILES: COCCCSc1ccc(-c2ccccc2-c2nn[nH]n2)cc1NC(=O)Cc1ccc(C)cc1]

Example 11: N-(4-((3-methoxypropyl)thio)-2'-(2H-tetrazol-5-yl)-[1,1'-biphenyl]-3-yl)-2-(p-tolyl)acetamide

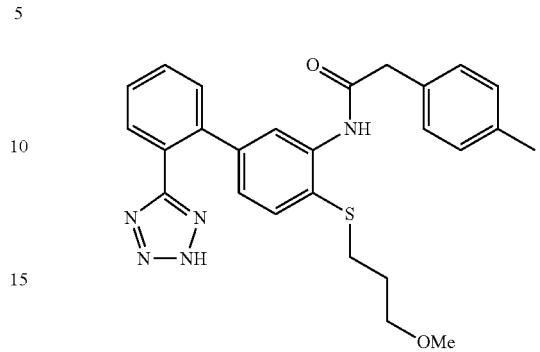

Step A (4-Bromo-2-nitrophenyl)(3-methoxypropyl)sulfane

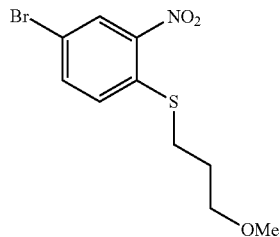 [SMILES: COCCCSc1ccc(Br)cc1[N+](=O)[O-]]

A solution of 1-((3-methoxypropyl)sulfinyl)ethanone (0.81 g, 4.93 mmol) in EtOH (15 mL) was degassed with a stream of nitrogen for 10 min then potassium hydroxide (0.749 g, 11.34 mmol) (85%) was added and the mixture was stirred under nitrogen for 10 min until it became a cloudy solution. A solution of 4-bromo-1-fluoro-2-nitrobenzene (1.194 g, 5.43 mmol) in EtOH (1.5 mL) was added dropwise and the mixture was stirred at ambient temperature for 30 min. The mixture was concentrated and partitioned between EtOAc and water. The organic phase was washed with brine, dried (Na₂SO₄), concentrated to provide (4-bromo-2-nitrophenyl)(3-methoxypropyl)sulfane (1.3 g, 71% yield). ¹H NMR (400 MHz, CHLOROFORM-d): δ ppm 1.91-2.04 (m, 2H), 3.06 (t, J=7.32 Hz, 2H), 3.36 (s, 3H), 3.52 (t, J=5.76 Hz, 2H), 7.34 (d, J=8.79 Hz, 1H), 7.65 (dd, J=8.69, 2.25 Hz, 1H), 8.35 (d, J=2.15 Hz, 1H).

Step B-D (N-(4-((3-methoxypropyl)thio)-2'-(2H-tetrazol-5-yl)-[1,1'-biphenyl]-3-yl)-2-(p-tolyl)acetamide

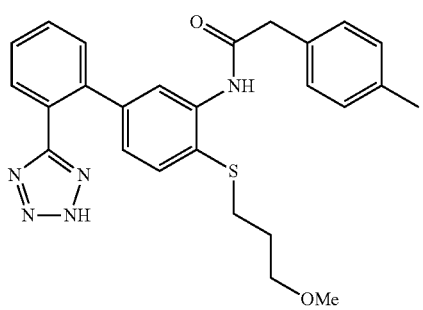 [SMILES: COCCCSc1ccc(-c2ccccc2-c2nn[nH]n2)cc1NC(=O)Cc1ccc(C)cc1]

This compound was prepared from (4-bromo-2-nitrophenyl)(3-methoxypropyl)sulfane following Steps B-D described in Scheme I. LCMS (M+1)⁺: m/z=474.4. ¹H NMR (400 MHz, DMSO-d₆): δ ppm 1.66 (quin, J=6.64 Hz, 2H), 2.28 (s, 3H), 2.78 (t, J=7.13 Hz, 2H), 3.19 (s, 3H), 3.30-3.35 (m, 2H), 3.65 (s, 2H), 6.79 (d, J=7.62 Hz, 1H), 7.11-7.18 (m, 2H), 7.23 (d, J=7.62 Hz, 2H), 7.32 (d, J=8.20 Hz, 1H), 7.48-7.54 (m, 2H), 7.55-7.61 (m, 1H), 7.64-7.72 (m, 2H), 9.27 (s, 1H).

Example 12: N-(4-((tetrahydro-2H-pyran-4-yl)thio)-2'-(2H-tetrazol-5-yl)-[1,1'-biphenyl]-3-yl)-2-(p-tolyl)acetamide

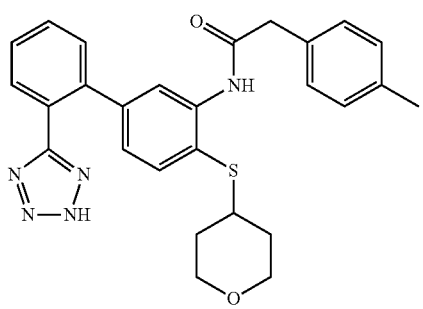 [SMILES: Cc1ccc(CC(=O)Nc2cc(-c3ccccc3-c3nn[nH]n3)ccc2SC2CCOCC2)cc1]

This compound was synthesized starting from 4-bromo-1-fluoro-2-nitrobenzene and S-(tetrahydro-2H-pyran-4-yl)ethanethioate following the procedure described in Scheme II to provide the desired product. LCMS (M+1)⁺: m/z=486.4. ¹H NMR (400 MHz, DMSO-d₆): δ ppm 1.20-1.36 (m, 2H), 1.55 (d, J=12.11 Hz, 2H), 2.29 (s, 3H), 3.02 (t, J=10.55 Hz, 1H), 3.21 (t, J=10.55 Hz, 2H), 3.69 (s, 2H), 3.75 (d, J=11.52 Hz, 2H), 6.74 (d, J=7.03 Hz, 1H), 7.15-7.21 (m, 2H), 7.23-7.30 (m, 2H), 7.38 (d, J=8.01 Hz, 1H), 7.53 (d, J=7.62 Hz, 1H), 7.56-7.63 (m, 1H), 7.65-7.74 (m, 2H), 7.85 (s, 1H), 9.10 (s, 1H).

Scheme III: Synthesis of 1-(4-(tert-butylsulfonyl)-2'-(2H-tetrazol-5-yl)-[1,1'-biphenyl]-3-yl)-3-(p-tolyl)urea

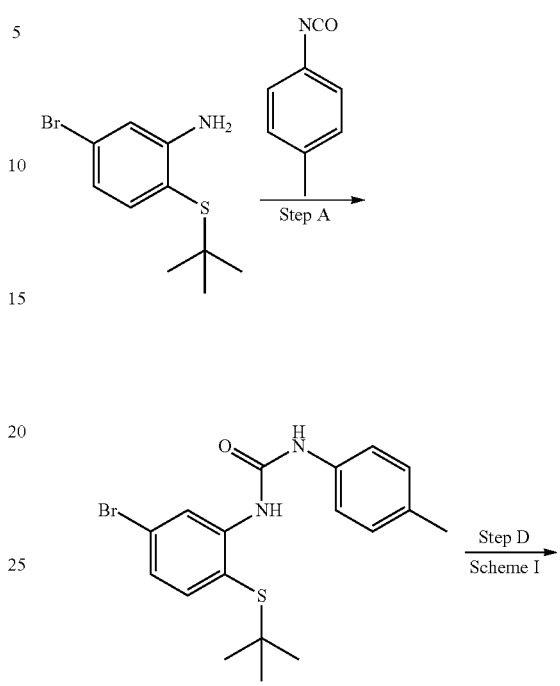

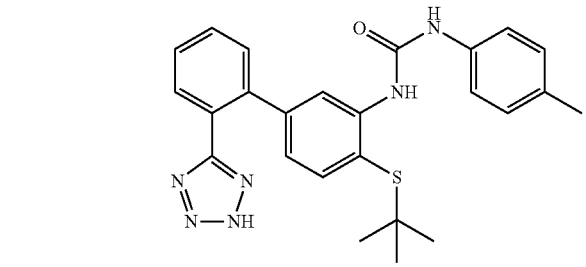 [SMILES: Cc1ccc(NC(=O)Nc2cc(-c3ccccc3-c3nn[nH]n3)ccc2SC(C)(C)C)cc1]

Example 13: 1-(4-(tert-Butylthio)-2'-(2H-tetrazol-5-yl)-[1,1'-biphenyl]-3-yl)-3-(p-tolyl)urea

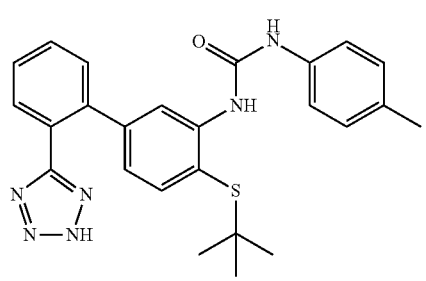

Step A

1-(5-Bromo-2-(tert-butylthio)phenyl)-3-(p-tolyl)urea

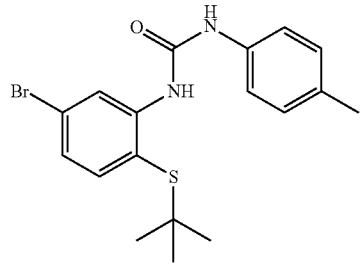 [SMILES: Cc1ccc(NC(=O)Nc2cc(Br)ccc2SC(C)(C)C)cc1]

To a solution of 5-bromo-2-(tert-butylthio)aniline (200 mg, 0.715 mmol) in tetrahydrofuran (3 mL) was added 1-isocyanato-4-methylbenzene (143 mg, 1.072 mmol) and DIEA (0.2 mL). After 2 h stirring at ambient temperature, the mixture was heated to 70° C. for 8 h. More 1-isocyanato-4-methylbenzene (143 mg, 1.072 mmol) was added. After 18 h at 70° C. the mixture was concentrated and purified on silica gel (EtOAc/hexanes 0-5%) to provide the title compound (145 mg, 0.358 mmol, 50.0% yield) as a yellow foam. LCMS (M+1)$^+$: m/z=395.3. $^1$H NMR (400 MHz, CHLOROFORM-d): δ ppm 1.10 (s, 9H), 2.38 (s, 3H), 7.10 (dd, J=8.20, 2.15 Hz, 1H), 7.18-7.37 (m, 6H), 8.31 (s, 1H), 8.64 (d, J=2.15 Hz, 1H).

Step B

1-(4-(tert-Butylthio)-2'-(2H-tetrazol-5-yl)-[1,1'-biphenyl]-3-yl)-3-(p-tolyl)urea

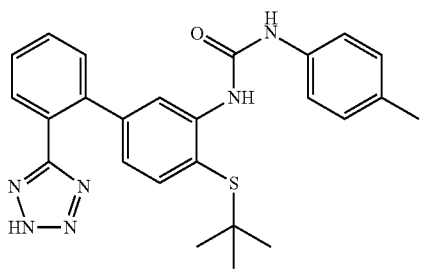 [SMILES: Cc1ccc(NC(=O)Nc2cc(-c3ccccc3-c3nn[nH]n3)ccc2SC(C)(C)C)cc1]

This compound was prepared from 1-(5-bromo-2-(tert-butylthio)phenyl)-3-(p-tolyl)urea and 2-(2H-tetrazol-5-yl)phenyl)boronic acid as described in Step D, Scheme I. LCMS (M+1)$^+$: m/z=459.4. $^1$H NMR (400 MHz, DMSO-d$_6$): δ ppm 1.27 (s, 9H), 2.24 (s, 3H), 6.61 (dd, J=7.87, 1.10 Hz, 1H), 7.09 (d, J=8.24 Hz, 2H), 7.29-7.39 (m, 3H), 7.61 (t, J=6.87 Hz, 2H), 7.66-7.75 (m, 2H), 8.18 (s, 1H), 8.50 (s, 1H), 9.61 (s, 1H).

Example 14: 4'-(tert-Butylthio)-3'-(3-(p-tolyl)ureido)-[1,1'-biphenyl]-2-carboxylic Acid

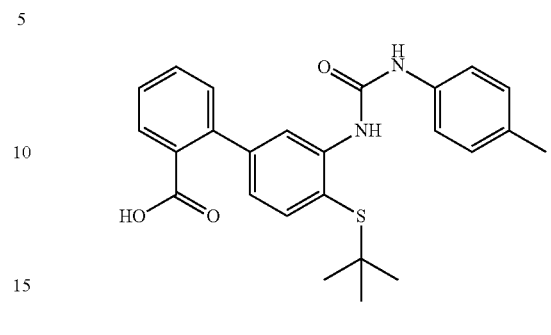

This compound was prepared from 2-boronobenzoic acid following the procedure described in Scheme III. LCMS (M+1)$^+$: m/z=435.4. $^1$H NMR (400 MHz, DMSO-d$_6$): δ ppm 1.30 (s, 9H), 2.24 (s, 3H), 6.95 (dd, J=7.87, 2.01 Hz, 1H), 7.09 (d, J=8.24 Hz, 2H), 7.36 (d, J=8.42 Hz, 2H), 7.42 (d, J=7.69 Hz, 1H), 7.45-7.52 (m, 2H), 7.56-7.64 (m, 1H), 7.74 (d, J=7.69 Hz, 1H), 8.32 (d, J=1.83 Hz, 1H), 8.55 (s, 1H), 9.63 (s, 1H).

Scheme IV: Synthesis of N-(4-(phenylsulfonyl)-2'-(2H-tetrazol-5-yl)-[1,1'-biphenyl]-3-yl)-2-(p-tolyl)acetamide

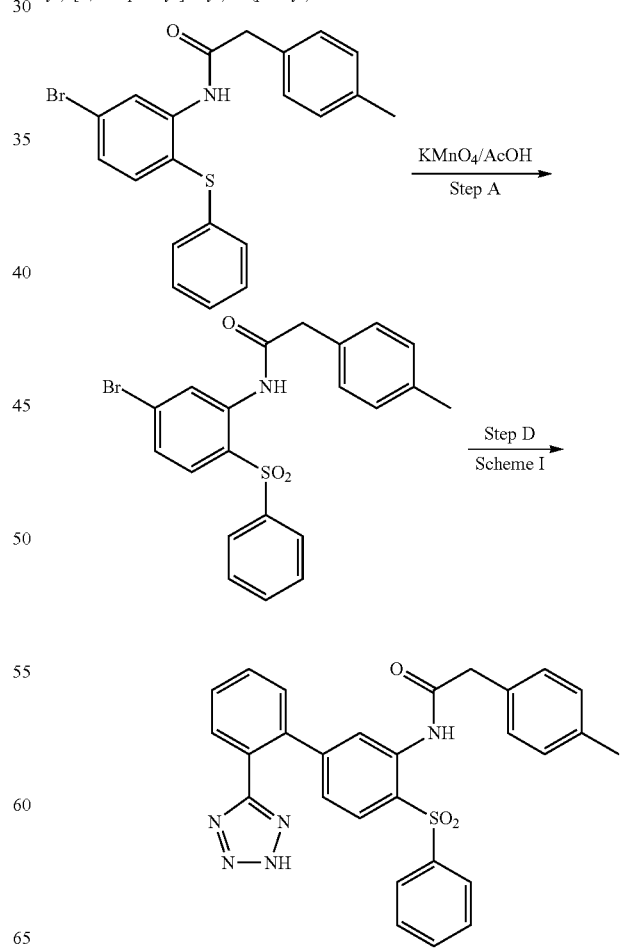

Example 15: N-(4-(phenylsulfonyl)-2'-(2H-tetrazol-5-yl)-[1,1'-biphenyl]-3-yl)-2-(p-tolyl)acetamide

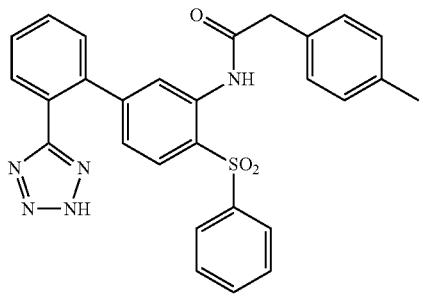 [SMILES: Cc1ccc(CC(=O)Nc2cc(-c3ccccc3-c3nn[nH]n3)ccc2S(=O)(=O)c2ccccc2)cc1]

Step A

N-(5-bromo-2-(phenylsulfonyl)phenyl)-2-(p-tolyl)acetamide

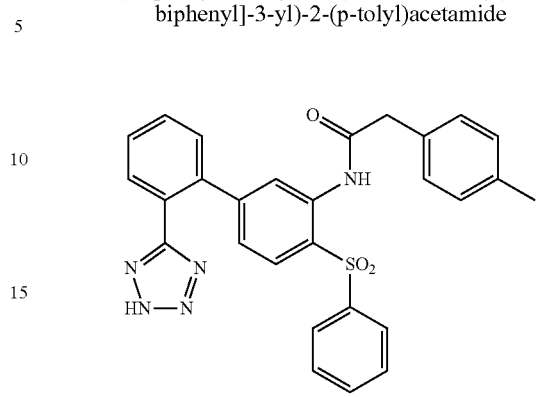

To a solution of N-(5-bromo-2-(phenylthio)phenyl)-2-(p-tolyl)acetamide (78 mg, 0.165 mmol) (synthesized from 4-bromo-1-fluoro-2-nitrobenzene and thiophenol following Steps A-C described for Scheme I) in acetic acid (1.00 mL)/dichloromethane (0.5 mL) was added dropwise a solution of potassium permanganate (867 mg, 0.165 mmol) (3%/water) and the mixture was stirred at ambient temperature for 18 h. More potassium permanganate (867 mg, 0.165 mmol) (3%/water) was added and stirring continued for 2 h. The mixture was diluted with EtOAc and water and solid NaHCO$_3$ was carefully added. The organic phase was dried (Na$_2$SO$_4$), concentrated and purified on silica gel (EtOAc/hexanes 0-5-10%) to provide the title compound (60 mg, 0.132 mmol, 80% yield) as an off-white solid. LCMS (M+1)$^+$: m/z=446.1. $^1$H NMR (400 MHz, CHLOROFORM-d): δ ppm 2.39 (s, 3H), 3.73 (s, 2H), 7.27-7.42 (m, 10H), 7.49-7.58 (m, 1H), 7.81 (d, J=8.53 Hz, 1H), 8.77 (d, J=1.79 Hz, 1H).

Step B

N-(4-(phenylsulfonyl)-2'-(2H-tetrazol-5-yl)-[1,1'-biphenyl]-3-yl)-2-(p-tolyl)acetamide This compound was obtained from N-(5-Bromo-2-(phenylsulfonyl)phenyl)-2-(p-tolyl)acetamide and (2-(2H-tetrazol-5-yl)phenyl)boronic acid as described in Step D, Scheme I. LCMS: (M+1)$^+$: m/z=510.3. $^1$H NMR (400 MHz, DMSO-d$_6$): δ ppm 2.32 (s, 3H), 3.71 (s, 2H), 7.04 (d, J=8.56 Hz, 1H), 7.22 (s, 4H), 7.53 (t, J=7.69 Hz, 3H), 7.59-7.79 (m, 6H), 7.89-8.00 (m, 2H), 9.56 (s, 1H).

Scheme V: Synthesis of N-(4-(tert-butylthio)-2'-(2H-tetrazol-5-yl)-[1,1'-biphenyl]-3-yl)-2-(2,4-difluorophenyl)acetamide

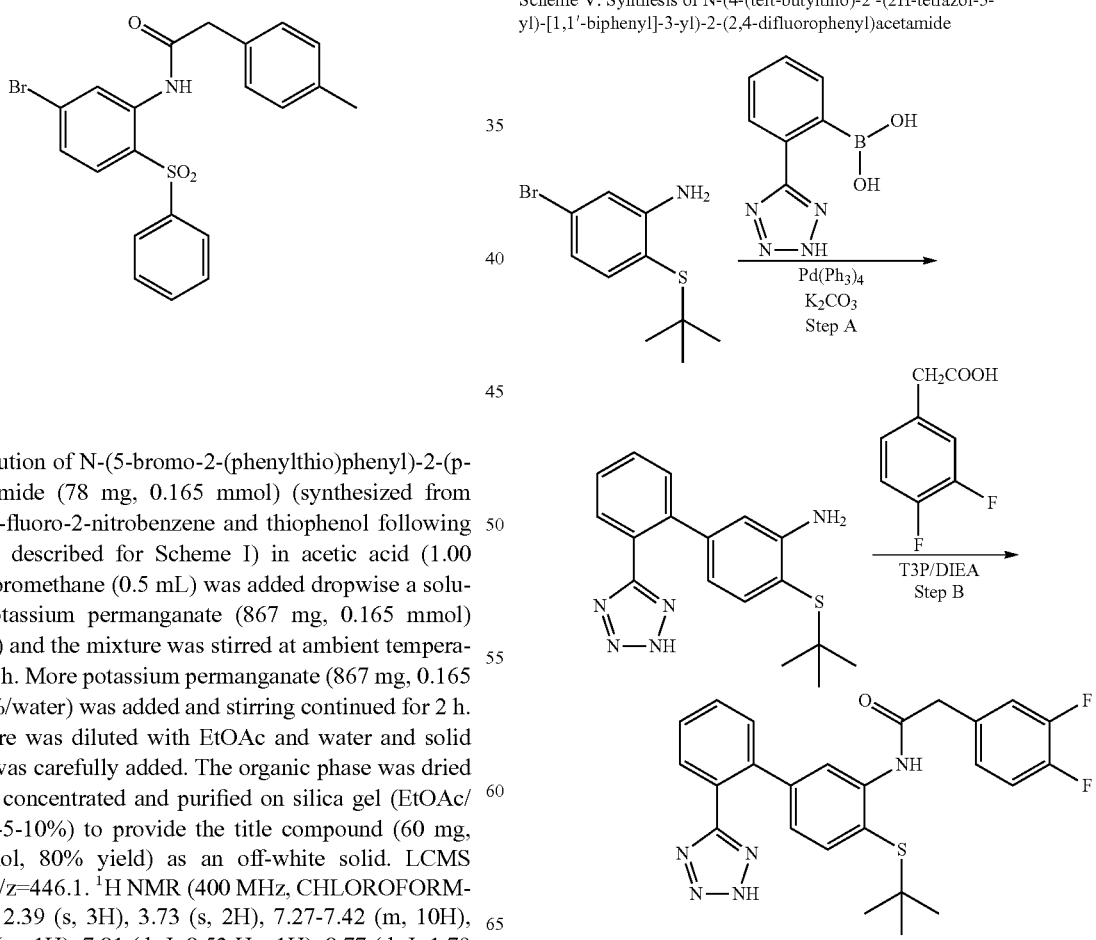

Example 16: (N-(4-(tert-butylthio)-2'-(2H-tetrazol-5-yl)-[1,1'-biphenyl]-3-yl)-2-(2,4-difluorophenyl)acetamide

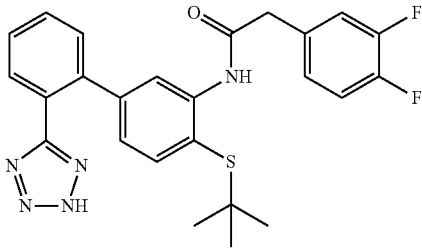 [SMILES: CC(C)(C)Sc1ccc(-c2ccccc2-c2nn[nH]n2)cc1NC(=O)Cc1ccc(F)c(F)c1]

Step A 4-(tert-Butylthio)-2'-(2H-tetrazol-5-yl)-[1,1'-biphenyl]-3-amine

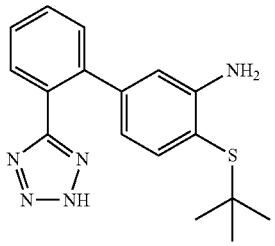 [SMILES: CC(C)(C)Sc1ccc(-c2ccccc2-c2nn[nH]n2)cc1N]

A solution of 5-bromo-2-(tert-butylthio)aniline (760 mg, 2.92 mmol) in DMF (20 mL) was degassed with a stream of nitrogen while sequentially adding (2-(2H-tetrazol-5-yl)phenyl)boronic acid (1665 mg, 8.76 mmol), potassium carbonate (1615 mg, 11.68 mmol), water (4.00 mL) and tetrakis(triphenylphosphine) palladium(0) (338 mg, 0.292 mmol) and then placed in a pre-heated oil bath at 100° C. The temperature was increased to 130° C. and the mixture was stirred under nitrogen atmosphere for 1 h. Water was added and 1N HCl/water was added to pH-5. The mixture was extracted with EtOAc and the organic phase was washed with water. The organic phase was dried (Na$_2$SO$_4$), concentrated, and purified on silica gel (MeOH/dichloromethane 0-5%) to provide the title compound (1.05 g, 2.90 mmol, 99% yield). LCMS (M+1)$^+$: m/z=326.3. $^1$H NMR (400 MHz, DMSO-d$_6$): δ ppm 1.24 (s, 9H), 6.11 (dd, J=7.81, 1.76 Hz, 1H), 6.54 (d, J=1.76 Hz, 1H), 7.08 (d, J=7.81 Hz, 1H),7.2-7.3 (m, 1H), 7.50-7.59 (m, 2H), 7.60-7.72 (m, 2H), 7.95 (s, 1H).

Step B

N-(4-(tert-butylthio)-2'-(2H-tetrazol-5-yl)-[1,1'-biphenyl]-3-yl)-2-(2,4-difluorophenyl)acetamide To a solution of 4-(tert-butylthio)-2'-(2H-tetrazol-5-yl)-[1,1'-biphenyl]-3-amine (49 mg, 0.090 mmol) in EtOAc (1.5 mL) was added 2-(2,4-difluorophenyl)acetic acid (20.22 mg, 0.117 mmol), DIEA (0.047 mL, 0.271 mmol) and 2,4,6-tripropyl-1,3,5,2,4,6-trioxatriphosphinane 2,4,6-trioxide (74.7 mg, 0.117 mmol) (50%/EtOAc) and the mixture was stirred at ambient temperature for 18 h. The mixture was washed with water (1×) and the organic phase was dried (Na$_2$SO$_4$), concentrated and purified by HPLC (RP C18, MeCN/water. 0.1% formic acid) to provide the title compound (18.7 mg, 0.039 mmol, 43.2% yield) as an off-white solid. LCMS (M+1)$^+$: m/z=480.3. $^1$H NMR (400 MHz, DMSO-d$_6$): δ ppm 1.12 (s, 9H), 3.82 (s, 2H), 6.74 (dd, J=8.01, 1.76 Hz, 1H), 7.15 (td, J=8.45, 2.25 Hz, 1H), 7.32 (td, J=9.81, 2.44 Hz, 1H), 7.38 (d, J=8.01 Hz, 1H), 7.49-7.64 (m, 3H), 7.66-7.74 (m, 2H), 8.11 (s, 1H), 9.13 (s, 1H).

Example 17: N-(4-(tert-butylthio)-2'-(2H-tetrazol-5-yl)-[1,1'-biphenyl]-3-yl)-2-cyclopropylacetamide

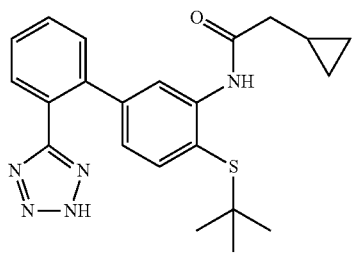 [SMILES: CC(C)(C)Sc1ccc(-c2ccccc2-c2nn[nH]n2)cc1NC(=O)CC1CC1]

This compound was prepared from 4-(tert-butylthio)-2'-(2H-tetrazol-5-yl)-[1,1'-biphenyl]-3-amine and 2-cyclopropylacetic acid as described in Step B (Scheme V). LCMS (M+1)$^+$: m/z=408.3. $^1$H NMR (400 MHz, DMSO-d$_6$): δ ppm 0.28 (d, J=4.76 Hz, 2H), 0.55-0.67 (m, 2H), 0.98-1.12 (m, 1H), 1.25 (s, 9H), 2.32 (d, J=7.14 Hz, 2H), 6.75 (d, J=8.06 Hz, 1H), 7.42 (d, J=8.06 Hz, 1H), 7.55-7.66 (m, 2H), 7.70 (d, J=7.51 Hz, 2H), 8.22 (s, 1H), 9.35 (s, 1H).

Example 18: N-(4-(tert-butylthio)-2'-(2H-tetrazol-5-yl)-[1,1'-biphenyl]-3-yl)-2-cyclohexylacetamide

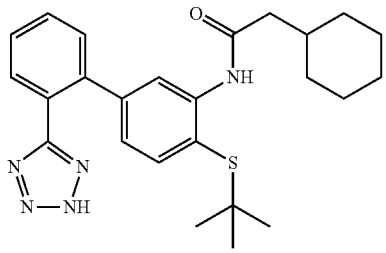 [SMILES: CC(C)(C)Sc1ccc(-c2ccccc2-c2nn[nH]n2)cc1NC(=O)CC1CCCCC1]

This compound was prepared from 4-(tert-butylthio)-2'-(2H-tetrazol-5-yl)-[1,1'-biphenyl]-3-amine and 2-cyclohexylacetic acid as described in Step B (Scheme V). LCMS (M+1)$^+$: m/z=450.3. $^1$H NMR (400 MHz, DMSO-d$_6$): δ ppm 0.90-1.05 (m, 2H), 1.07-1.30 (m, 12H), 1.54-1.83 (m, 6H), 2.27 (d, J=6.96 Hz, 2H), 6.76 (d, J=7.87 Hz, 1H), 7.41 (d, J=7.87 Hz, 1H), 7.60 (dd, J=11.08, 8.15 Hz, 2H), 7.66-7.78 (m, 2H), 8.01 (s, 1H), 9.08 (s, 1H).

Example 19: N-(4-(tert-butylthio)-2'-(2H-tetrazol-5-yl)-[1,1'-biphenyl]-3-yl)-2-(o-tolyl)acetamide

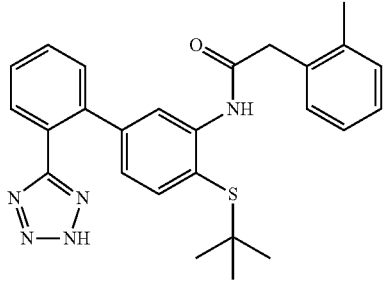 [SMILES: Cc1ccccc1CC(=O)Nc1cc(-c2ccccc2-c2nn[nH]n2)ccc1SC(C)(C)C]

This compound was prepared from 4-(tert-butylthio)-2'-(2H-tetrazol-5-yl)-[1,1'-biphenyl]-3-amine and 2-(o-tolyl)acetic acid as described in Step B (Scheme V). LCMS (M+1)$^+$: m/z=458.3. $^1$H NMR (400 MHz, DMSO-d$_6$): δ ppm 0.99 (s, 9H), 2.25 (s, 3H), 3.78 (s, 2H), 6.73 (dd, J=7.91, 1.86 Hz, 1H), 7.22-7.29 (m, 3H), 7.31-7.42 (m, 2H), 7.55-7.66 (m, 2H), 7.70 (d, J=7.42 Hz, 2H), 8.23 (d, J=1.76 Hz, 1H), 8.85 (s, 1H).

Example 20: N-(4-(tert-butylthio)-2'-(2H-tetrazol-5-yl)-[1,1'-biphenyl]-3-yl)-2-(m-tolyl)acetamide

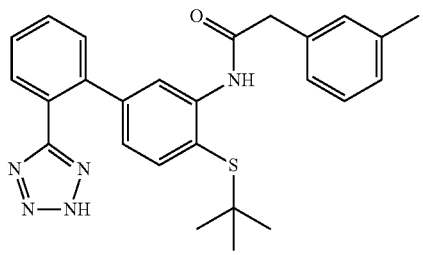 [SMILES: Cc1cccc(CC(=O)Nc2cc(-c3ccccc3-c3nn[nH]n3)ccc2SC(C)(C)C)c1]

This compound was prepared from 4-(tert-butylthio)-2'-(2H-tetrazol-5-yl)-[1,1'-biphenyl]-3-amine and 2-(m-tolyl)acetic acid as described in Step B (Scheme V). LCMS (M+1)$^+$: m/z=458.3. $^1$H NMR (400 MHz, DMSO-d$_6$): δ ppm 1.01 (s, 9H), 2.32 (s, 3H), 3.73 (s, 2H), 6.71 (dd, J=7.91, 1.86 Hz, 1H), 7.12-7.23 (m, 3H), 7.27-7.32 (m, 1H), 7.34 (d, J=8.01 Hz, 1H), 7.53-7.65 (m, 2H), 7.67-7.76 (m, 2H), 8.20 (d, J=1.56 Hz, 1H), 8.98 (s, 1H).

Example 21: N-(4-(tert-butylthio)-2'-(2H-tetrazol-5-yl)-[1,1'-biphenyl]-3-yl)-2-(3-fluoro-4-methylphenyl)acetamide

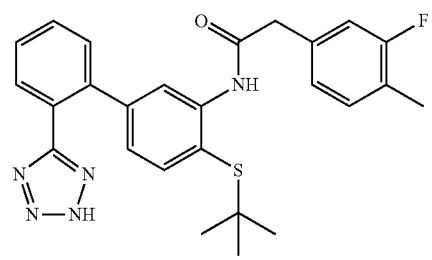 [SMILES: Cc1ccc(CC(=O)Nc2cc(-c3ccccc3-c3nn[nH]n3)ccc2SC(C)(C)C)cc1F]

This compound was prepared from 4-(tert-butylthio)-2'-(2H-tetrazol-5-yl)-[1,1'-biphenyl]-3-amine and 2-(3-fluoro-4-methylphenyl)acetic acid as described in Step B (Scheme V). LCMS (M+1)$^+$: m/z=476.4. $^1$H NMR (400 MHz, DMSO-d$_6$): δ ppm 1.03 (s, 9H), 2.23 (s, 3H), 3.76 (s, 2H), 6.73 (dd, J=8.01, 1.76 Hz, 1H), 7.12 (d, J=7.62 Hz, 1H), 7.22 (d, J=10.74 Hz, 1H), 7.31 (t, J=7.91 Hz, 1H), 7.36 (d, J=8.01 Hz, 1H), 7.52-7.65 (m, 2H), 7.69 (d, J=7.42 Hz, 2H), 8.15 (d, J=1.37 Hz, 1H), 9.02 (s, 1H).

Example 22: N-(4-(tert-butylthio)-2'-(2H-tetrazol-5-yl)-[1,1'-biphenyl]-3-yl)-2-(4-methoxyphenyl)acetamide

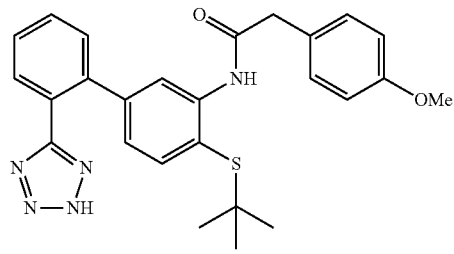 [SMILES: COc1ccc(CC(=O)Nc2cc(-c3ccccc3-c3nn[nH]n3)ccc2SC(C)(C)C)cc1]

This compound was prepared from 4-(tert-butylthio)-2'-(2H-tetrazol-5-yl)-[1,1'-biphenyl]-3-amine and 2-(4-methoxyphenyl)acetic acid as described in Step B (Scheme V). LCMS (M+1)$^+$: m/z=474.4. $^1$H NMR (400 MHz, DMSO-d$_6$): δ ppm 1.01 (s, 9H), 3.70 (s, 2H), 3.75 (s, 3H), 6.71 (dd, J=8.01, 1.76 Hz, 1H), 6.98 (d, J=8.59 Hz, 2H), 7.27-7.38 (m, 3H), 7.53-7.65 (m, 2H), 7.69 (d, J=7.42 Hz, 2H), 8.21 (d, J=1.56 Hz, 1H), 8.95 (s, 1H).

Example 23: N-(4-(tert-butylthio)-2'-(2H-tetrazol-5-yl)-[1,1'-biphenyl]-3-yl)-2-(3-fluoro-4-methoxyphenyl)acetamide

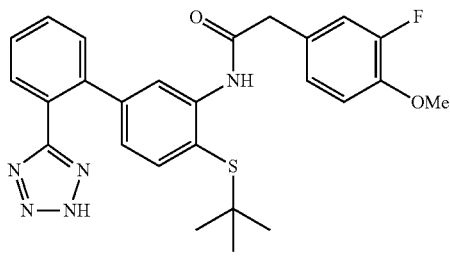 [SMILES: COc1ccc(CC(=O)Nc2cc(-c3ccccc3-c3nn[nH]n3)ccc2SC(C)(C)C)cc1F]

This compound was prepared from 4-(tert-butylthio)-2'-(2H-tetrazol-5-yl)-[1,1'-biphenyl]-3-amine and 2-(3-fluoro-4-methoxyphenyl)acetic acid as described in Step B (Scheme V). LCMS (M+1)+: m/z=492.3. $^1$H NMR (400 MHz, DMSO-$d_6$): δ ppm 1.04 (s, 9H), 3.72 (s, 2H), 3.83 (s, 3H), 6.73 (dd, J=7.91, 1.86 Hz, 1H), 7.13-7.25 (m, 2H), 7.26-7.33 (m, 1H), 7.36 (d, J=7.81 Hz, 1H), 7.53-7.65 (m, 2H), 7.70 (d, J=7.42 Hz, 2H), 8.16 (s, 1H), 9.01 (s, 1H).

Example 24: N-(4-(tert-butylthio)-2'-(2H-tetrazol-5-yl)-[1,1'-biphenyl]-3-yl)-2-(4-fluorophenyl)acetamide

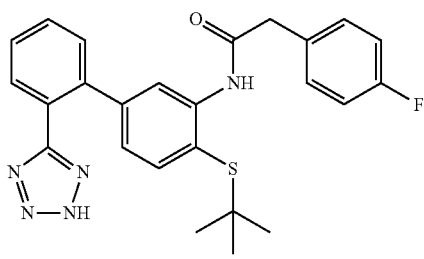 [SMILES: CC(C)(C)Sc1ccc(-c2ccccc2-c2nn[nH]n2)cc1NC(=O)Cc1ccc(F)cc1]

This compound was prepared from 4-(tert-butylthio)-2'-(2H-tetrazol-5-yl)-[1,1'-biphenyl]-3-amine and 2-(4-fluorophenyl)acetic acid as described in Step B (Scheme V). LCMS (M+1)+: m/z=462.3. $^1$H NMR (400 MHz, DMSO-$d_6$): δ ppm 1.05 (s, 9H), 3.78 (s, 2H), 6.73 (dd, J=7.91, 1.86 Hz, 1H), 7.23 (t, J=8.89 Hz, 2H), 7.36 (d, J=8.01 Hz, 1H), 7.44 (dd, J=8.50, 5.57 Hz, 2H), 7.53-7.64 (m, 2H), 7.66-7.76 (m, 2H), 8.13 (d, J=1.56 Hz, 1H), 9.04 (s, 1H).

Example 25: N-(4-(tert-butylthio)-2'-(2H-tetrazol-5-yl)-[1,1'-biphenyl]-3-yl)-2-phenylacetamide

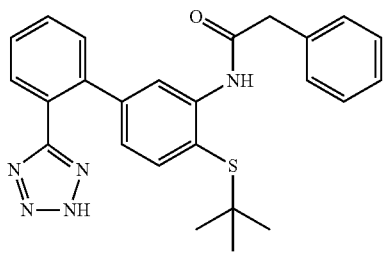 [SMILES: CC(C)(C)Sc1ccc(-c2ccccc2-c2nn[nH]n2)cc1NC(=O)Cc1ccccc1]

This compound was prepared from 4-(tert-butylthio)-2'-(2H-tetrazol-5-yl)-[1,1'-biphenyl]-3-amine and 2-phenylacetic acid as described in Step B (Scheme V). LCMS (M+1)+: m/z=444.3. $^1$H NMR (400 MHz, DMSO-$d_6$): δ ppm 1.02 (s, 9H), 3.78 (s, 2H), 6.72 (dd, J=8.01, 1.76 Hz, 1H), 7.35 (d, J=8.01 Hz, 2H), 7.37-7.46 (m, 4H), 7.54-7.65 (m, 2H), 7.69 (d, J=7.42 Hz, 2H), 8.17 (s, 1H), 9.02 (s, 1H).

Example 26: N-(4-(tert-butylthio)-2'-(2H-tetrazol-5-yl)-[1,1'-biphenyl]-3-yl)-2-(5-methylpyridin-2-yl)acetamide

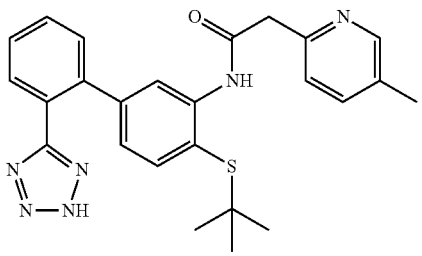 [SMILES: Cc1ccc(CC(=O)Nc2cc(-c3ccccc3-c3nn[nH]n3)ccc2SC(C)(C)C)nc1]

This compound was prepared from 4-(tert-butylthio)-2'-(2H-tetrazol-5-yl)-[1,1'-biphenyl]-3-amine and 2-(5-methylpyridin-2-yl)acetic acid as described in Step B (Scheme V). LCMS (M+1)+: m/z=459.4. $^1$H NMR (400 MHz, DMSO-$d_6$): δ ppm 1.10 (s, 9H), 2.33 (s, 3H), 3.91 (s, 2H), 6.74 (d, J=8.01 Hz, 1H), 7.34-7.46 (m, 2H), 7.60 (dd, J=18.36, 7.23 Hz, 2H), 7.66-7.80 (m, 3H), 8.21 (s, 1H), 8.53 (s, 1H), 9.91 (s, 1H).

Example 27: N-(4-(tert-butylthio)-2'-(2H-tetrazol-5-yl)-[1,1'-biphenyl]-3-yl)-2-(4-isopropylphenyl)acetamide

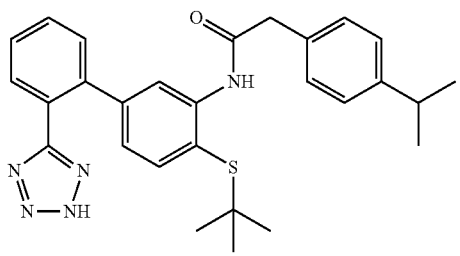 [SMILES: CC(C)c1ccc(CC(=O)Nc2cc(-c3ccccc3-c3nn[nH]n3)ccc2SC(C)(C)C)cc1]

This compound was prepared from 4-(tert-butylthio)-2'-(2H-tetrazol-5-yl)-[1,1'-biphenyl]-3-amine and 2-(4-isopropylphenyl)acetic acid as described in Step B (Scheme V). LCMS (M+1)+: m/z=486.4. $^1$H NMR (400 MHz, DMSO-$d_6$): δ ppm 0.98 (s, 9H), 1.20 (d, J=6.84 Hz, 6H), 2.89 (quin, J=6.84 Hz, 1H), 3.72 (s, 2H), 6.71 (d, J=7.81 Hz, 1H), 7.23-7.38 (m, 5H), 7.52-7.65 (m, 2H), 7.66-7.77 (m, 2H), 8.21 (s, 1H), 8.96 (s, 1H).

Example 28: N-(4-(tert-butylsulfonyl)-2'-(2H-tetrazol-5-yl)-[1,1'-biphenyl]-3-yl)-2-(4-isopropylphenyl)acetamide

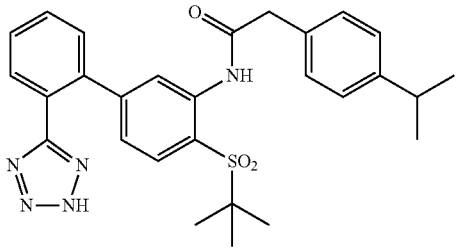 [SMILES: CC(C)c1ccc(CC(=O)Nc2cc(-c3ccccc3-c3nn[nH]n3)ccc2S(=O)(=O)C(C)(C)C)cc1]

This compound was prepared from N-(4-(tert-butylsulfonyl)-2'-(2H-tetrazol-5-yl)-[1,1'-biphenyl]-3-yl)-2-(4-isopropylphenyl)acetamide following the procedure described in Example 2 and 3. LCMS (M+1)$^+$: m/z 518.4. $^1$H NMR (400 MHz, DMSO-d$_6$): δ ppm 1.03 (s, 9H), 1.20 (d, J=6.84 Hz, 6H), 2.75-2.90 (m, 1H), 3.70 (s, 2H), 6.95 (d, J=8.40 Hz, 1H), 7.24 (s, 4H), 7.61 (d, J=8.01 Hz, 2H), 7.67 (d, J=7.42 Hz, 1H), 7.75 (dd, J=19.14, 7.42 Hz, 2H), 8.34 (s, 1H), 9.78 (s, 1H).

Example 29: tert-Butyl 4-(2-((4-(tert-butylthio)-2'-(2H-tetrazol-5-[1,1'-biphenyl]-3-yl)amino)-2-oxoethyl)piperidine-1-carboxylate

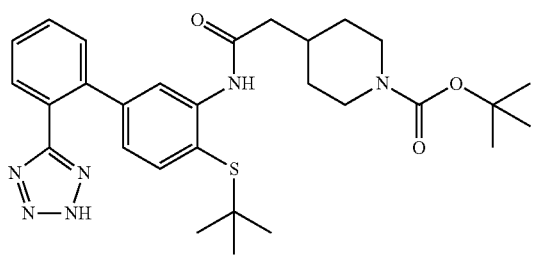 [SMILES: CC(C)(C)OC(=O)N1CCC(CC(=O)Nc2cc(-c3ccccc3-c3nn[nH]n3)ccc2SC(C)(C)C)CC1]

This compound was prepared from 4-(tert-butylthio)-2'-(2H-tetrazol-5-yl)-[1,1'-biphenyl]-3-amine and 2-(1-(tert-butoxycarbonyl)piperidin-4-yl)acetic acid as described in Step B (Scheme V). LCMS (M+1)$^+$: m/z=551.4. $^1$H NMR (400 MHz, DMSO-d$_6$): δ ppm 0.98-1.14 (m, 2H), 1.23 (s, 9H), 1.35 (s, 9H), 1.62 (d, J=11.91 Hz, 2H), 1.91 (d, J=12.30 Hz, 1H), 2.34 (d, J=7.03 Hz, 2H), 2.45-2.55 (m, 2H), 3.89 (br. s., 2H), 6.78 (dd, J=7.81, 1.76 Hz, 1H), 7.42 (d, J=7.81 Hz, 1H), 7.61 (dd, J=9.67, 7.91 Hz, 2H), 7.67-7.77 (m, 2H), 7.95 (s, 1H), 9.15 (s, 1H), 12.09 (s, 1H).

Example 30: N-(4-(tert-butylthio)-2'-(2H-tetrazol-5-yl)-[1,1'-biphenyl]-3-yl)-2-(piperidin-4-yl)acetamide Hydrochloride

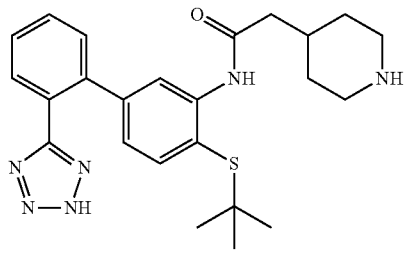 [SMILES: CC(C)(C)Sc1ccc(-c2ccccc2-c2nn[nH]n2)cc1NC(=O)CC1CCNCC1]

To tert-butyl 4-(2-((4-(tert-butylthio)-2'-(2H-tetrazol-5-yl)-[1,1'-biphenyl]-3-yl)amino)-2-oxoethyl)piperidine-1-carboxylate (26 mg, 0.042 mmol) (Example 29) was added HCl (0.499 mL, 1.997 mmol) (4M/dioxane) and the mixture was stirred at ambient temperature for 30 min. The mixture was concentrated and coevaporated with MeCN The residue was dissolved in dichloromethane and excess hexanes was added. The mixture was concentrated, dried to provide the title compound as the hydrochloride salt (21 mg, 0.042 mmol, 98% yield) as a yellowish solid. LCMS (M+1)$^+$: m/z=451.4. $^1$H NMR (400 MHz, DMSO-d$_6$): δ ppm 1.23 (s, 9H), 1.24-1.26 (m, 1H), 1.37 (d, J=12.69 Hz, 2H), 1.79 (d, J=13.87 Hz, 2H), 2.39 (d, J=7.03 Hz, 2H), 2.88 (d, J=10.16 Hz, 2H), 3.25 (d, J=12.30 Hz, 2H), 6.84 (dd, J=7.91, 1.86 Hz, 1H), 7.44 (d, J=8.01 Hz, 1H), 7.55-7.66 (m, 2H), 7.66-7.77 (m, 2H), 7.87 (s, 1H), 9.21 (s, 1H).

Example 31: 2-(1-Acetylpiperidin-4-yl)-N-(4-(tert-butylthio)-2'-(2H-tetrazol-5-yl)-[1,1'-biphenyl]-3-yl)acetamide

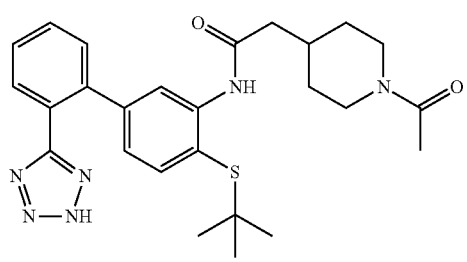 [SMILES: CC(=O)N1CCC(CC(=O)Nc2cc(-c3ccccc3-c3nn[nH]n3)ccc2SC(C)(C)C)CC1]

To a suspension of N-(4-(tert-butylthio)-2'-(2H-tetrazol-5-yl)-[1,1'-biphenyl]-3-yl)-2-(piperidin-4-yl)acetamide (13 mg, 0.017 mmol) (Example 30) in dichloromethane (0.5 mL) was added TEA (0.014 mL, 0.104 mmol) followed by acetic anhydride (1.633 µl, 0.017 mmol) and the mixture was stirred at ambient temperature for 15 min. The mixture was concentrated, dissolved in MeOH and purified by HPLC (RP C18, MeCN/water. 0.1% formic acid) to provide the title compound (3.3 mg, 6.43 µmol, 37.1% yield) as a yellow solid. LCMS (M+1)$^+$: m/z=493.4. $^1$H NMR (400 MHz, DMSO-d$_6$): δ ppm 0.92-1.18 (m, 2H), 1.23 (s, 9H), 1.66 (t, J=15.04 Hz, 2H), 1.98 (s, 4H), 2.35 (d, J=7.23 Hz, 2H), 2.55-2.60 (m, 1H), 3.00 (t, J=11.72 Hz, 1H), 3.78 (d, J=13.47 Hz, 1H), 4.33 (d, J=13.28 Hz, 1H), 6.79 (dd, J=8.01, 1.76 Hz, 1H), 7.42 (d, J=7.81 Hz, 1H), 7.55-7.65 (m, 2H), 7.66-7.77 (m, 2H), 7.95 (s, 1H), 9.15 (s, 1H).

Example 32: N-(4-(tert-butylthio)-2'-(2H-tetrazol-5-yl)-[1,1'-biphenyl]-3-yl)-2-(1-(methylsulfonyl)piperidin-4-yl)acetamide

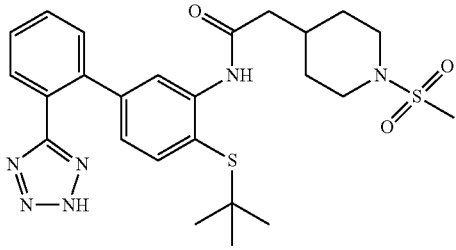 [SMILES: CC(C)(C)Sc1ccc(-c2ccccc2-c2nn[nH]n2)cc1NC(=O)CC1CCN(S(C)(=O)=O)CC1]

To a suspension of N-(4-(tert-butylthio)-2'-(2H-tetrazol-5-yl)-[1,1'-biphenyl]-3-yl)-2-(piperidin-4-yl)acetamide (63 mg, 0.084 mmol) (Example 30) in dichloromethane (1.5 mL) was added TEA (0.058 mL, 0.419 mmol) followed by methanesulfonyl chloride (0.013 mL, 0.168 mmol) and the mixture was stirred at ambient temperature for 15 min. The mixture was concentrated, dissolved in MeOH and purified by HPLC (RP C18, MeCN/water. 0.1% formic acid) to provide the title compound (15.7 mg, 0.030 mmol, 35.4% yield). LCMS (M+1)$^+$: m/z=529.4. $^1$H NMR (400 MHz, DMSO-d$_6$): δ ppm 1.23 (s, 9H), 1.23-1.33 (m, 3H), 1.75 (d, J=13.08 Hz, 2H), 2.39 (d, J=7.03 Hz, 2H), 2.63-2.77 (m, 2H), 2.85 (s, 3H), 3.53 (d, J=11.72 Hz, 2H), 6.79 (dd, J=7.91, 1.86 Hz, 1H), 7.43 (d, J=7.81 Hz, 1H), 7.61 (t, J=8.49 Hz, 2H), 7.70 (dd, J=7.03, 4.49 Hz, 2H), 7.94 (s, 1H), 9.18 (s, 1H).

Example 33: N-(4-(tert-butylthio)-2'-(2H-tetrazol-5-yl)-[1,1'-biphenyl]-3-yl)-2-methoxyacetamide

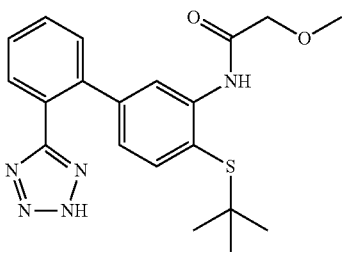 [SMILES: COCC(=O)Nc1cc(-c2ccccc2-c2nn[nH]n2)ccc1SC(C)(C)C]

This compound was prepared from 4-(tert-butylthio)-2'-(2H-tetrazol-5-yl)-[1,1'-biphenyl]-3-amine and 2-methoxyacetic acid as described in Step B (Scheme V). LCMS (M+1)$^+$: m/z=398.3. $^1$H NMR (400 MHz, DMSO-d$_6$): δ ppm 1.26 (s, 9H), 3.47 (s, 3H), 4.03 (s, 2H), 6.79 (dd, J=7.91, 1.86 Hz, 1H), 7.45 (d, J=8.01 Hz, 1H), 7.56-7.66 (m, 2H), 7.67-7.77 (m, 2H), 8.30 (d, J=1.76 Hz, 1H), 9.83 (s, 1H).

Example 34: N-(4-(tert-butylthio)-2'-(2H-tetrazol-5-yl)-[1,1'-biphenyl]-3-yl)-2-(4-chlorophenyl)acetamide

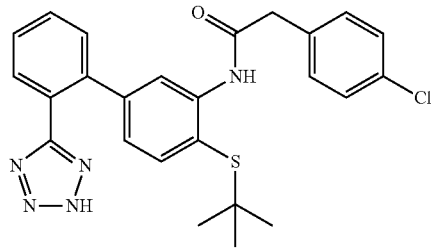

This compound was prepared from 4-(tert-butylthio)-2'-(2H-tetrazol-5-yl)-[1,1'-biphenyl]-3-amine and 2-(4-chlorophenyl)acetic acid as described in Step B (Scheme V). LCMS (M+1)$^+$: m/z=478.4. $^1$H NMR (400 MHz, DMSO-d$_6$): δ ppm 1.05 (s, 9H), 3.79 (s, 2H), 6.74 (d, J=7.62 Hz, 1H), 7.19 (d, J=8.20 Hz, 1H), 7.37 (dd, J=8.20, 2.15 Hz, 2H), 7.40-7.50 (m, 4H), 7.54-7.65 (m, 1H), 7.70 (d, J=7.42 Hz, 1H), 8.11 (s, 1H), 9.05 (s, 1H).

Example 35: p-Tolyl (4-(tert-butylthio)-2'-(2H-tetrazol-5-yl)-[1,1'-biphenyl]-3-yl)carbamate

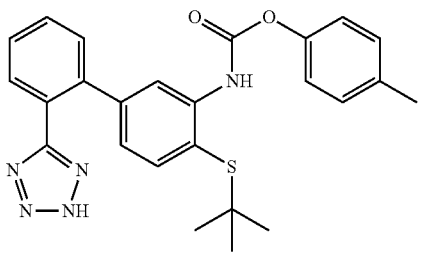

To a solution of 4-(tert-butylthio)-2'-(2H-tetrazol-5-yl)-[1,1'-biphenyl]-3-amine (47 mg, 0.140 mmol) in dichloromethane (2 mL) was added TEA (0.064 mL, 0.462 mmol) and p-tolyl chloroformate (0.023 mL, 0.154 mmol) and the mixture was stirred at ambient temperature. After 1.5 h, more p-tolyl chloroformate (0.023 mL, 0.154 mmol) was added. After 18 h, the mixture was diluted with EtOAc and saturated NaHCO$_3$/water and stirred at ambient temperature for 40 min; 1N HCl/water was added and the mixture was extracted with EtOAc. The organic phase was dried (Na$_2$SO$_4$), concentrated and purified by HPLC (RP C18, MeCN/water. 0.1% formic acid) to provide the title compound (17.2 mg, 0.037 mmol, 26.7% yield) as an off-white solid. LCMS (M+1)$^+$: m/z=460.3. $^1$H NMR (400 MHz, DMSO-d$_6$): δ ppm 1.27 (s, 9H), 2.31 (s, 3H), 6.82 (d, J=8.06 Hz, 1H), 7.06 (d, J=8.24 Hz, 2H), 7.22 (d, J=8.24 Hz, 2H), 7.46 (d, J=7.87 Hz, 1H), 7.55-7.65 (m, 2H), 7.66-7.76 (m, 3H), 8.96 (s, 1H).

Example 36: N-(4-(tert-butylthio)-2'-(2H-tetrazol-5-yl)-[1,1'-biphenyl]-3-yl)benzamide

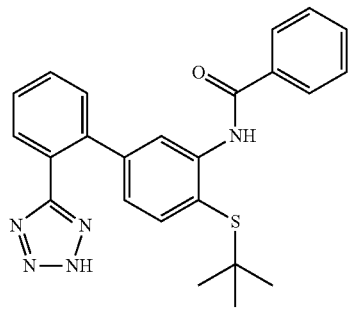 [SMILES: CC(C)(C)Sc1ccc(-c2ccccc2-c2nn[nH]n2)cc1NC(=O)c1ccccc1]

To a solution of 4-(tert-butylthio)-2'-(2H-tetrazol-5-yl)-[1,1'-biphenyl]-3-amine (49 mg, 0.146 mmol) in dichloromethane (2 mL) was added TEA (0.067 mL, 0.482 mmol) and benzoyl chloride (0.017 mL, 0.146 mmol) and the mixture was stirred at ambient temperature. After 1.5 h, more benzoyl chloride (0.017 mL, 0.146 mmol) was added. After 18 h, the mixture was diluted with EtOAc and saturated NaHCO$_3$/water was added followed by 1M NaOH/water. After 1 h at ambient temperature the mixture was diluted with 1N HCl/water and extracted with EtOAc. The organic phase was concentrated and purified by HPLC (RP C18, MeCN/water, 0.1% formic acid) to provide the title compound (23.7 mg, 0.055 mmol, 37.8% yield) as an off-white solid. LCMS (M+1)$^+$: m/z=430.3. $^1$H NMR (400 MHz, DMSO-d$_6$): δ ppm 1.23 (s, 9H), 6.86 (d, J=7.87 Hz, 1H), 7.50 (d, J=8.06 Hz, 1H), 7.57-7.68 (m, 5H), 7.72 (d, J=7.87 Hz, 2H), 7.94 (d, J=7.33 Hz, 2H), 8.15 (s, 1H), 9.83 (s, 1H).

Example 37: N-(4-(tert-butylthio)-2'-(2H-tetrazol-5-yl)-[1,1'-biphenyl]-3-yl)-3-(p-tolyl)propanamide

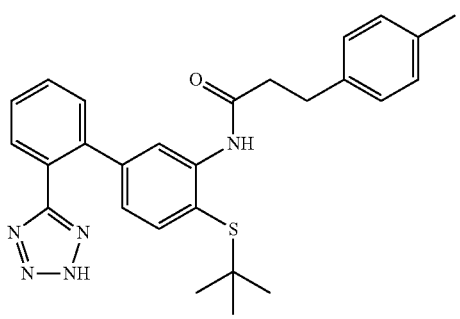 [SMILES: Cc1ccc(CCC(=O)Nc2cc(-c3ccccc3-c3nn[nH]n3)ccc2SC(C)(C)C)cc1]

This compound was prepared from 4-(tert-butylthio)-2'-(2H-tetrazol-5-yl)-[1,1'-biphenyl]-3-amine and 3-(p-tolyl)propanoic acid as described in Step B (Scheme V). LCMS (M+1)$^+$: m/z=472.4. $^1$H NMR (400 MHz, DMSO-d$_6$): δ ppm 1.17 (s, 9H), 2.25 (s, 3H), 2.66-2.75 (m, 2H), 2.78-2.89 (m, 2H), 6.75 (dd, J=7.97, 1.56 Hz, 1H), 7.03-7.10 (m, 2H), 7.10-7.16 (m, 2H), 7.39 (d, J=8.06 Hz, 1H), 7.59 (dd, J=17.31, 7.60 Hz, 2H), 7.69 (d, J=7.51 Hz, 2H), 8.02 (s, 1H), 9.11 (s, 1H).

Example 38: 2-(Benzo[d][1,3]dioxol-5-yl)-N-(4-(tert-butylthio)-2'-(2H-tetrazol-5-yl)-[1,1'-biphenyl]-3-yl)acetamide

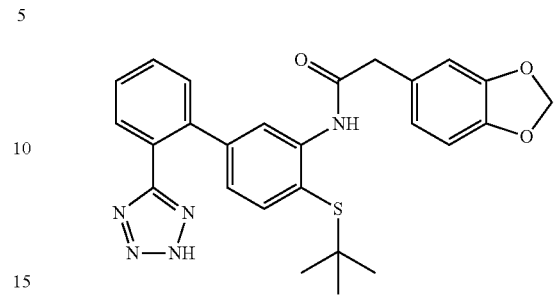

This compound was prepared from 4-(tert-butylthio)-2'-(2H-tetrazol-5-yl)-[1,1'-biphenyl]-3-amine and 2-(benzo[d][1,3]dioxol-5-yl)acetic acid as described in Step B (Scheme V). LCMS (M+1)$^+$: m/z=488.3. $^1$H NMR (400 MHz, DMSO-d$_6$): δ ppm 1.05 (s, 9H), 3.68 (s, 2H), 6.02 (s, 2H), 6.72 (d, J=8.01 Hz, 1H), 6.82-6.90 (m, 1H), 6.92-6.97 (m, 1H), 7.00 (s, 1H), 7.35 (d, J=8.01 Hz, 1H), 7.52-7.65 (m, 2H), 7.70 (d, J=7.42 Hz, 2H), 8.20 (s, 1H), 8.99 (s, 1H).

Example 39: N-(4-(tert-butylthio)-2'-(2H-tetrazol-5-yl)-[1,1'-biphenyl]-3-yl)-2-mesitylacetamide

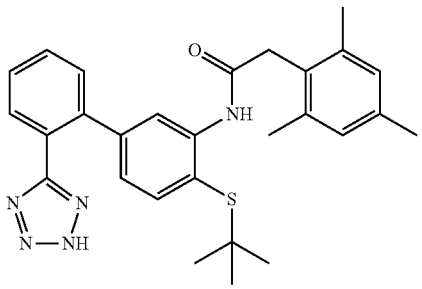 [SMILES: Cc1cc(C)c(CC(=O)Nc2cc(-c3ccccc3-c3nn[nH]n3)ccc2SC(C)(C)C)c(C)c1]

This compound was prepared from 4-(tert-butylthio)-2'-(2H-tetrazol-5-yl)-[1,1'-biphenyl]-3-amine and 2-mesitylacetic as described in Step B (Scheme V). LCMS (M+1)$^+$: m/z=486.4. $^1$H NMR (400 MHz, DMSO-d$_6$): δ ppm 0.93 (s, 9H), 2.25 (s, 9H), 3.72 (s, 2H), 6.69 (dd, J=7.81, 1.76 Hz, 1H), 6.97 (s, 2H), 7.31 (d, J=7.81 Hz, 1H), 7.54-7.65 (m, 2H), 7.70 (d, J=7.42 Hz, 2H), 8.30 (d, J=1.56 Hz, 1H), 8.72 (s, 1H).

Example 40: 2-(4-Bromophenyl)-N-(4-(tert-butylthio)-2'-(2H-tetrazol-5-yl)-[1,1'-biphenyl]-3-yl)acetamide

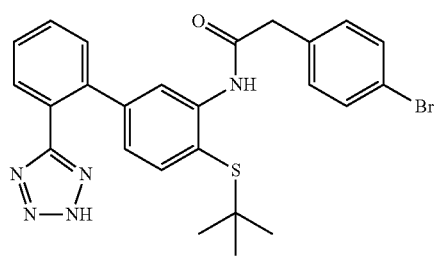 [SMILES: CC(C)(C)Sc1ccc(-c2ccccc2-c2nn[nH]n2)cc1NC(=O)Cc1ccc(Br)cc1]

This compound was prepared from 4-(tert-butylthio)-2'-(2H-tetrazol-5-yl)-[1,1'-biphenyl]-3-amine and 2-(4-bromophenyl)acetic acid as described in Step B (Scheme V). LCMS (M+1)+: m/z=524.2. 1H NMR (400 MHz, DMSO-d6): δ ppm 1.05 (s, 9H), 3.78 (s, 2H), 6.74 (dd, J=7.91, 1.86 Hz, 1H), 7.36 (dd, J=8.20, 2.54 Hz, 3H), 7.53-7.65 (m, 4H), 7.67-7.77 (m, 2H), 8.11 (d, J=1.56 Hz, 1H), 9.04 (s, 1H).

Example 41: N-(4-(tert-butylthio)-2'-(2H-tetrazol-5-yl)-[1,1'-biphenyl]-3-yl)-2-(2,4-dimethylphenyl)acetamide

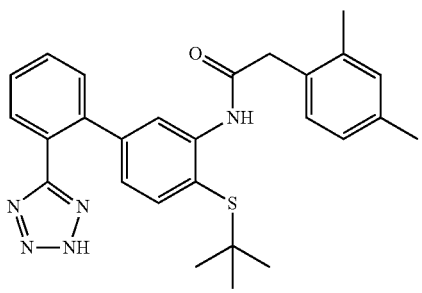

This compound was prepared from 4-(tert-butylthio)-2'-(2H-tetrazol-5-yl)-[1,1'-biphenyl]-3-amine and 2-(2,4-dimethylphenyl)acetic acid as described in Step B (Scheme V). LCMS (M+1)+: m/z=472.4. 1H NMR (400 MHz, DMSO-d6): δ ppm 0.97 (s, 9H), 2.21 (s, 3H), 2.28 (s, 3H), 3.72 (s, 2H), 6.72 (d, J=7.87 Hz, 1H), 7.03-7.14 (m, 2H), 7.25 (d, J=7.51 Hz, 1H), 7.33 (d, J=7.87 Hz, 1H), 7.59 (dd, J=17.58, 7.51 Hz, 2H), 7.69 (d, J=7.51 Hz, 2H), 8.25 (s, 1H), 8.79 (s, 1H).

Example 42: N-(4-(tert-butylthio)-2'-(2H-tetrazol-5-yl)-[1,1'-biphenyl]-3-yl)-3-chloro-1,2,4-thiadiazol-5-amine

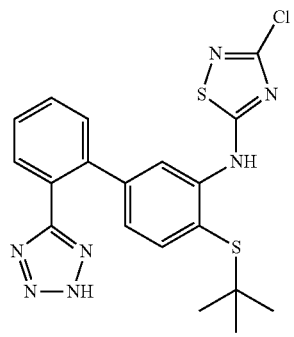 [SMILES: CC(C)(C)Sc1ccc(-c2ccccc2-c2nn[nH]n2)cc1Nc1nc(Cl)ns1]

A solution of 4-(tert-butylthio)-2'-(2H-tetrazol-5-yl)-[1,1'-biphenyl]-3-amine (113 mg, 0.233 mmol) and 3,5-dichloro-1,2,4-thiadiazole (54.1 mg, 0.349 mmol) in DMSO (1 mL) was heated to 90° C. for 3 h. The mixture was purified by HPLC (C18 RP, MeCN/water 10-100%, 0.05% TFA) to provide the title compound (12 mg, 0.026 mmol, 11.39% yield) as a tan solid. LCMS (M+H)+: m/z=444.2. 1H NMR (400 MHz, DMSO-d6): δ ppm 1.23 (s, 9H), 6.83 (d, J=7.42 Hz, 1H), 7.48 (d, J=7.81 Hz, 1H), 7.65 (d, J=6.64 Hz, 2H), 7.73 (d, J=7.23 Hz, 2H), 8.15 (s, 1H), 10.79 (s, 1H).

Example 43: N-(4-(tert-butylthio)-2'-(2H-tetrazol-5-yl)-[1,1'-biphenyl]-3-yl)-3-(trifluoromethyl)-1,2,4-thiadiazol-5-amine

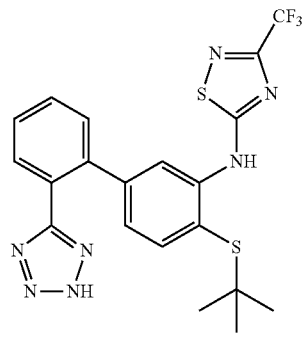 [SMILES: CC(C)(C)Sc1ccc(-c2ccccc2-c2nn[nH]n2)cc1Nc1nc(C(F)(F)F)ns1]

This compound was prepared from 4-(tert-butylthio)-2'-(2H-tetrazol-5-yl)-[1,1'-biphenyl]-3-amine and 5-chloro-3-(trifluoromethyl)-1,2,4-thiadiazole as described in Example 42 to provide the title compound. LCMS: (M+1): m/z 478.3. 1H NMR (400 MHz, DMSO-d6): δ ppm 1.24 (s, 9H) 6.80 (d, J=7.62 Hz, 1H) 7.48 (d, J=7.81 Hz, 1H) 7.59-7.68 (m, 2H) 7.74 (br. s., 2H) 8.28 (br. s., 1H) 10.95 (s, 1H).

Scheme VI: Synthesis 3-(4-(tert-butylthio)-3-(2-(p-tolyl)acetamido)phenyl)butanoic acid

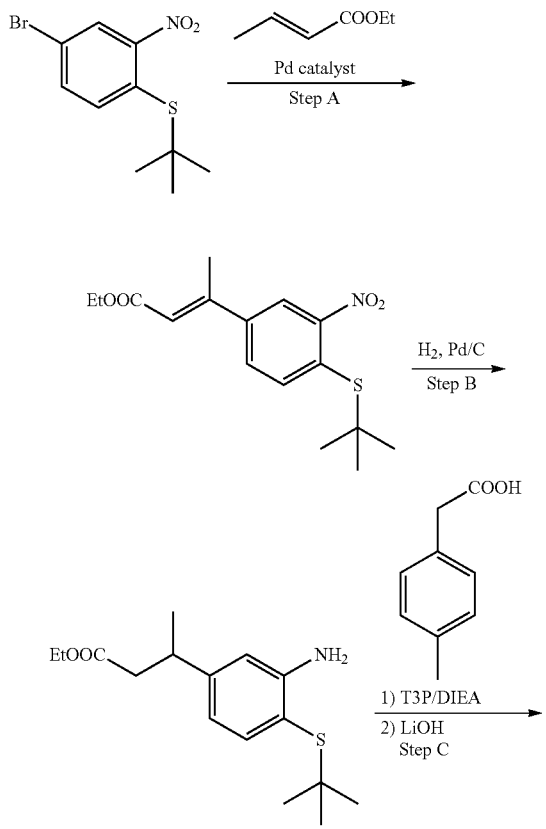

-continued

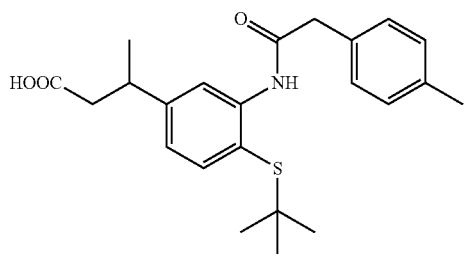

Example 44: 3-(4-(tert-Butylthio)-3-(2-(p-tolyl)acetamido)phenyl)butanoic Acid

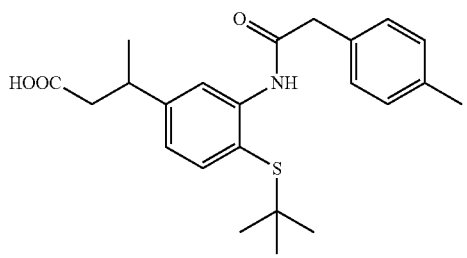 [SMILES: Cc1ccc(CC(=O)Nc2cc(C(C)CC(=O)O)ccc2SC(C)(C)C)cc1]

Step A (E)-Ethyl 3-(4-(tert-butylthio)-3-nitrophenyl)but-2-enoate

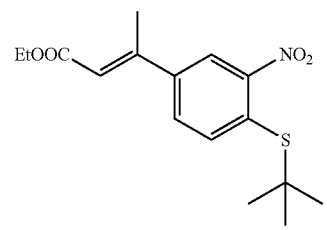 [SMILES: CCOC(=O)/C=C(\C)c1ccc(SC(C)(C)C)c([N+](=O)[O-])c1]

To a solution of 5-bromo-2-(tert-butylthio)aniline (117 mg, 0.450 mmol) in DMF (2 mL) was added tetrabutylammonium bromide (29.0 mg, 0.090 mmol), ethyl crotonate (0.113 mL, 0.899 mmol), TEA (0.175 mL, 1.259 mmol) and bis(tri-o-tolylphosphine)palladium(II) dichloride (17.67 mg, 0.022 mmol) and the mixture was degassed with a stream of nitrogen for 5 min then heated under nitrogen at 110° C. for 1 h. Water was added and the mixture was extracted with EtOAc. The organic phase was washed with water, dried (Na$_2$SO$_4$), concentrated and purified on silica gel (EtOAc/hexanes 0-5%) to provide the title compound (52.5 mg, 0.179 mmol, 39.8% yield) as a pale yellow oil. LCMS: (M+1): m/z=294.3. $^1$H NMR (400 MHz, CHLOROFORM-d): δ ppm 1.26-1.37 (m, 12H), 2.52 (d, J=0.98 Hz, 3H), 4.20 (q, J=7.03 Hz, 2H), 4.31-4.98 (m, 2H), 6.12 (d, J=1.17 Hz, 1H), 6.77 (dd, J=8.01, 1.95 Hz, 1H), 6.83 (d, J=1.76 Hz, 1H), 7.34 (d, J=8.01 Hz, 1H).

Step B

Ethyl 3-(3-amino-4-(tert-butylthio)phenyl)butanoate

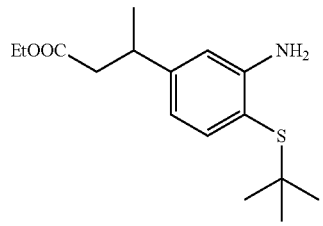 [SMILES: CCOC(=O)CC(C)c1ccc(SC(C)(C)C)c(N)c1]

To a solution of (E)-ethyl 3-(3-amino-4-(tert-butylthio)phenyl)but-2-enoate (50 mg, 0.170 mmol) in EtOH (2 mL) was added Pd—C (50 mg, 0.470 mmol) (10 wt. %, wet support, Degussa type E101 NEW) and the mixture was stirred at ambient temperature under hydrogen atmosphere for 2 h and then at 60 psi for 18 h. More Pd—C (50 mg, 0.470 mmol) was added and stirring at 60 psi of hydrogen continued for 24 h. The mixture was filtered and concentrated to provide the title compound (26.6 mg, 0.081 mmol, 47.6% yield). LCMS: (M+1): m/z=296.3. $^1$H NMR (400 MHz, CHLOROFORM-d): δ ppm 1.19 (t, J=7.05 Hz, 3H), 1.27 (d, J=7.14 Hz, 3H), 1.30 (s, 9H), 2.43-2.65 (m, 2H), 3.08-3.25 (m, 1H), 4.09 (q, J=7.14 Hz, 2H), 4.44 (br. s., 2H), 6.55 (d, J=7.87 Hz, 1H), 6.61 (d, J=1.47 Hz, 1H), 7.27 (d, J=7.87 Hz, 1H).

Step C 3-(4-(tert-Butylthio)-3-(2-(p-tolyl)acetamido)phenyl)butanoic Acid

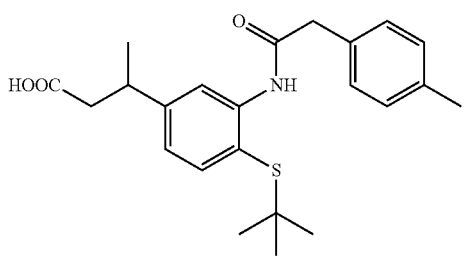 [SMILES: Cc1ccc(CC(=O)Nc2cc(C(C)CC(=O)O)ccc2SC(C)(C)C)cc1]

To a solution of ethyl 3-(3-amino-4-(tert-butylthio)phenyl)butanoate (26 mg, 0.088 mmol) in EtOAc (1 mL) was added 2-(p-tolyl)acetic acid (13.22 mg, 0.088 mmol), DIEA (0.046 mL, 0.264 mmol) and 2,4,6-tripropyl-1,3,5,2,4,6-trioxatriphosphinane 2,4,6-trioxide (61.6 mg, 0.097 mmol) (50%/EtOAc) and the mixture was stirred at ambient temperature for 18 h. More 2-(p-tolyl)acetic acid (13.22 mg, 0.088 mmol), DIEA (0.046 mL, 0.264 mmol) and 2,4,6-tripropyl-1,3,5,2,4,6-trioxatriphosphinane 2,4,6-trioxide (61.6 mg, 0.097 mmol) (50%/EtOAc) was added. After 18 h, more DIEA (0.046 mL, 0.264 mmol), 2-(p-tolyl)acetic acid (13.22 mg, 0.088 mmol) and 2,4,6-tripropyl-1,3,5,2,4,6-trioxatriphosphinane 2,4,6-trioxide (61.6 mg, 0.097 mmol) (50%/EtOAc) was added. After 24 h the mixture was diluted with EtOAc and washed with water. The organic phase was dried (Na$_2$SO$_4$), concentrate and purified on silica gel (EtOAc/hexanes 0-10%) to provide ethyl 3-(4-(tert-butylthio)-3-(2-(p-tolyl)acetamido)phenyl)butanoate (15 mg, 0.033 mmol, 37.5% yield) as a clear glass. This residue was dissolved in EtOH (0.5 mL) and 1M LiOH/water (0.13 mL) was added. After 18 h at ambient temperature the mixture was purified be HPLC (RP C18, MeCN/water 10-90%, 0.1% formic acid) to provide the title compound (11.6 mg, 0.029 mmol, 33.0% yield). LCMS: (M+1): m/z=400.3. $^1$H NMR (400 MHz, DMSO-d$_6$): δ ppm 0.99 (s, 9H), 1.20 (d, J=6.96 Hz, 3H), 2.30 (s, 3H), 2.46 (s, 2H), 3.12 (q, J=7.02 Hz, 1H), 3.73 (s, 2H), 6.99 (d, J=8.06 Hz, 1H), 7.18-7.25 (m, 2H), 7.26-7.32 (m, 2H), 7.35 (d, J=8.06 Hz, 1H), 8.24 (s, 1H), 8.92 (s, 1H), 12.2 (br s, 1H).

Example 45: 3-(4-(tert-Butylthio)-3-((3-chloro-1,2,4-thiadiazol-5-yl)amino)phenyl)butanoic Acid

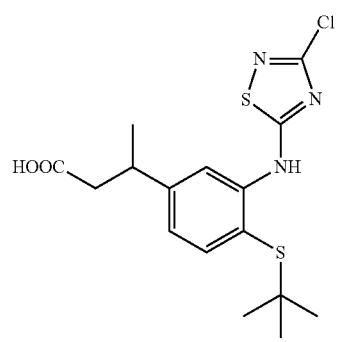 [SMILES: CC(CC(=O)O)c1ccc(SC(C)(C)C)c(Nc2nc(Cl)ns2)c1]

A mixture of methyl 3-(3-amino-4-(tert-butylthio)phenyl)butanoate (98 mg, 0.313 mmol), 3,5-dichloro-1,2,4-thiadiazole (53.4 mg, 0.345 mmol) and DMF (1 mL) was heated at 90° C. for 5.5 h. water was added and the mixture was extracted with EtOAc. The organic phase was dried (Na$_2$SO$_4$), concentrated and purified on silica gel (EtOAc/hexanes 0-10%) to provide methyl 3-(4-(tert-butylthio)-3-((3-chloro-1,2,4-thiadiazol-5-yl)amino)phenyl)butanoate (35.6 mg, 0.082 mmol, 26.1% yield). This residue was treated in MeOH (1 mL) and 1M LiOH/water (0.5 mL) and the mixture was stirred at ambient temperature for 30 min and then at 55° C. for 30 min. The mixture was purified by HPLC (C18 RP, MeCN/water 10-100%, 0.05% TFA) to provide the title compound (26.6 mg, 0.069 mmol, 21.99% yield) as a tan solid. LCMS (M+H)$^+$: m/z=386.2. $^1$H NMR (400 MHz, DMSO-d$_6$): δ ppm 1.21 (s, 9H), 1.25 (d, J=7.03 Hz, 3H), 2.52-2.55 (m, 2H), 3.18 (d, J=7.03 Hz, 1H), 7.10 (dd, J=8.01, 1.37 Hz, 1H), 7.49 (d, J=8.01 Hz, 1H), 8.12 (d, J=0.98 Hz, 1H), 10.74 (s, 1H), 12.12 (br. s., 1H).

Scheme VII: Synthesis of 3'-amino-4'-(tert-butylthio)-[1,1'-biphenyl]-2-carbonitrile and 3'-amino-4'-(tert-butylthio)-[1,1'-biphenyl]-2-carboxamide

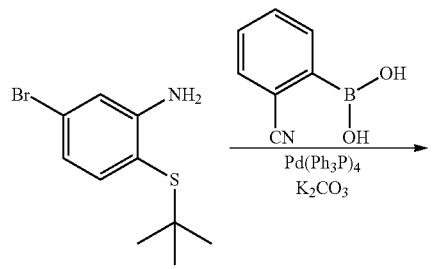

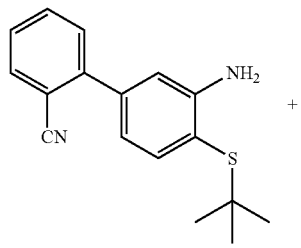

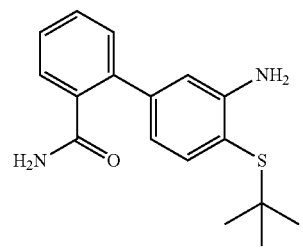

A solution of 5-bromo-2-(tert-butylthio)aniline (206 mg, 0.752 mmol) in DMF (5 mL) was degassed with a stream of nitrogen while adding (2-cyanophenyl)boronic acid (133 mg, 0.903 mmol), potassium carbonate (312 mg, 2.256 mmol), water (1.000 mL) and tetrakis(triphenylphosphine)palladium(0) (87 mg, 0.075 mmol) and the mixture was placed in an oil bath preheated to 100° C. The temperature was increased to 110° C. After 2 h, water was added and the mixture was extracted with EtOAc and the organic phase was washed with water, brine, dried (Na$_2$SO$_4$), concentrated and purified on silica gel (EtOAc/hexanes 10-100%) to provide the 3'-amino-4'-(tert-butylthio)-[1,1'-biphenyl]-2-carbonitrile (57.4 mg, 0.201 mmol, 26.8% yield, LCMS (M+H)$^+$: m/z=283.1) and 3'-amino-4'-(tert-butylthio)-[1,1'-biphenyl]-2-carboxamide (86 mg, 0.278 mmol, 36.9% yield, LCMS (M+H)$^+$: m/z=301.2).

Example 46: N-(4-(tert-butylthio)-2'-cyano-[1,1'-biphenyl]-3-yl)-2-(p-tolyl)acetamide

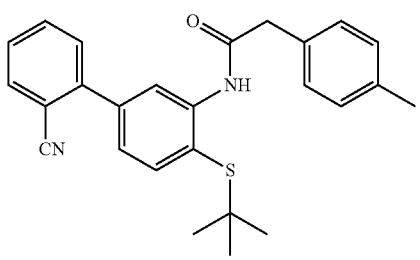 [SMILES: Cc1ccc(CC(=O)Nc2cc(-c3ccccc3C#N)ccc2SC(C)(C)C)cc1]

This compound was prepared from 3'-amino-4'-(tert-butylthio)-[1,1'-biphenyl]-2-carbonitrile and 2-(p-tolyl)acetic acid as described in Step B (Scheme V). LCMS (M+1)$^+$: m/z=415.3. $^1$H NMR (400 MHz, DMSO-d$_6$): δ ppm 1.06 (s, 9H), 2.31 (s, 3H), 3.34 (s, 2H), 7.20-7.26 (m, 2H), 7.27-7.37 (m, 3H), 7.62 (t, J=7.81 Hz, 3H), 7.78-7.85 (m, 1H), 7.98 (d, J=7.23 Hz, 1H), 8.52 (d, J=1.76 Hz, 1H), 9.11 (s, 1H).

Example 47: 4'-(tert-Butylthio)-3'-(2-(p-tolyl)acetamido)-[1,1'-biphenyl]-2-carboxamide

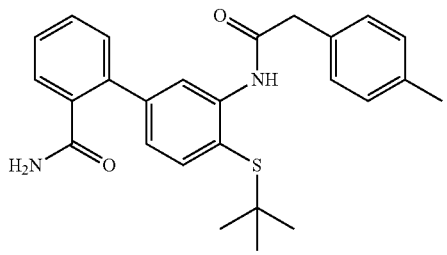 [SMILES: Cc1ccc(CC(=O)Nc2cc(-c3ccccc3C(N)=O)ccc2SC(C)(C)C)cc1]

This compound was prepared from 3'-amino-4'-(tert-butylthio)-[1,1'-biphenyl]-2-carboxamide and 2-(p-tolyl)acetic acid as described in Step B (Scheme V). LCMS (M+1)+: m/z=433.3. ¹H NMR (400 MHz, DMSO-d$_6$): δ ppm 1.04 (s, 9H), 2.31 (s, 3H), 3.75 (s, 2H), 7.11 (dd, J=7.91, 1.86 Hz, 1H), 7.20-7.26 (m, 2H), 7.28-7.38 (m, 4H), 7.39-7.55 (m, 4H), 7.71 (s, 1H) 8.41 (d, J=1.76 Hz, 1H), 9.01 (s, 1H).

Example 48: N-(4-(tert-butylthio)-2'-(N-hydroxycarbamimidoyl)-[1,1'-biphenyl]-3-yl)-2-(p-tolyl)acetamide

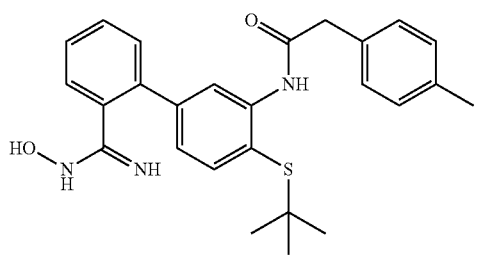 [SMILES: Cc1ccc(CC(=O)Nc2cc(-c3ccccc3C(=N)NO)ccc2SC(C)(C)C)cc1]

To a suspension of hydroxylamine hydrochloride (46.1 mg, 0.663 mmol) in DMSO (1 mL) was added TEA (0.092 mL, 0.663 mmol) and the mixture was stirred at ambient temperature for 15 min. The solid was filtered and washed with THF (2 mL). The filtrate was concentrated to 1 mL and then added to N-(4-(tert-butylthio)-2'-cyano-[1,1'-biphenyl]-3-yl)-2-(p-tolyl)acetamide (55 mg, 0.133 mmol). The mixture was stirred at 65° C. for 1 h and then at 75° C. for 48 h. The mixture was purified by HPLC (RP C18, MeCN/water 10-100%, 0.1% formic acid) to provide the title compound (8 mg, 0.018 mmol, 13.34% yield) as an off-white solid. LCMS (M+1)+: m/z=448.3. ¹H NMR (400 MHz, DMSO-d$_6$): δ ppm 1.04 (s, 9H), 2.31 (s, 3H), 3.74 (s, 2H), 5.59 (s, 2H), 7.13 (d, J=7.62 Hz, 1H), 7.20-7.26 (m, 2H), 7.28-7.36 (m, 3H), 7.38-7.53 (m, 4H), 8.37 (s, 1H), 9.00 (s, 1H), 9.22 (s, 1H).

Scheme VIII: Synthesis of di-tert-butyl ((5-(4'-(tert-butylthio)-3'-(2-(p-tolyl)acetamido)-[1,1'-biphenyl]-2-yl)-2H-tetrazol-2-yl)methyl) phosphate and di-tert-butyl ((5-(4'-(tert-butylthio)-3'-(2-(p-tolyl)acetamido-[1,1'-biphenyl]-2-yl)-1H-tetrazol-1-yl)methyl) phosphate

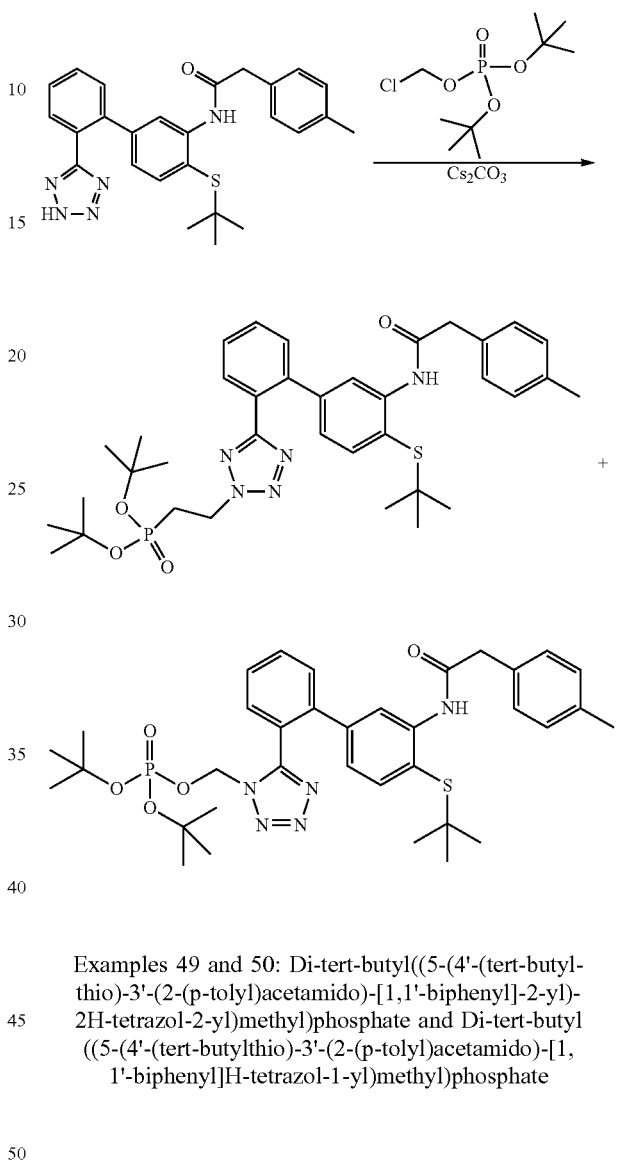

Examples 49 and 50: Di-tert-butyl((5-(4'-(tert-butylthio)-3'-(2-(p-tolyl)acetamido)-[1,1'-biphenyl]-2-yl)-2H-tetrazol-2-yl)methyl)phosphate and Di-tert-butyl ((5-(4'-(tert-butylthio)-3'-(2-(p-tolyl)acetamido)-[1,1'-biphenyl]H-tetrazol-1-yl)methyl)phosphate Example 49

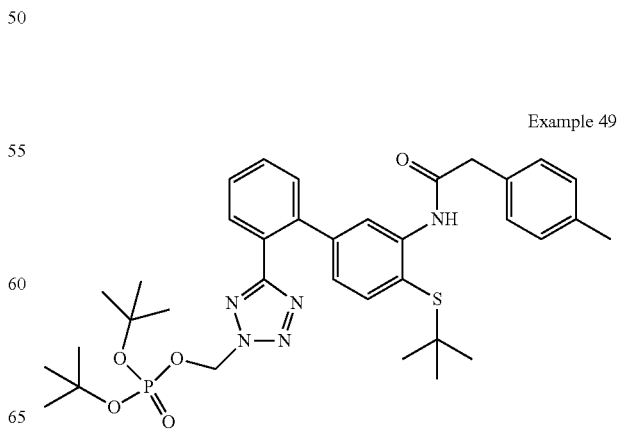

Example 50

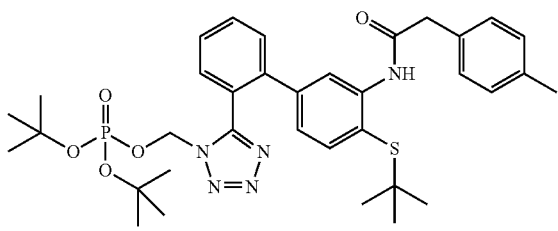

To a solution of N-(4-(tert-butylthio)-2'-(2H-tetrazol-5-yl)-[1,1'-biphenyl]-3-yl)-2-(p-tolyl)acetamide (320 mg, 0.699 mmol) in DMF (4 mL) was added cesium carbonate (273 mg, 0.839 mmol), sodium iodide (105 mg, 0.699 mmol) and di-tert-butyl (chloromethyl) phosphate (0.197 mL, 0.839 mmol) and the mixture was stirred at 55° C. for 18 h. Water was added followed by 1N HCl/water to pH-4-5. The mixture was extracted with EtOAc. The organic phase was dried ($Na_2SO_4$), concentrated and purified on silica gel (EtOAc/hexanes 0-25%) to provide di-tert-butyl ((5-(4'-(tert-butylthio)-3'-(2-(p-tolyl)acetamido)-[1,1'-biphenyl]-2-yl)-2H-tetrazol-2-yl)methyl) phosphate (Example 49, 162 mg, 0.238 mmol, 34.1% yield) and di-tert-butyl ((5-(4'-(tert-butylthio)-3'-(2-(p-tolyl)acetamido)-[1,1'-biphenyl]-2-yl)-1H-tetrazol-1-yl)methyl) phosphate (Example 50, 68 mg, 0.089 mmol, 12.73% yield). Example 49: LCMS (M+1)$^+$: m/z=680.6. $^1$H NMR (400 MHz, CHLOROFORM-d): δ ppm 1.04 (s, 9H), 1.45 (s, 18H), 2.37 (s, 3H), 3.70 (s, 2H), 6.16 (d, J=10.62 Hz, 2H), 6.80 (dd, J=7.87, 1.65 Hz, 1H), 7.22-7.28 (m, 4H), 7.30 (d, J=7.87 Hz, 1H), 7.45-7.60 (m, 3H), 7.88 (d, J=7.69 Hz, 1H), 8.41 (s, 1H), 8.77 (s, 1H). Example 50: LCMS (M+1)$^+$: m/z=680.6. $^1$H NMR (400 MHz, CHLOROFORM-d): δ ppm 0.99 (s, 9H), 1.38 (s, 18H), 2.37 (s, 3H), 3.72 (s, 2H), 5.60 (d, J=10.26 Hz, 2H), 6.66 (dd, J=7.87, 1.65 Hz, 1H), 7.26-7.33 (m, 5H), 7.56 (d, J=6.96 Hz, 1H), 7.61-7.72 (m, 3H), 8.48 (d, J=1.65 Hz, 1H), 8.80 (s, 1H).

Example 51: (5-(4'-(tert-Butylthio)-3'-(2-(p-tolyl)acetamido)-[1,1'-biphenyl]-2-yl)-2H-tetrazol-2-yl)methyl Dihydrogen Phosphate

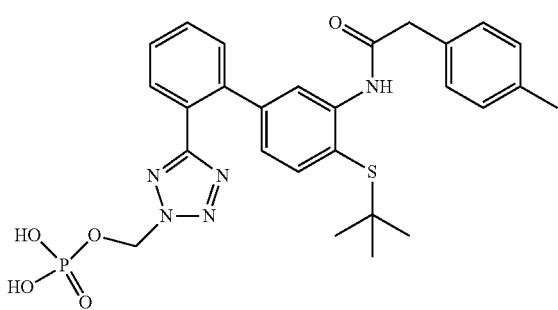 [SMILES: Cc1ccc(CC(=O)Nc2cc(-c3ccccc3-c3nnn(COP(=O)(O)O)n3)ccc2SC(C)(C)C)cc1]

To a solution of di-tert-butyl ((5-(4'-(tert-butylthio)-3'-(2-(p-tolyl)acetamido)-[1,1'-biphenyl]-2-yl)-2H-tetrazol-2-yl)methyl) phosphate (135 mg, 0.199 mmol) in dichloromethane (1 mL) was added TFA (1 ml, 12.98 mmol) and the mixture was stirred at ambient temperature for 4 h. The mixture was concentrated and coevaporated with MeCN and dried in vacuo. Hexanes was added, concentrated and dried in vacuo to provide the title compound as Trifluoroacetic acid salt (125.8 mg, 0.183 mmol, 92% yield) as a tan solid. LCMS (M+1)$^+$: m/z=568.4. $^1$H NMR (400 MHz, DMSO-$d_6$): δ ppm 1.02 (s, 9H), 2.31 (s, 3H), 3.71 (s, 2H), 6.15 (d, J=11.17 Hz, 2H), 6.80 (d, J=7.87 Hz, 1H), 7.19-7.25 (m, 2H), 7.26-7.31 (m, 2H), 7.35 (d, J=8.06 Hz, 1H), 7.54 (d, J=7.51 Hz, 1H), 7.57-7.63 (m, 1H), 7.67 (d, J=7.51 Hz, 1H), 7.81 (d, J=7.51 Hz, 1H), 8.11 (s, 1H), 8.95 (s, 1H).

Example 52: (5-(4'-(tert-Butylthio)-3'-(2-(p-tolyl)acetamido)-[1,1'-biphenyl]-2-yl)-1H-tetrazol-1-yl)methyl Dihydrogen

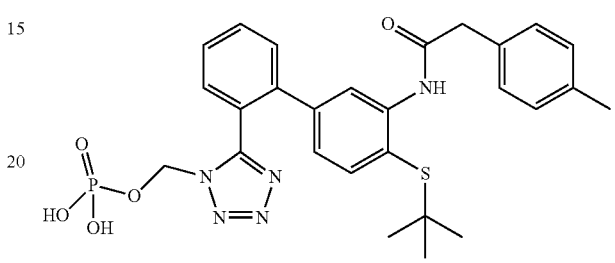

A solution of HCl (0.5 mL, 2.000 mmol) (4M/dioxane) was added to di-tert-butyl ((5-(4'-(tert-butylthio)-3'-(2-(p-tolyl)acetamido)-[1,1'-biphenyl]-2-yl)-1H-tetrazol-1-yl)methyl) phosphate (6 mg, 8.38 μmol) and the mixture was stirred at ambient temperature for 30 min. The mixture was concentrated, coevaporated with MeCN, triturated with dichloromethane and excess hexanes, concentrated and dried in vacuo to provide the title compound (5 mg, 8.37 μmol, 100% yield) as an off-white solid. LCMS (M+1)$^+$: m/z=568.3. $^1$H NMR (400 MHz, METHANOL-$d_4$): δ ppm 0.95 (s, 9H), 2.33 (s, 3H), 3.69 (s, 2H), 5.85 (d, J=10.35 Hz, 2H), 6.88 (dd, J=7.81, 1.56 Hz, 1H), 7.18-7.30 (m, 4H), 7.37 (d, J=7.81 Hz, 1H), 7.62 (d, J=7.42 Hz, 1H), 7.67 (d, J=7.42 Hz, 2H), 7.73 (d, J=7.42 Hz, 1H), 8.14 (s, 1H).

Example 53: (5-(4'-(tert-Butylthio)-3'-(2-(4-isopropylphenyl)acetamido)-[1,1'-biphenyl]-2-yl)-2H-tetrazol-2-yl)methyl Dihydrogen Phosphate

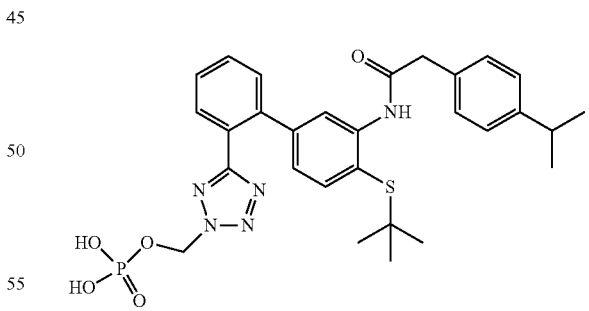

To a solution of di-tert-butyl ((5-(4'-(tert-butylthio)-3'-(2-(4-isopropylphenyl)acetamido)-[1,1'-biphenyl]-2-yl)-2H-tetrazol-2-yl)methyl) phosphate (260 mg, 0.331 mmol prepared as described in Scheme VIII) in dichloromethane (2 mL) at 0° C. was added TFA (2 mL) dropwise and the mixture was stirred at ambient temperature for 3 h. The mixture was concentrated, coevaporated with MeCN, dried and a small amount of EtOAc was added. The solid was filtered and dried to provide the title compound (132 mg, 0.219 mmol, 66.4% yield) as an off-white solid. LCMS (M+1)⁺: m/z=596.4. ¹H NMR (400 MHz, DMSO-d₆): δ ppm 0.99 (s, 9H), 1.21 (d, J=7.03 Hz, 6H), 2.82-2.96 (m, 1H), 3.71 (s, 2H), 6.16 (d, J=11.13 Hz, 2H), 6.80 (d, J=6.25 Hz, 1H), 7.24-7.38 (m, 5H), 7.54 (d, J=7.62 Hz, 1H), 7.61 (d, J=7.42 Hz, 1H), 7.67 (d, J=7.42 Hz, 1H), 7.81 (d, J=7.42 Hz, 1H), 8.12 (s, 1H), 8.96 (s, 1H).

Example 54: (5-(4'-(tert-Butylthio)-3'-(2-(4-isopropylphenyl)acetamido)-[1,1'-biphenyl]-2-yl)-1H-tetrazol-1-yl)methyl Dihydrogen Phosphate

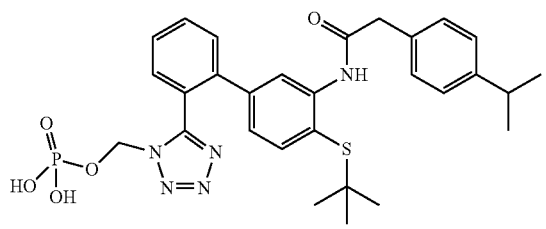 [SMILES: CC(C)c1ccc(CC(=O)Nc2cc(-c3ccccc3-c3nnnn3COP(=O)(O)O)ccc2SC(C)(C)C)cc1]

A mixture of di-tert-butyl ((5-(4'-(tert-butylthio)-3'-(2-(4-isopropylphenyl)acetamido)-[1,1'-biphenyl]-2-yl)-1H-tetrazol-1-yl)methyl) phosphate (72 mg, 0.102 mmol prepared as described in Scheme VIII) acetone (1.5 mL) and water (1.500 mL) was heated at 60° C. for 1 h. The mixture was concentrated and coevaporated with MeCN. The residue was dried, triturated with hexanes and the solid was filtered to provide the title compound (40.3 mg, 0.067 mmol, 65.9% yield) as a pale yellow solid. LCMS (M+1)⁺: m/z=596.3. ¹H NMR (400 MHz, DMSO-d₆): δ ppm 0.95 (s, 9H), 1.20 (d, J=6.84 Hz, 6H), 2.82-2.96 (m, 1H), 3.74 (s, 2H), 5.82 (d, J=10.35 Hz, 2H), 6.73 (d, J=7.62 Hz, 1H), 7.23-7.38 (m, 5H), 7.61-7.72 (m, 3H), 7.74-7.85 (m, 1H), 8.17 (s, 1H), 8.95 (s, 1H).

Examples 55 and 56: (5-(4'-(tert-Butylthio)-3'-(2-(p-tolyl)acetamido)-[1,1'-biphenyl]-2-yl)-2H-tetrazol-2-yl)methyl pivalate and (5-(4'-(tert-butylthio)-3'-(2-(p-tolyl)acetamido)-[1,1'-biphenyl]-2-yl)-1H-tetrazol-1-yl)methyl Pivalate Example 56

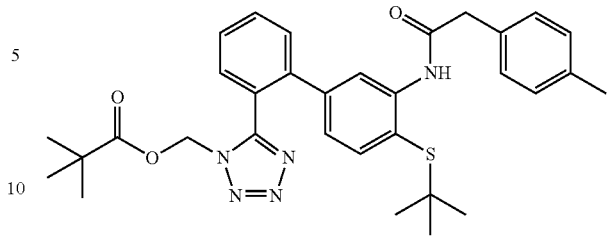

To a suspension of N-(4-(tert-butylthio)-2'-(2H-tetrazol-5-yl)-[1,1'-biphenyl]-3-yl)-2-(p-tolyl)acetamide (46 mg, 0.101 mmol) in acetonitrile (2 mL) was added potassium carbonate (34 mg, 0.246 mmol) followed by chloromethyl pivalate (0.016 mL, 0.111 mmol) and the mixture was stirred at 70° C. for 4 h. More chloromethyl pivalate (0.10 mL) was added and stirring at 70° C. continued for 5 h. Water was added and the mixture was extracted with EtOAc. The organic phase was dried (Na₂SO₄), concentrated and purified on silica gel (EtOAc/hexanes 0-20%) to provide (5-(4'-(tert-butylthio)-3'-(2-(p-tolyl)acetamido)-[1,1'-biphenyl]-2-yl)-2H-tetrazol-2-yl)methyl pivalate (23.5 mg, 0.041 mmol, 40.9% yield) and (5-(4'-(tert-butylthio)-3'-(2-(p-tolyl)acetamido)-[1,1'-biphenyl]-2-yl)-1H-tetrazol-1-yl)methyl pivalate (21 mg, 0.037 mmol, 36.5% yield). Example 55: LCMS (M+1)⁺: m/z=572.4. ¹H NMR (400 MHz, DMSO-d₆): δ ppm 1.01 (s, 9H), 1.09 (s, 9H), 2.31 (s, 3H), 3.70 (s, 2H), 6.47 (s, 2H), 6.78 (dd, J=8.01, 1.95 Hz, 1H), 7.20-7.24 (m, 2H), 7.26-7.30 (m, 2H), 7.32 (d, J=8.01 Hz, 1H), 7.52 (d, J=7.42 Hz, 1H), 7.56-7.63 (m, 1H), 7.64-7.72 (m, 1H), 7.79 (d, J=7.62 Hz, 1H), 8.13 (d, J=1.56 Hz, 1H), 8.92 (s, 1H). Example 56: LCMS (M+1)⁺: m/z=572.4. ¹H NMR (400 MHz, DMSO-d₆): δ ppm 0.92-1.05 (m, 18H), 2.30 (s, 3H), 3.72 (s, 2H), 6.00 (s, 2H), 6.75 (dd, J=7.81, 1.95 Hz, 1H), 7.18-7.24 (m, 2H), 7.25-7.31 (m, 2H), 7.34 (d, J=8.01 Hz, 1H), 7.60-7.73 (m, 3H), 7.74-7.83 (m, 1H), 8.18 (d, J=1.76 Hz, 1H), 8.94 (s, 1H).

Examples 57 and 58: (5-(4'-(tert-Butylthio)-3'-(2-(p-tolyl)acetamido)-[1,1'-biphenyl]-2-yl)-2H-tetrazol-2-yl)methyl Acetate and (5-(4'-(tert-butylthio)-3'-(2-(p-tolyl)acetamido)-[1,1'-biphenyl]-2-yl)-1H-tetrazol-1-yl)methyl Acetate Example 55

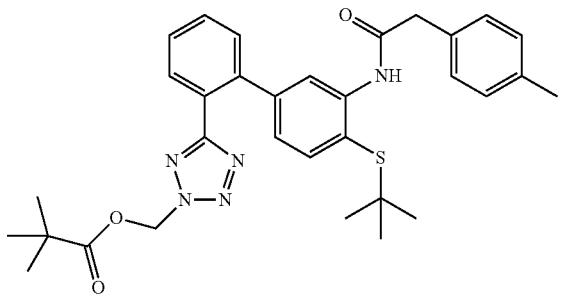

Example 57

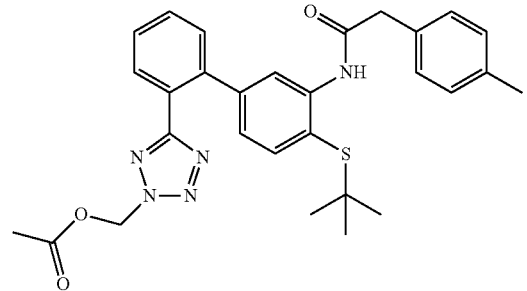

Example 58

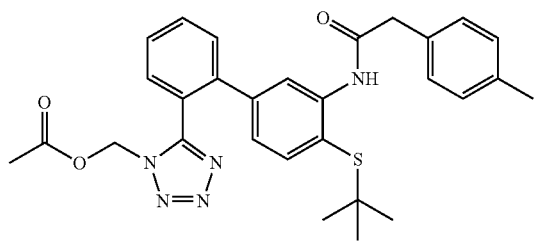

To a suspension of N-(4-(tert-butylthio)-2'-(2H-tetrazol-5-yl)-[1,1'-biphenyl]-3-yl)-2-(p-tolyl)acetamide (83 mg, 0.163 mmol) in acetonitrile (1.5 mL) was added potassium carbonate (45.1 mg, 0.326 mmol) followed by bromomethyl acetate (0.024 mL, 0.245 mmol) and the mixture was stirred at 60° C. under nitrogen atmosphere for 30 min. Saturated NH$_4$Cl/water and water was added and the mixture was extracted with EtOAc. The organic phase was dried (Na$_2$SO$_4$), concentrated and purified on silica gel (EtOAc/hexanes 0-40%) to provide(5-(4'-(tert-butylthio)-3'-(2-(p-tolyl)acetamido)-[1,1'-biphenyl]-2-yl)-2H-tetrazol-2-yl)methyl acetate (31.3 mg, 0.059 mmol, 36.2% yield) and (5-(4'-(tert-butylthio)-3'-(2-(p-tolyl)acetamido)-[1,1'-biphenyl]-2-yl)-1H-tetrazol-1-yl)methyl acetate (25.2 mg, 0.046 mmol, 28.0% yield). Example 57: LCMS (M+1)$^+$: m/z=530.4. $^1$H NMR (400 MHz, CHLOROFORM-d): δ ppm 1.04 (s, 9H), 2.12 (s, 3H), 2.37 (s, 3H), 3.70 (s, 2H), 6.35 (s, 2H), 6.82 (d, J=7.87 Hz, 1H), 7.21-7.29 (m, 4H), 7.33 (d, J=7.87 Hz, 1H), 7.45-7.62 (m, 3H), 7.89 (d, J=7.51 Hz, 1H), 8.37 (s, 1H), 8.76 (s, 1H). Example 58: LCMS (M+1)$^+$: m/z=530.5. $^1$H NMR (400 MHz, CHLOROFORM-d): δ ppm 1.00 (s, 9H), 1.95 (s, 3H), 2.38 (s, 3H), 3.73 (s, 2H), 5.70 (s, 2H), 6.63 (d, J=7.87 Hz, 1H), 7.21-7.34 (m, 5H), 7.52-7.61 (m, 2H), 7.62-7.76 (m, 2H), 8.54 (s, 1H), 8.82 (br. s., 1H).

Examples 59 and 60: N-(4-(tert-butylthio)-2'-(2-(methoxymethyl)-2H-tetrazol-5-yl)-[1,1'-biphenyl]-3-yl)-2-(p-tolyl)acetamide and N-(4-(tert-butylthio)-2'-(1-(methoxymethyl)-1H-tetrazol-5-yl)-[1,1'-biphenyl]-3-yl)-2-(p-tolyl)acetamide Example 59

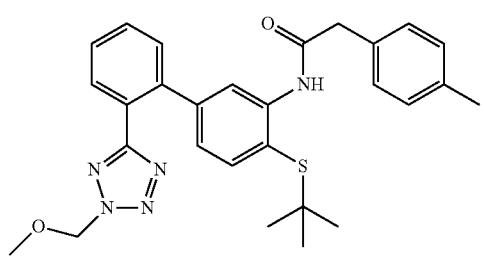

Example 60

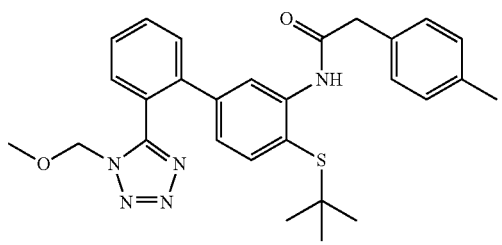

To a suspension of N-(4-(tert-butylthio)-2'-(2H-tetrazol-5-yl)-[1,1'-biphenyl]-3-yl)-2-(p-tolyl)acetamide (55 mg, 0.113 mmol) in acetonitrile (1.2 mL) was added TEA (0.063 mL, 0.452 mmol), sodium iodide (15 mg, 0.100 mmol) and MOM-Cl (0.017 mL, 0.226 mmol) and the mixture was stirred at ambient temperature for 10 min. The mixture was partitioned between EtOAc and water. The organic phase was dried (Na$_2$SO$_4$), concentrated and purified on silica gel (EtOAc/hexanes 0-40%) to provide N-(4-(tert-butylthio)-2'-(2-(methoxymethyl)-2H-tetrazol-5-yl)-[1,1'-biphenyl]-3-yl)-2-(p-tolyl)acetamide (19.8 mg, 0.037 mmol, 33.2% yield) and N-(4-(tert-butylthio)-2'-(1-(methoxymethyl)-1H-tetrazol-5-yl)-[1,1'-biphenyl]-3-yl)-2-(p-tolyl)acetamide (24.2 mg, 0.048 mmol, 42.7% yield). Example 59: LCMS (M+1)$^+$: m/z=502.4. $^1$H NMR (400 MHz, CHLOROFORM-d): δ ppm 1.03 (s, 9H), 2.37 (s, 3H), 3.33 (s, 3H), 3.69 (s, 2H), 5.71 (s, 2H), 6.80 (dd, J=8.01, 1.95 Hz, 1H), 7.31 (d, J=8.01 Hz, 1H), 7.24-7.26 (m, 4H), 7.45-7.60 (m, 3H), 7.90 (d, J=7.62 Hz, 1H), 8.46 (d, J=1.76 Hz, 1H), 8.78 (s, 1H). Example 60: LCMS (M+1)$^+$: m/z=502.4. $^1$H NMR (400 MHz, CHLOROFORM-d): δ ppm 0.98 (s, 9H), 2.37 (s, 3H), 3.24 (s, 3H), 3.72 (s, 2H), 5.20 (s, 2H), 6.67 (dd, J=7.91, 1.86 Hz, 1H), 7.24-7.26 (m, 5H), 7.50-7.60 (m, 2H), 7.61-7.74 (m, 2H), 8.48 (d, J=1.76 Hz, 1H), 8.80 (s, 1H).

Examples 61 and 62: N-(4-(tert-butylthio)-2'-(2-methyl-2H-tetrazol-5-yl)-[1,1'-biphenyl]-3-yl)-2-(p-tolyl)acetamide and N-(4-(tert-butylthio)-2'-(1-methyl-1H-tetrazol-5-yl)-[1,1'-biphenyl]-3-yl)-2-(p-tolyl)acetamide Example 61

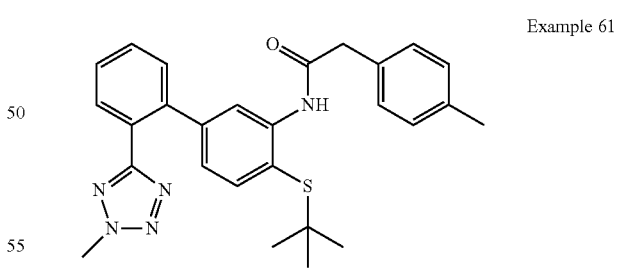

Example 62

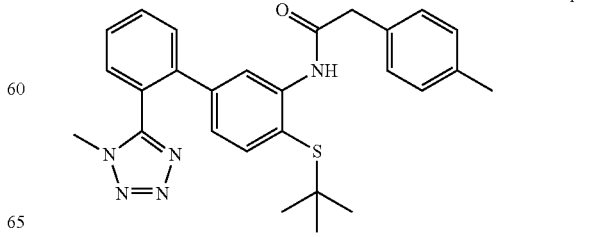

To a solution of N-(4-(tert-butylthio)-2'-(2H-tetrazol-5-yl)-[1,1'-biphenyl]-3-yl)-2-(p-tolyl)acetamide (48 mg, 0.105 mmol) in THF (1 mL) was added TMS-diazomethane (0.5 mL, 1.000 mmol) (2M/hexanes) and the mixture was stirred at ambient temperature for 1 h. Water was added followed by a small amount of MeOH and excess EtOAc and the mixture was stirred at ambient temperature for 30 min. The mixture was washed with saturated NaHCO$_3$/water and the organic phase was dried (Na$_2$SO$_4$), concentrated and purified on silica gel (EtOAc/hexanes 0-50%) to provide N-(4-(tert-butylthio)-2'-(1-methyl-1H-tetrazol-5-yl)-[1,1'-biphenyl]-3-yl)-2-(p-tolyl)acetamide (15.4 mg, 0.033 mmol, 31.1% yield) and N-(4-(tert-butylthio)-2'-(2-methyl-2H-tetrazol-5-yl)-[1,1'-biphenyl]-3-yl)-2-(p-tolyl)acetamide (6.6 mg, 0.013 mmol, 12.67% yield). Example 61: LCMS (M+1)$^+$: m/z=472.4. $^1$H NMR (400 MHz, CHLOROFORM-d): δ ppm 0.99 (s, 9H), 2.38 (s, 3H), 3.40 (s, 3H), 3.75 (s, 2H), 6.53 (d, J=7.81 Hz, 1H), 7.24-7.27 (m, 5H), 7.50-7.62 (m, 2H), 7.66 (s, 2H), 8.66 (s, 1H), 8.86 (s, 1H). Example 62: LCMS (M+1)$^+$: m/z=472.4. $^1$H NMR (400 MHz, CHLOROFORM-d): δ ppm 1.03 (s, 9H), 2.37 (s, 3H), 3.70 (s, 2H), 4.23 (s, 3H), 6.80 (dd, J=8.01, 1.95 Hz, 1H), 7.24-7.26 (m, 4H), 7.31 (d, J=8.01 Hz, 1H), 7.44-7.59 (m, 3H), 7.85 (d, J=7.42 Hz, 1H), 8.41 (d, J=1.76 Hz, 1H), 8.77 (s, 1H).

Scheme IX: Synthesis of N-(5-(2-(2H-tetrazol-5-yl)pyridin-3-yl)-2-(tert-butylthio)phenyl)-2-(p-tolyl)acetamide

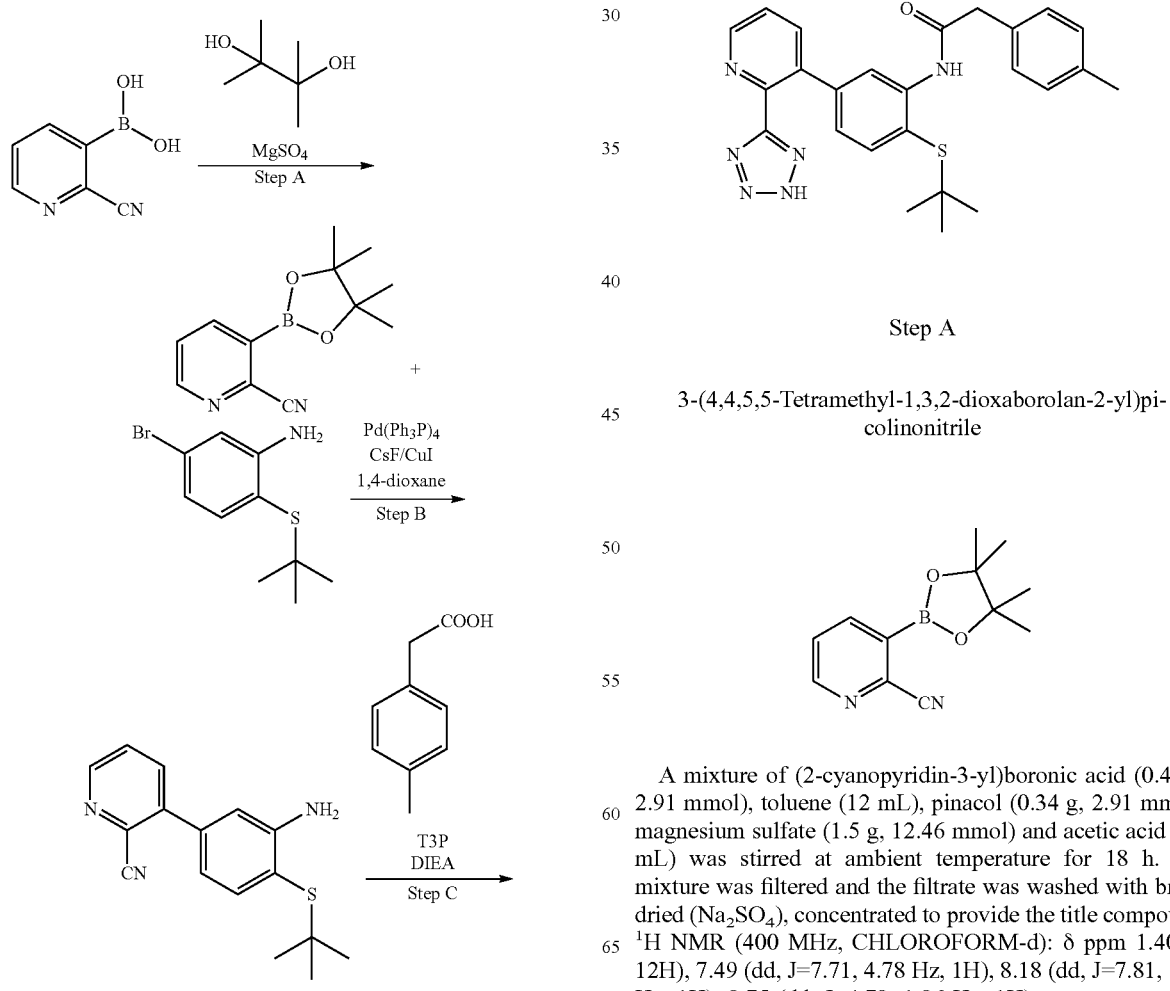

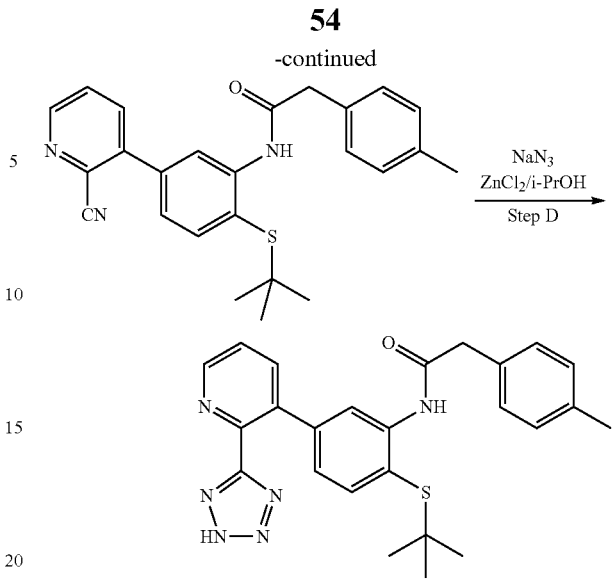

Example 63: N-(5-(2-(2H-tetrazol-5-yl)pyridin-3-yl)-2-(tert-butylthio)phenyl)-2-(p-tolyl)acetamide Step A 3-(4,4,5,5-Tetramethyl-1,3,2-dioxaborolan-2-yl)picolinonitrile A mixture of (2-cyanopyridin-3-yl)boronic acid (0.43 g, 2.91 mmol), toluene (12 mL), pinacol (0.34 g, 2.91 mmol), magnesium sulfate (1.5 g, 12.46 mmol) and acetic acid (0.1 mL) was stirred at ambient temperature for 18 h. The mixture was filtered and the filtrate was washed with brine, dried (Na$_2$SO$_4$), concentrated to provide the title compound. $^1$H NMR (400 MHz, CHLOROFORM-d): δ ppm 1.40 (s, 12H), 7.49 (dd, J=7.71, 4.78 Hz, 1H), 8.18 (dd, J=7.81, 1.76 Hz, 1H), 8.75 (dd, J=4.78, 1.86 Hz, 1H).

Step B

3-(3-Amino-4-(tert-butylthio)phenyl)picolinonitrile

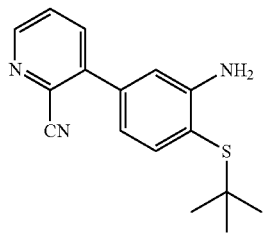 [SMILES: CC(C)(C)Sc1ccc(-c2cccnc2C#N)cc1N]

A mixture of 5-bromo-2-(tert-butylthio)aniline (200 mg, 0.769 mmol), 3-(4,4,5,5-tetramethyl-1,3,2-dioxaborolan-2-yl)picolinonitrile (230 mg, 0.999 mmol), cesium fluoride (350 mg, 2.306 mmol), copper(I) iodide (29.3 mg, 0.154 mmol), tetrakis(triphenylphosphine) palladium (0) (178 mg, 0.154 mmol) and 1,4-Dioxane (6 mL) was degassed with a stream of nitrogen for 5 min then placed in an oil bath at 100° C. under nitrogen atmosphere for 2.5 h. The mixture was diluted with water and extracted with EtOAc. The organic phase was dried ($Na_2SO_4$), concentrated and purified on silica gel (EtOAc/hexanes 0-20%) to provide the title compound (108.5 mg, 0.371 mmol, 48.3% yield).). $^1$H NMR (400 MHz, CHLOROFORM-d): δ ppm 1.36 (s, 9H), 6.83 (dd, J=7.91, 1.86 Hz, 1H), 6.93 (d, J=1.56 Hz, 1H), 7.50 (d, J=8.01 Hz, 1H), 7.56 (dd, J=8.01, 4.69 Hz, 1H), 7.86 (dd, J=8.01, 1.56 Hz, 1H), 8.69 (dd, J=4.69, 1.37 Hz, 1H).

Step C

N-(2-(tert-Butylthio)-5-(2-cyanopyridin-3-yl)phenyl)-2-(p-tolyl)acetamide

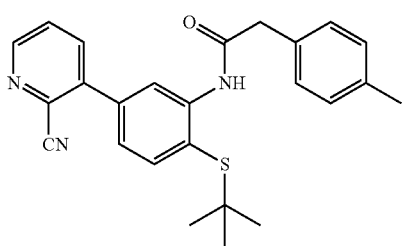 [SMILES: Cc1ccc(CC(=O)Nc2cc(-c3cccnc3C#N)ccc2SC(C)(C)C)cc1]

To a solution of 3-(3-amino-4-(tert-butylthio)phenyl)picolinonitrile (76 mg, 0.228 mmol) in Ethyl acetate (2.5 mL) was added 2-(p-tolyl)acetic acid (41.1 mg, 0.274 mmol) and 2,4,6-tripropyl-1,3,5,2,4,6-trioxatriphosphinane 2,4,6-trioxide (174 mg, 0.274 mmol) (50%/EtOAc) followed by dropwise addition of DIEA (0.119 mL, 0.684 mmol) and the mixture was stirred at ambient temperature for 3 h. More 2-(p-tolyl)acetic acid (20 mg), 2,4,6-tripropyl-1,3,5,2,4,6-trioxatriphosphinane 2,4,6-trioxide (87 mg) and DIEA (0.060 mL) was added. After 18 h the mixture was washed with water and the organic phase was dried ($Na_2SO_4$), concentrated and purified by HPLC (RP C18 MeCN/water 10-100%, 0.1% formic acid) to provide the title compound (43.8 mg, 0.103 mmol, 45.3% yield). LCMS (M+1)$^+$: m/z=416.3. $^1$H NMR (400 MHz, CHLOROFORM-d): δ ppm 1.06 (s, 9H), 2.38 (s, 3H), 3.77 (s, 2H), 7.20-7.28 (m, 4H), 7.52-7.64 (m, 2H), 7.93 (d, J=8.01 Hz, 1H), 8.71 (d, J=4.49 Hz, 1H), 8.79 (s, 1H), 8.94 (s, 1H).

Step D

N-(5-(2-(2H-Tetrazol-5-yl)pyridin-3-yl)-2-(tert-butylthio)phenyl)-2-(p-tolyl)acetamide

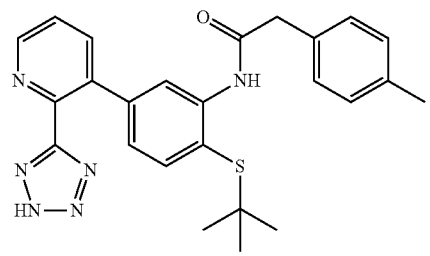 [SMILES: Cc1ccc(CC(=O)Nc2cc(-c3cccnc3-c3nn[nH]n3)ccc2SC(C)(C)C)cc1]

To a solution of N-(2-(tert-butylthio)-5-(2-cyanopyridin-3-yl)phenyl)-2-(p-tolyl)acetamide (42 mg, 0.099 mmol) in 1-propanol (2.5 mL) was added sodium azide (12.88 mg, 0.198 mmol) and zinc chloride (0.594 mL, 0.297 mmol) (0.5 M/THF) and the mixture was heated at 95° C. under nitrogen atmosphere for 24 h. The mixture was filtered and purified by HPLC (RP C18 MeCN/water 10-100%, 0.1% formic acid) to provide the title compound (6.5 mg, 0.013 mmol, 13.59% yield). LCMS (M+1)$^+$: m/z=459.2. $^1$H NMR (400 MHz, DMSO-$d_6$): δ ppm 1.03 (s, 9H), 2.31 (s, 3H), 3.72 (s, 2H), 6.92 (d, J=6.84 Hz, 1H), 7.19-7.25 (m, 2H), 7.29 (d, J=8.01 Hz, 2H), 7.42 (d, J=7.81 Hz, 1H), 7.71 (dd, J=7.71, 4.78 Hz, 1H), 8.00 (d, J=7.62 Hz, 1H), 8.23 (s, 1H), 8.81 (d, J=3.91 Hz, 1H), 9.00 (s, 1H).

Scheme X: Synthesis of N-(5-(2-(1H-tetrazol-5-yl)phenyl)-2-(tert-butylthio)pyridin-3-yl)-2-(p-tolyl)acetamide

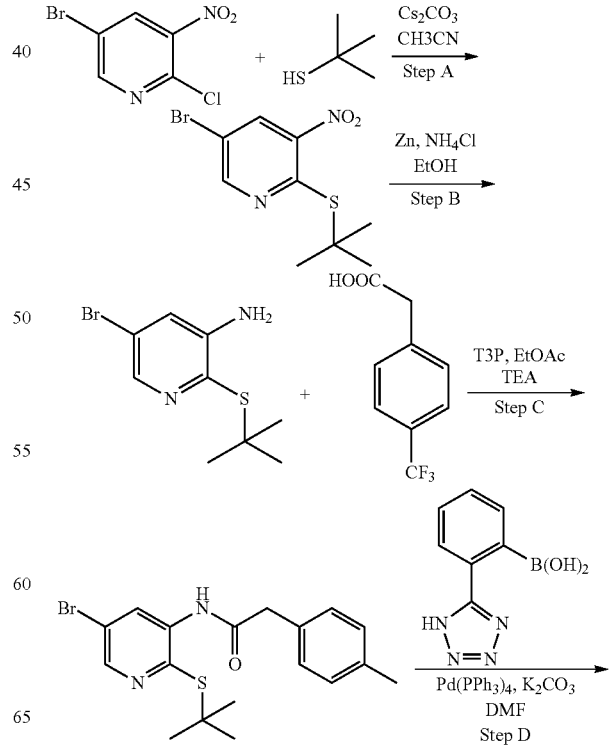

-continued

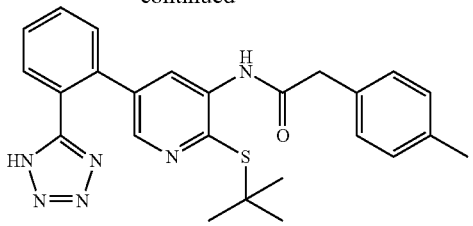

Example 64: N-(5-(2-(1H-tetrazol-5-yl)phenyl)-2-(tert-butylthio)pyridin-3-yl)-2-(p-tolyl)acetamide

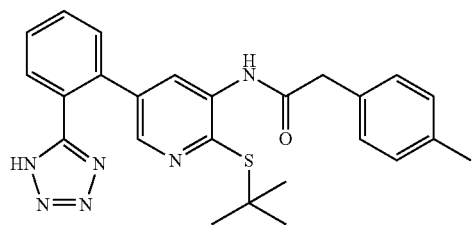 [SMILES: Cc1ccc(CC(=O)Nc2cc(-c3ccccc3-c3nnn[nH]3)cnc2SC(C)(C)C)cc1]

Step A

5-Bromo-2-(tert-butylthio)-3-nitropyridine

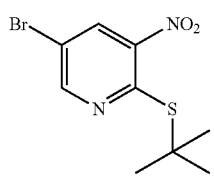

This compound was prepared from 5-bromo-2-chloro-3-nitropyridine following the procedure described in Step A (Scheme I). $^1$H NMR (400 MHz, DMSO-d$_6$): δ ppm 1.58 (s, 9H), 8.73 (d, J=1.83 Hz, 1H), 8.97 (d, J=1.65 Hz, 1H).

Step B

5-Bromo-2-(tert-butylthio)pyridin-3-amine

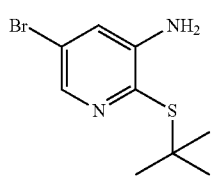

This compound was prepared from 5-bromo-2-(tert-butylthio)-3-nitropyridine following the procedure described in Step B (Scheme I). $^1$H NMR (400 MHz, DMSO-d$_6$): δ ppm 1.39 (s, 9H), 5.60 (br. s., 2H), 7.20 (d, J=1.83 Hz, 1H), 7.84 (d, J=1.83 Hz, 1H).

Step C

N-(5-Bromo-2-(tert-butylthio)pyridin-3-yl)-2-(p-tolyl)acetamide

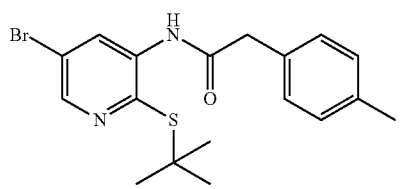 [SMILES: Cc1ccc(CC(=O)Nc2cc(Br)cnc2SC(C)(C)C)cc1]

This compound was prepared from 5-bromo-2-(tert-butylthio)pyridin-3-amine following the procedure described in Step C (Scheme I). $^1$H NMR (400 MHz, DMSO-d$_6$): δ ppm 1.36 (s, 9H), 2.29 (s, 3H), 3.71 (s, 2H), 7.13-7.21 (m, 2H), 7.26 (d, J=7.51 Hz, 2H), 8.31 (br. s., 1H), 8.45 (d, J=1.47 Hz, 1H), 9.35 (s, 1H).

Step D

N-(5-(2-(1H-Tetrazol-5-yl)phenyl)-2-(tert-butylthio)pyridin-3-yl)-2-(p-tolyl)acetamide

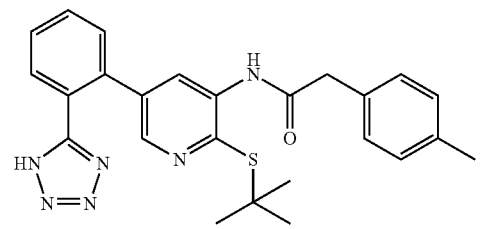

This compound was prepared from N-(5-bromo-2-(tert-butylthio)pyridin-3-yl)-2-(p-tolyl)acetamide following the procedure described in Step D (Scheme I). $^1$H NMR (400 MHz, METHANOL-d$_4$): δ ppm 1.21 (s, 9H), 2.36 (s, 3H), 3.74 (s, 2H), 7.28 (q, J=7.69 Hz, 4H), 7.60-7.69 (m, 2H), 7.75 (dd, J=18.86, 7.51 Hz, 2H), 8.00 (d, J=1.65 Hz, 1H), 8.39 (s, 1H).

The following examples were synthesized following the procedures described in Scheme X.

Example 65: N-(5-(2-(1H-tetrazol-5-yl)phenyl)-2-(tert-butylthio)pyridin-3-yl)-2-(4-(trifluoromethyl)phenyl)acetamide

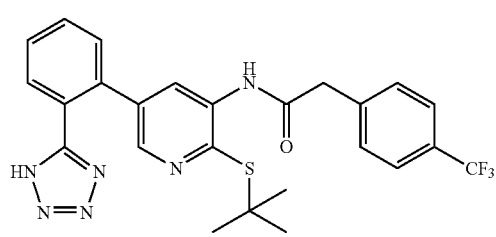 [SMILES: CC(C)(C)Sc1ncc(-c2ccccc2-c2nnn[nH]2)cc1NC(=O)Cc1ccc(C(F)(F)F)cc1]

¹H NMR (400 MHz, METHANOL-d₄): δ ppm 1.28 (s, 9H), 3.88 (br. s., 2H), 7.57-7.66 (m, 4H), 7.70 (d, J=7.14 Hz, 4H), 7.76 (d, J=7.33 Hz, 1H), 8.02 (br. s., 1H), 8.17 (br. s., 1H).

Example 66: N-(5-(2-(1H-tetrazol-5-yl)phenyl)-2-(tert-butylthio)pyridin-3-yl)-2-(2,4-dimethylphenyl)acetamide

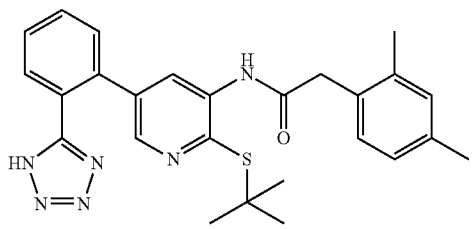 [SMILES: Cc1ccc(CC(=O)Nc2cc(-c3ccccc3-c3nnn[nH]3)cnc2SC(C)(C)C)c(C)c1]

¹H NMR (400 MHz, DMSO-d₆): δ ppm 1.31 (s, 9H), 2.22 (s, 3H), 2.26 (s, 3H), 3.70 (s, 2H), 6.96-7.09 (m, 1H), 7.13-7.28 (m, 1H), 7.28-7.46 (m, 2H), 7.46-7.71 (m, 4H), 7.76 (d, J=7.51 Hz, 1H), 8.01 (br. s., 1H), 9.02 (s, 1H).

Example 67: N-(5-(2-(1H-tetrazol-5-yl)phenyl)-2-(tert-butylthio)pyridin-3-yl)-2-(2-(trifluoromethyl)phenyl)acetamide

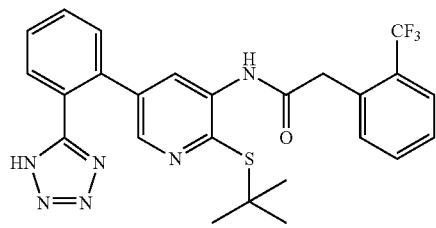 [SMILES: CC(C)(C)Sc1ncc(-c2ccccc2-c2nnn[nH]2)cc1NC(=O)Cc1ccccc1C(F)(F)F]

¹H NMR (400 MHz, DMSO-d₆): δ ppm 1.43 (br. s., 9H), 3.96 (br. s., 2H), 7.49-7.82 (m, 9H), 8.05 (br. s., 1H), 9.34 (br. s., 1H).

Example 68: N-(5-(2-(1H-tetrazol-5-yl)phenyl)-2-(tert-butylthio)pyridin-3-yl)-2-(4-cyclopropylphenyl)acetamide

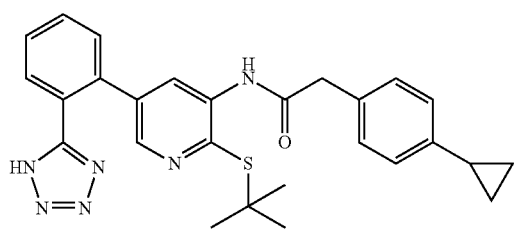 [SMILES: CC(C)(C)Sc1ncc(-c2ccccc2-c2nnn[nH]2)cc1NC(=O)Cc1ccc(C2CC2)cc1]

¹H NMR (400 MHz, DMSO-d₆): δ ppm 0.54-0.73 (m, 2H), 0.86-1.00 (m, 2H), 1.35 (s, 9H), 1.78-2.00 (m, 1H), 3.66 (br. s., 2H), 7.06 (d, J=7.87 Hz, 2H), 7.22 (d, J=7.51 Hz, 2H), 7.56-7.67 (m, 2H), 7.67-7.80 (m, 2H), 7.89 (br. s., 1H), 8.02 (s, 1H), 9.19 (s, 1H).

Scheme XI: Synthesis of N-(5-(2-(2H-tetrazol-5-yl)phenyl)-2-(tert-butylthio)pyridin-3-yl)-2-(4-isopropylphenyl)acetamide

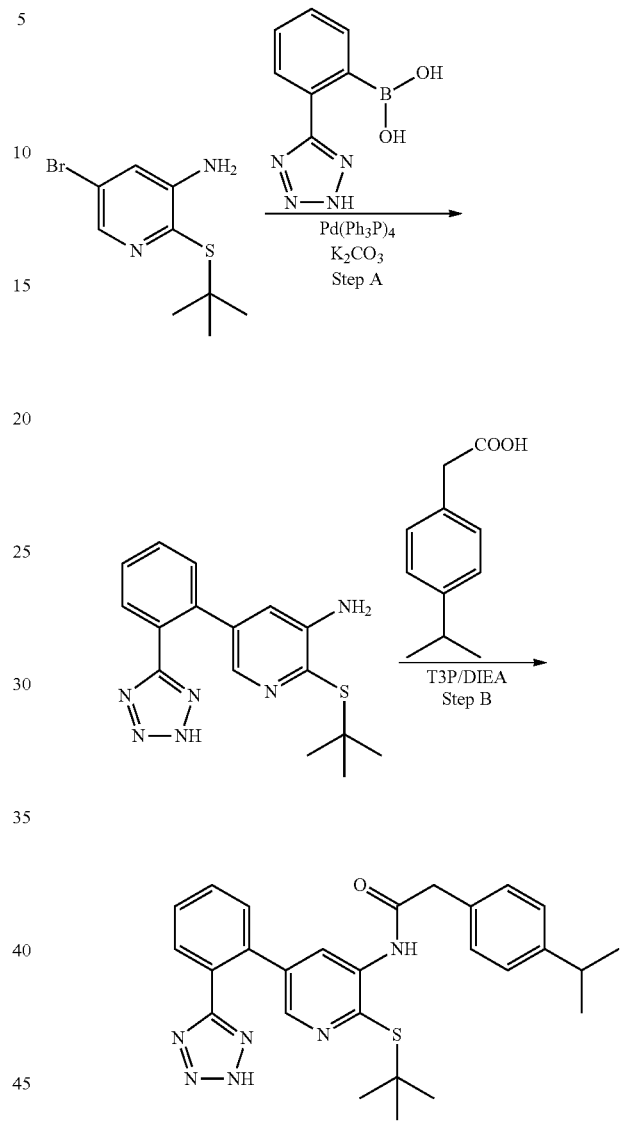

Example 69: N-(5-(2-(2H-tetrazol-5-yl)phenyl)-2-(tert-butylthio)pyridin-3-yl)-2-(4-isopropylphenyl)acetamide

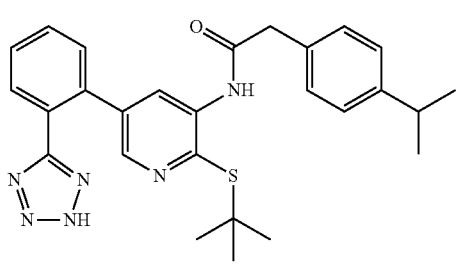 [SMILES: CC(C)c1ccc(CC(=O)Nc2cc(-c3ccccc3-c3nn[nH]n3)cnc2SC(C)(C)C)cc1]

Step A

5-(2-(2H-Tetrazol-5-yl)phenyl)-2-(tert-butylthio)pyridin-3-amine

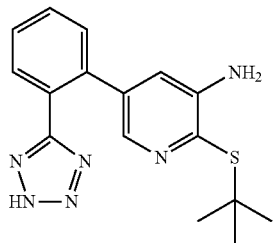 [SMILES: CC(C)(C)Sc1ncc(-c2ccccc2-c2nn[nH]n2)cc1N]

This compound was prepared from 5-bromo-2-(tert-butylthio)pyridin-3-amine following the procedure described in Step A (Scheme V). LCMS (M+1)+: m/z=327.2. ¹H NMR (400 MHz, DMSO-d₆): δ ppm 1.40 (s, 9H), 5.33 (s, 2H), 6.75 (d, J=1.95 Hz, 1H), 7.45 (d, J=2.15 Hz, 1H), 7.59 (d, J=6.64 Hz, 3H), 7.64-7.77 (m, 1H), 8.00-8.10 (m, 1H).

Step B

N-(5-(2-(2H-tetrazol-5-yl)phenyl)-2-(tert-butylthio)pyridin-3-yl)-2-(4-isopropylphenyl)acetamide

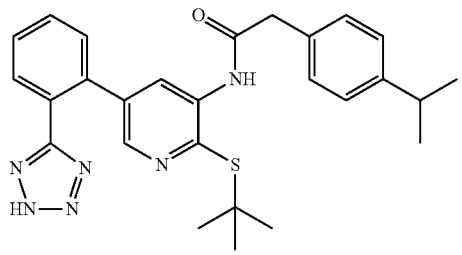 [SMILES: CC(C)c1ccc(CC(=O)Nc2cc(-c3ccccc3-c3nn[nH]n3)cnc2SC(C)(C)C)cc1]

This compound was prepared from 5-(2-(2H-tetrazol-5-yl)phenyl)-2-(tert-butylthio)pyridin-3-amine following the procedure described in Step B (Scheme V). LCMS (M+1)+: m/z=487.3. ¹H NMR (400 MHz, DMSO-d₆): δ ppm 1.19 (d, J=6.84 Hz, 6H), 1.35 (s, 9H), 2.87 (quin, J=6.88 Hz, 1H), 3.68 (s, 2H), 7.25 (q, J=8.14 Hz, 4H), 7.56-7.68 (m, 2H), 7.68-7.80 (m, 2H), 7.89 (s, 1H), 8.02 (d, J=1.76 Hz, 1H), 9.24 (s, 1H).

Example 70: N-(5-(2-(2H-tetrazol-5-yl)phenyl)-2-(tert-butylthio)pyridin-3-yl)-2-mesitylacetamide

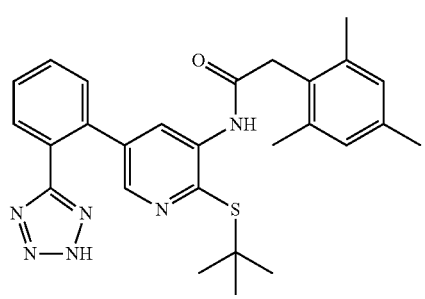

This compound was prepared from 5-(2-(2H-tetrazol-5-yl)phenyl)-2-(tert-butylthio)pyridin-3-amine following the procedure described in Step B (Scheme V). LCMS (M+1)+: m/z 487.3. ¹H NMR (400 MHz, DMSO-d₆): δ ppm 1.27 (s, 9H), 2.21-2.28 (m, 9H), 3.72 (s, 2H), 6.92 (s, 2H), 7.58-7.68 (m, 2H), 7.69-7.81 (m, 2H), 8.01 (s, 1H), 8.07 (s, 1H), 8.94 (s, 1H).

Scheme XII: Synthesis of N-(4-(tert-butylthio)-2'-(1H-1,2,3-triazol-4-yl)-[1,1'-biphenyl]-3-yl)-2-(p-tolyl)acetamide

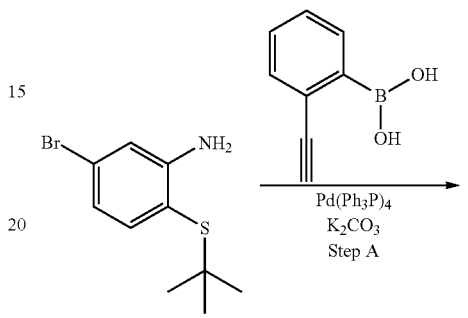

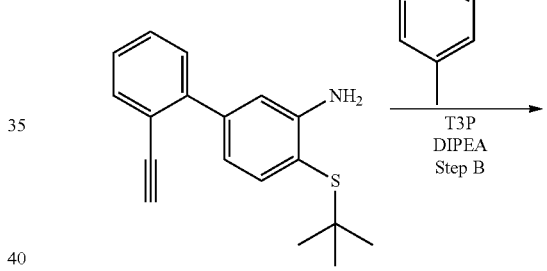

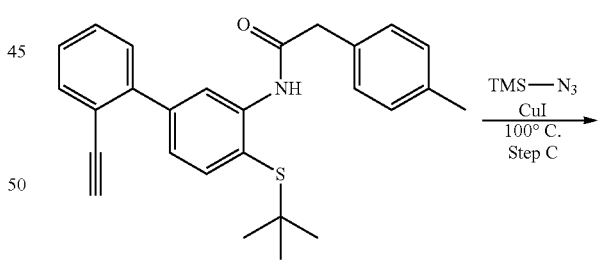

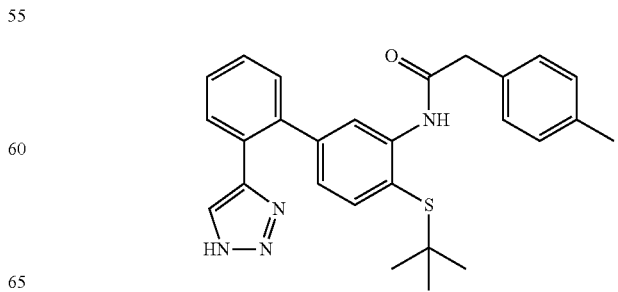

Example 71: N-(4-(tert-butylthio)-2'-(1H-1,2,3-tri-azol-4-yl)-[1,1'-biphenyl]-3-yl)-2-(p-tolyl)acetamide

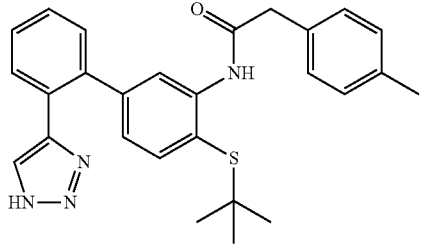 [SMILES: Cc1ccc(CC(=O)Nc2cc(-c3ccccc3-c3c[nH]nn3)ccc2SC(C)(C)C)cc1]

Step A 4-(tert-Butylthio)-2'-ethynyl-[1,1'-biphenyl]-3-amine

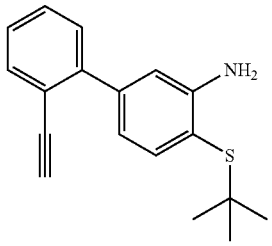 [SMILES: C#Cc1ccccc1-c1ccc(SC(C)(C)C)c(N)c1]

This compound was prepared from 5-bromo-2-(tert-butylthio)aniline and (2-ethynylphenyl)boronic acid following procedure described in Step A (Scheme V). LCMS (M+1)+: m/z 282.2. $^1$H NMR (400 MHz, CHLOROFORM-d): δ ppm 1.34-1.41 (m, 9H), 3.08 (s, 1H), 6.91 (dd, J=7.91, 1.86 Hz, 1H), 6.98 (d, J=1.76 Hz, 1H), 7.28 (d, J=13.47 Hz, 1H), 7.35-7.48 (m, 3H), 7.61 (d, J=7.81 Hz, 1H).

Step B

N-(4-(tert-butylthio)-2'-ethynyl-[1,1'-biphenyl]-3-yl)-2-(p-tolyl)acetamide

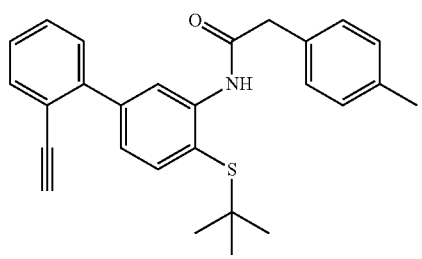 [SMILES: C#Cc1ccccc1-c1ccc(SC(C)(C)C)c(NC(=O)Cc2ccc(C)cc2)c1]

This compound was prepared from 4-(tert-butylthio)-2'-ethynyl-[1,1'-biphenyl]-3-amine following the procedure described in Step B (Scheme V). LCMS (M+1)+: m/z 414.3. $^1$H NMR (400 MHz, CHLOROFORM-d): δ ppm 1.06 (s, 9H), 2.38 (s, 3H), 3.07 (s, 1H), 3.76 (s, 2H), 7.22-7.35 (m, 5H), 7.37-7.50 (m, 4H), 7.61 (d, J=7.69 Hz, 1H), 8.79 (s, 1H), 8.87 (br. s., 1H).

Step C

N-(4-(tert-butylthio)-2'-(1H-1,2,3-triazol-4-yl)-[1,1'-biphenyl]-3-yl)-2-(p-tolyl)acetamide

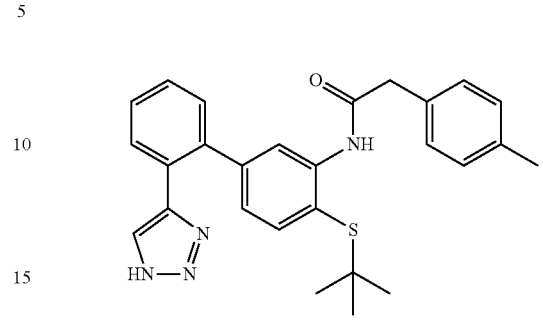

To a solution of N-(4-(tert-butylthio)-2'-ethynyl-[1,1'-biphenyl]-3-yl)-2-(p-tolyl)acetamide (22 mg, 0.045 mmol) in DMF (0.8 mL)/methanol (0.200 mL) was added copper(I) iodide (0.861 mg, 4.52 μmol) and TMS-N$_3$ (0.012 mL, 0.090 mmol) and the mixture was stirred at 100° C. for 5 h. More copper (I) iodide (5 mg) and TMS-N$_3$ (0.40 mL) was added and the mixture was stirred for 30 min at 100° C. Water was added and the mixture was extracted with EtOAc. The organic phase was dried (Na$_2$SO$_4$), concentrated and purified by HPLC (RP C18, MeCN/water 10-100%, 0.1% formic acid) to provide the title compound (3 mg, 6.50 μmol, 14.39% yield). LCMS (M+1)+: m/z 457.4. $^1$H NMR (400 MHz, DMSO-d$_6$): δ ppm 1.03 (s, 9H), 2.31 (s, 3H), 3.72 (s, 2H), 6.80-6.95 (m, 1H), 7.18-7.25 (m, 2H), 7.26-7.32 (m, 2H), 7.33-7.60 (m, 4H), 7.77 (br. s., 1H), 8.21 (br. s., 1H), 9.01 (br. s., 1H).

Scheme XII: Synthesis of N-(4-(tert-butylthio)-2'-(1H-1,2,4-triazol-5-yl)-[1,1'-biphenyl]-3-yl)-2-(p-tolyl)acetamide

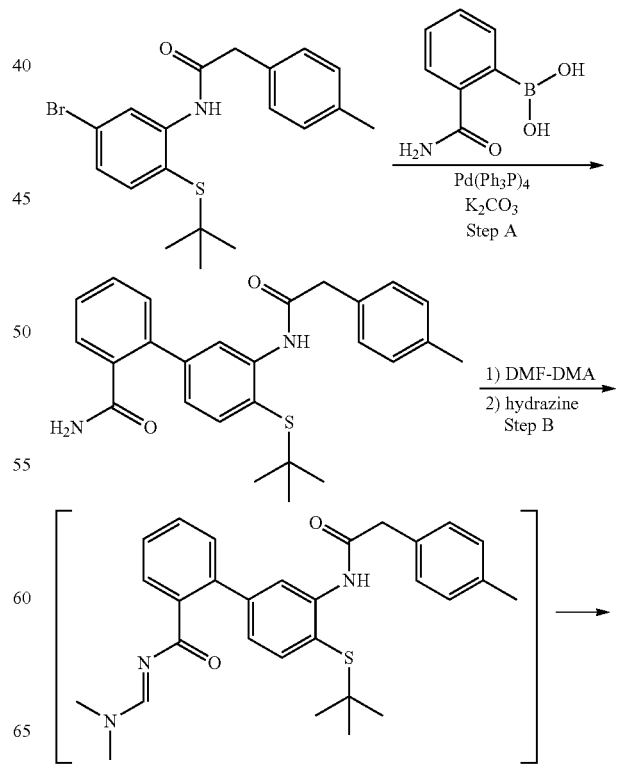

Example 72: N-(4-(tert-butylthio)-2'-(1H-1,2,4-triazol-5-yl)-[1,1'-biphenyl]-3-yl)-2-(p-tolyl)acetamide

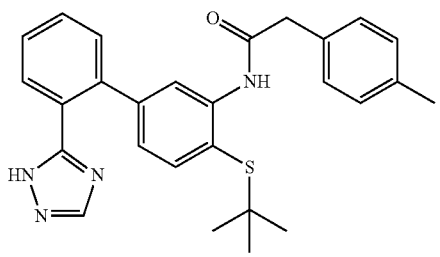

Step A

4'-(tert-Butylthio)-3'-(2-(p-tolyl)acetamido)-[1,1'-biphenyl]-2-carboxamide

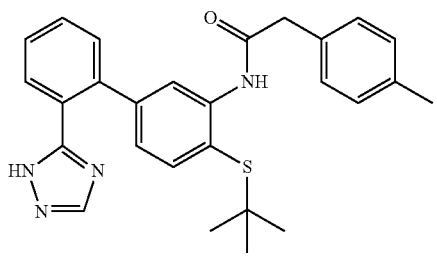 [SMILES: Cc1ccc(CC(=O)Nc2cc(-c3ccccc3-c3ncn[nH]3)ccc2SC(C)(C)C)cc1]

This compound was prepared from N-(5-bromo-2-(tert-butylthio)phenyl)-2-(p-tolyl)acetamide and (2-carbamoylphenyl)boronic acid following the procedure described in Step D (Scheme I). LCMS (M+1)⁺: m/z 433.3. ¹H NMR (400 MHz, DMSO-d₆): δ ppm 1.04 (s, 9H), 2.31 (s, 3H), 3.75 (s, 2H), 7.11 (dd, J=7.91, 1.86 Hz, 1H), 7.20-7.26 (m, 2H), 7.28-7.38 (m, 4H), 7.39-7.55 (m, 4H), 7.71 (s, 1H), 8.41 (d, J=1.76 Hz, 1H), 9.01 (s, 1H).

Step B

N-(4-(tert-butylthio)-2'-(1H-1,2,4-triazol-5-yl)-[1,1'-biphenyl]-3-yl)-2-(p-tolyl)acetamide

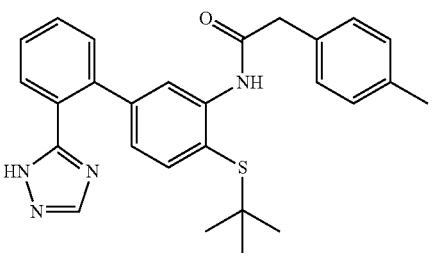 [SMILES: Cc1ccc(CC(=O)Nc2cc(-c3ccccc3-c3ncn[nH]3)ccc2SC(C)(C)C)cc1]

A mixture of 4'-(tert-butylthio)-3'-(2-(p-tolyl)acetamido)-[1,1'-biphenyl]-2-carboxamide (118 mg, 0.273 mmol) and DMF-DMA (2 mL, 14.94 mmol) was heated at 80° C. for 1 h and concentrated to provide (E)-4'-(tert-butylthio)-N-((dimethylamino)methylene)-3'-(2-(p-tolyl)acetamido)-[1,1'-biphenyl]-2-carboxamide (139.5 mg, 0.286 mmol, 105% yield) used as is in the next step. To a portion of this product (69 mg, 0.141 mmol) in Acetic Acid (1 mL) was added hydrazine (6.66 μl, 0.212 mmol) (hydrazine monohydrate, 0.01 mL) and the mixture was stirred at 110° C. for 1.5 h. The mixture was concentrated and purified by HPLC (RP C18, MeCN/water 10-100%, 0.1% formic acid) to provide the title compound (15.3 mg, 0.034 mmol, 23.68% yield). LCMS (M+1)⁺: m/z 457.3. ¹H NMR (400 MHz, DMSO-d₆): δ ppm 0.94-1.07 (m, 9H), 2.31 (s, 3H), 3.71 (s, 2H), 6.76 (d, J=7.62 Hz, 1H), 7.19-7.25 (m, 2H), 7.26-7.34 (m, 3H), 7.38 (d, J=6.64 Hz, 1H), 7.43-7.66 (m, 2H), 7.70-7.89 (m, 1H), 8.14-8.29 (m, 1H), 8.43 (s, 1H), 8.86-9.05 (m, 1H).

Example 73: N-(4-(tert-butylthio)-2'-(1,2,4-oxadiazol-5-yl)-[1,1'-biphenyl]-3-yl)-2-(p-tolyl)acetamide

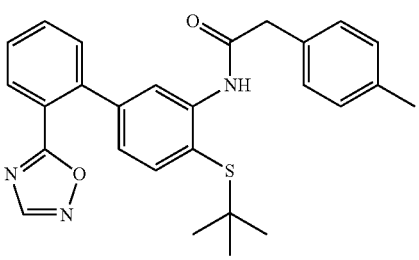 [SMILES: Cc1ccc(CC(=O)Nc2cc(-c3ccccc3-c3ncno3)ccc2SC(C)(C)C)cc1]

To a solution of (E)-4'-(tert-butylthio)-N-((dimethylamino)methylene)-3'-(2-(p-tolyl)acetamido)-[1,1'-biphenyl]-2-carboxamide (69 mg, 0.141 mmol) prepared as described above in 1,4-dioxane (1.000 mL) was added a mixture made by adding hydroxylamine hydrochloride (11.80 mg, 0.170 mmol) to sodium hydroxide (0.031 mL, 0.156 mmol) (5M/water) and acetic acid (0.3 mL) and the mixture was stirred at 90° C. for 4.5 h. The mixture was concentrated, diluted with DMF and purified by HPLC (RP C18, MeCN/water 20-100%, 0.1% formic acid) to provide the title compound (15 mg, 0.033 mmol, 23.17% yield).). LCMS (M+1)⁺: m/z 458.3. ¹H NMR (400 MHz, DMSO-d₆): δ ppm 1.03 (s, 9H), 2.31 (s, 3H), 3.72 (s, 2H), 6.91 (dd, J=7.81, 1.95 Hz, 1H), 7.19-7.25 (m, 2H), 7.26-7.32 (m, 2H), 7.44 (d, J=7.81 Hz, 1H), 7.57 (d, J=7.81 Hz, 1H), 7.63-7.70 (m, 1H), 7.73-7.82 (m, 1H), 8.00 (d, J=7.03 Hz, 1H), 8.22 (d, J=1.56 Hz, 1H), 8.95-9.04 (m, 2H).

Scheme XIII: Synthesis of N-(4-(tert-butylthio)-2'-(1H-tetrazol-5-yl)-[1,1'-biphenyl]-3-yl)-5-chloropyridin-2-amine

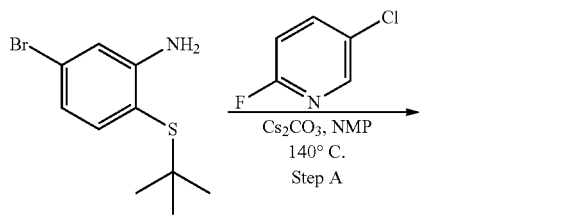

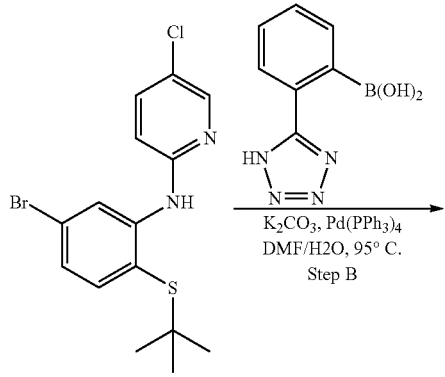

Example 74: N-(4-(tert-Butylthio)-2'-(1H-tetrazol-5-yl)-[1,1'-biphenyl]-3-yl)-5-chloropyridin-2-amine

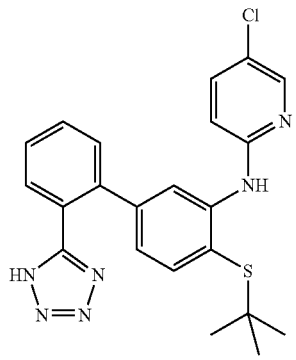 [SMILES: CC(C)(C)Sc1ccc(-c2ccccc2-c2nnn[nH]2)cc1Nc1ccc(Cl)cn1]

Step A

N-(5-bromo-2-(tert-butylthio)phenyl)-5-chloropyridin-2-amine

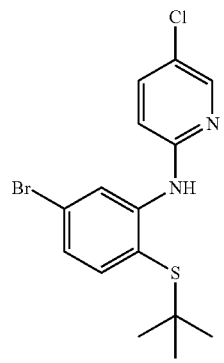 [SMILES: CC(C)(C)Sc1ccc(Br)cc1Nc1ccc(Cl)cn1]

A mixture of 5-bromo-2-(tert-butylthio)aniline (300 mg, 1.2 mmol), 5-chloro-2-fluoropyridine (157 mg, 1.2 mmol), Cs₂CO₃ (782 mg, 2.4 mmol) in NMP (5 mL) was purged with N₂ before heated to 140° C. for 8 h. The reaction mixture was then cooled down to room temperature. Water was added and the mixture was partitioned between EtOAc (50 mL) and water (15 mL). The layers were separated and the organic layer was washed with brine (20 mL), dried with Na₂SO₄, and concentrated. The crude product was purified by flash chromatography (silica gel, 5-20% EtOAc in petroleum ether) to give the title compound (100 mg, 24%) as a yellow solid. LCMS (M+H)⁺: m/z=371.43.

Step B

N-(4-(tert-butylthio)-2'-(1H-tetrazol-5-yl)-[1,1'-biphenyl]-3-yl)-5-chloropyridin-2-amine

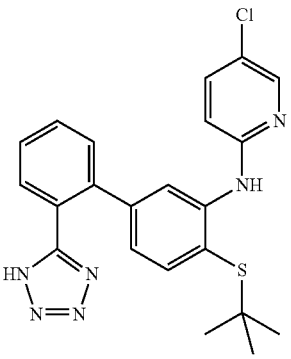 [SMILES: CC(C)(C)Sc1ccc(-c2ccccc2-c2nnn[nH]2)cc1Nc1ccc(Cl)cn1]

A mixture of N-(5-bromo-2-(tert-butylthio)phenyl)-5-chloropyridin-2-amine (100 mg, 0.27 mmol), (2-(1H-tetrazol-5-yl)phenyl)boronic acid (51 mg, 0.27 mmol), Pd(PPh₃)₄ (32 mg, 0.027 mmol), K₂CO₃ (112 mg, 0.81 mmol) in DMF/H₂O (2.5 mL/0.5 mL) was purged with N₂ before heated to 95° C. overnight. The reaction mixture was then cooled down to room temperature and filtered off the solid. The filtrate was concentrated and partitioned between EtOAc (15 mL) and water (10 mL). The layers were separated and the organic layer was washed with brine (15 mL), dried with Na$_2$SO$_4$, and concentrated. The residue was purified by preparative HPLC (RP C18 column, 40-100% acetonitrile in water, 0.1% formic acid) to give the titled compound (30 mg, 26%) as a white solid. LCMS (M+H)$^+$: m/z=437.22. $^1$H NMR (400 MHz, CDCl$_3$): δ 15.35 (s, 1H), 8.22-8.14 (m, 2H), 8.07 (d, J=1.9 Hz, 1H), 7.93 (s, 1H), 7.59 (ddd, J=14.3, 7.4, 4.3 Hz, 4H), 7.47-7.42 (m, 1H), 6.85 (dd, J=7.8, 1.9 Hz, 1H), 6.81 (d, J=8.8 Hz, 1H), 1.28 (s, 9H).

Scheme XIV: Synthesis of 6-((4-(tert-butylthio)-2'-(1H-tetrazol-5-yl)-[1,1'-biphenyl]-3-yl)amino)nicotinonitrile

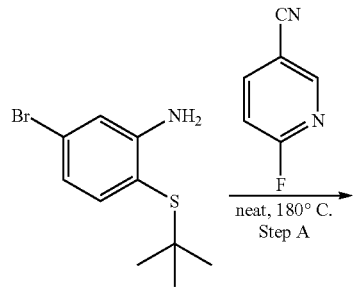

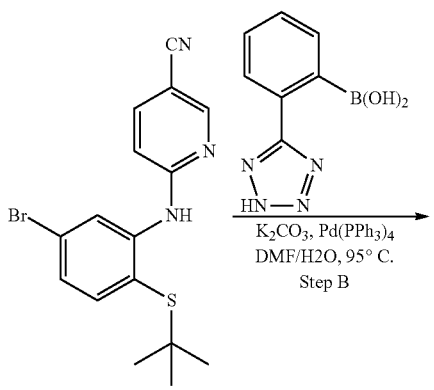

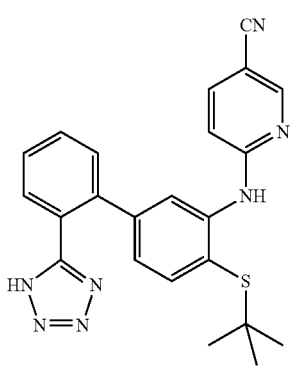

Example 75: 6-((4-(tert-Butylthio)-2'-(1H-tetrazol-5-yl)-[1,1'-biphenyl]-3-yl)amino)nicotinonitrile

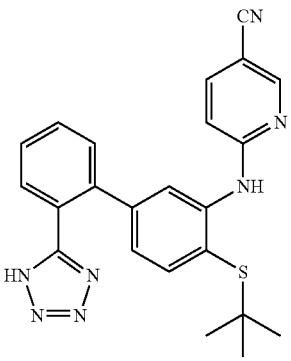 [SMILES: CC(C)(C)Sc1ccc(-c2ccccc2-c2nnn[nH]2)cc1Nc1ccc(C#N)cn1]

Step A 6-((5-bromo-2-(tert-butylthio)phenyl)amino)nicotinonitrile

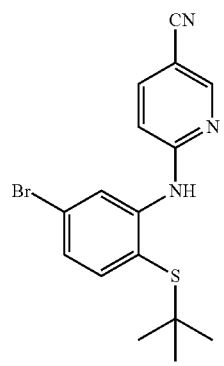 [SMILES: CC(C)(C)Sc1ccc(Br)cc1Nc1ccc(C#N)cn1]

A mixture of 5-bromo-2-(tert-butylthio)aniline (300 mg, 1.2 mmol) and 6-fluoronicotinonitrile (440 mg, 3.6 mmol) was place in a microwave vial and stirred at 180° C. under neat condition for 5 h before cooled down to room temperature. EtOAc and water were added and the organic layer was washed with brine, dried over Na$_2$SO$_4$, concentrated under vacuum and purified on silica gel (5-60% EtOAc in petroleum ether) to get the title compound (260 mg, 62% yield) as a yellow solid. LCMS (M+H)$^+$: m/z=362.09.

Step B 6-((4-(tert-butylthio)-2'-(1H-tetrazol-5-yl)-[1,1'-biphenyl]-3-yl)amino)nicotinonitrile

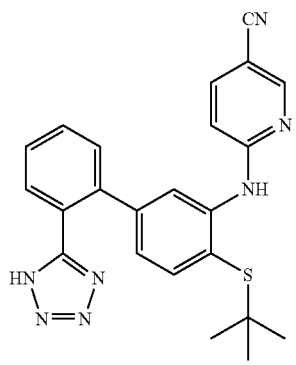 [SMILES: CC(C)(C)Sc1ccc(-c2ccccc2-c2nnn[nH]2)cc1Nc1ccc(C#N)cn1]

A mixture of 6-((5-bromo-2-(tert-butylthio)phenyl)amino)nicotinonitrile (130 mg, 0.36 mmol), (2-(1H-tetrazol-5-yl)phenyl)boronic acid (68 mg, 0.36 mmol), Pd(PPh$_3$)$_4$ (42 mg, 0.036 mmol), K$_2$CO$_3$ (149 mg, 1.08 mmol) in DMF/H$_2$O (2.5 mL/0.5 mL) was purged with N$_2$ before heated to 95° C. overnight. The reaction mixture was then cooled down to room temperature and filtered off the solid. The filtrate was concentrated and partitioned between EtOAc (15 mL) and water (10 mL). The layers were separated and the organic layer was washed with brine (15 mL), dried with Na$_2$SO$_4$, and concentrated. The residue was purified by preparative HPLC (RP C18 column, 40-100% acetonitrile in water, 0.1% formic acid) to give the titled compound (39 mg, 25%) as a white solid. LCMS (M+H)$^+$: m/z=428.35. $^1$H NMR (400 MHz, CDCl$_3$): δ 8.53 (d, J=2.0 Hz, 1H), 8.27-8.19 (m, 2H), 8.15 (d, J=1.9 Hz, 1H), 7.80 (dd, J=8.7, 2.2 Hz, 1H), 7.66-7.57 (m, 3H), 7.48-7.44 (m, 1H), 6.96 (dd, J=7.9, 1.9 Hz, 1H), 6.86 (d, J=8.7 Hz, 1H), 1.29 (s, 9H).

Example 76: N-(4-(tert-butylthio)-2'-(1H-tetrazol-5-yl)-[1,1'-biphenyl]-3-yl)-5-(trifluoromethyl)pyridin-2-amine

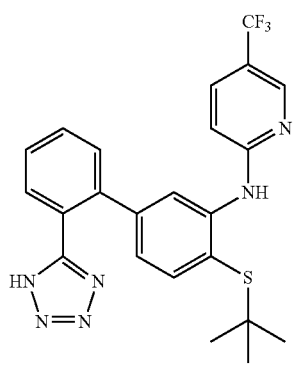 [SMILES: CC(C)(C)Sc1ccc(-c2ccccc2-c2nnn[nH]2)cc1Nc1ccc(C(F)(F)F)cn1]

This compound was prepared following Steps A and B (Scheme XIV) to provide the title compound. LCMS (M+H)$^+$: m/z=471.26. $^1$H NMR (400 MHz, DMSO): δ 8.80 (s, 1H), 8.42 (s, 1H), 7.95 (d, J=1.7 Hz, 1H), 7.86 (dd, J=8.9, 2.5 Hz, 1H), 7.73-7.67 (m, 2H), 7.65-7.58 (m, 2H), 7.50 (d, J=7.9 Hz, 1H), 7.13 (d, J=8.9 Hz, 1H), 6.90 (dd, J=7.9, 2.0 Hz, 1H).

Compound Data

Human indoleamine 2,3-dioxgenase (IDO) cellular data is presented below. Brief descriptions of the cellular assays are provided following the table.

| Example | HeLa pIC$_{50}$ | PBMC pIC$_{50}$ |
| --- | --- | --- |
| 1 | 7.8 | 7.9 |
| 4 | 6.5 | 6.1 |
| 5 | <5 | |
| 6 | 5.2 | |
| 7 | 5.3 | |
| 8 | 5.2 | |
| 9 | <5 | |
| 10 | 6.6 | 6.9 |
| 11 | 6 | |
| 12 | 5.3 | |
| 13 | 6.4 | 7.1 |
| 14 | 5.5 | 5.8 |
| 15 | 5.7 | 5.7 |
| 16 | 6.6 | |
| 17 | 5.6 | |
| 18 | 5.4 | |
| 19 | 7.8 | 8 |
| 20 | 7.6 | 7.7 |
| 21 | 7.7 | |
| 22 | 7.5 | |
| 23 | 7.2 | |
| 24 | 6.4 | |
| 25 | 6.4 | |
| 26 | 6.1 | |
| 27 | 8.4 | 8.5 |
| 29 | 5.3 | |
| 30 | <5 | |
| 31 | <5 | |
| 32 | <5 | |
| 33 | 5.1 | |
| 34 | 7.1 | 7.6 |
| 35 | <5.5 | 5.8 |
| 36 | 5.6 | 5.9 |
| 37 | 6.1 | 6.6 |
| 38 | 7 | |
| 39 | 8.6 | 8.8 |
| 40 | 7.5 | 7.7 |
| 42 | 6.9 | |
| 43 | 7.3 | 7.9 |
| 44 | 5.5 | 5.4 |
| 45 | 5.6 | |
| 46 | 5.2 | 5.3 |
| 47 | 6.3 | 6.3 |
| 48 | 5.5 | |
| 49 | 6 | |
| 50 | 6.9 | |
| 51 | 7.8 | 7.2 |
| 52 | 7.6 | 6.8 |
| 55 | 7.5 | 7.3 |
| 56 | 7.5 | 7.7 |
| 57 | 7.6 | |
| 58 | 7.4 | |
| 59 | 6.4 | |
| 60 | 7.2 | |
| 61 | 6.2 | |
| 62 | 6.3 | |
| 64 | 7.2 | 7.3 |
| 65 | 7.4 | 7.6 |
| 66 | 8 | 8.1 |
| 67 | 7 | 7.9 |

HeLa IDOi Assay:

Compounds of the present invention were tested via high-throughput cellular assays utilizing detection of kynurenine via mass spectrometry and cytotoxicity as endpoints. For the mass spectrometry and cytotoxicity assays, human epithelial HeLa cells (CCL-2; ATCC®, Manassas, Va.) were stimulated with human interferon-γ (IFN-γ) (Sigma-Aldrich Corporation, St. Louis, Mo.) to induce the expression of indoleamine 2,3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (−IFN-γ) HeLa cells for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ) HeLa cells for both the mass spectrometry and cytotoxicity assays.

Frozen stocks of HeLa cells were washed and recovered in DMEM high glucose medium with HEPES (Thermo Fisher Scientific, Inc., Waltham, Mass.) supplemented with 10% v/v certified fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 100,000 cells/mL in the supplemented DMEM medium. 50 µL of either the cell suspension, for the mass spectrometry assay, or medium alone, for the cytotoxicity assay, were added to the low control wells, on the previously prepared 384-well compound plates, resulting in 5,000 cells/well or 0 cells/well respectively. IFN-γ was added to the remaining cell suspension at a final concentration of 10 nM, and 50 µL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 10 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 µM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 µL from each well of the acetonitrile extraction plates were added to 90 µL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as IDO1 inhibition versus compound concentration following normalization using the formula 100−(100*((U−C2)/(C1−C2))), where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula 100−(100*((U−C2)/(C1−C2))), where U was the unknown value, C1 was the average of the high (0% cytotoxicity) control wells and C2 was the average of the low (100% cytotoxicity) control wells.

Curve fitting was performed with the equation $y=A+((B-A)/(1+(10^x/10^C)^D))$, where A was the minimum response, B was the maximum response, C was the $\log(XC_{50})$ and D was the Hill slope. The results for each test compound were recorded as pIC50 values for the mass spectrometry assay and as pCC50 values for the cytoxicity assay (−C in the above equation).

PBMC IDOi Assay:

Compounds of the present invention were tested via high-throughput cellular assays utilizing detection of kynurenine via mass spectrometry and cytotoxicity as endpoints. For the mass spectrometry and cytotoxicity assays, human peripheral blood mononuclear cells (PBMC) (PB003F; AllCells®, Alameda, Calif.) were stimulated with human interferon-γ (IFN-γ) (Sigma-Aldrich Corporation, St. Louis, Mo.) and lipopolysaccharide from *Salmonella minnesota* (LPS) (Invivogen, San Diego, Calif.) to induce the expression of indoleamine 2,3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (−IFN-γ/−LPS) PBMCs for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ/+LPS) PBMCs for both the mass spectrometry and cytotoxicity assays.

Frozen stocks of PBMCs were washed and recovered in RPMI 1640 medium (Thermo Fisher Scientific, Inc., Waltham, Mass.) supplemented with 10% v/v heat-inactivated fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 1,000,000 cells/mL in the supplemented RPMI 1640 medium. 50 µL of either the cell suspension, for the mass spectrometry assay, or medium alone, for the cytotoxicity assay, were added to the low control wells, on the previously prepared 384-well compound plates, resulting in 50,000 cells/well or 0 cells/well respectively. IFN-γ and LPS were added to the remaining cell suspension at final concentrations of 100 ng/ml and 50 ng/ml respectively, and 50 µL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 40 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 µM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 µL from each well of the acetonitrile extraction plates were added to 90 µL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula 100−(100*((U−C2)/(C1−C2))), where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula 100−(100*((U−C2)/(C1−C2))), where U was the unknown value, C1 was the average of the high (0% cytotoxicity) control wells and C2 was the average of the low (100% cytotoxicity) control wells.

Curve fitting was performed with the equation $y=A+((B-A)/(1+(10^V/10^C)^D))$, where A was the minimum response, B was the maximum response, C was the $\log(XC_{50})$ and D was the Hill slope. The results for each test compound were recorded as pIC50 values for the mass spectrometry assay and as pCC50 values for the cytoxicity assay (−C in the above equation).

What is claimed is:

1. A compound of Formula II

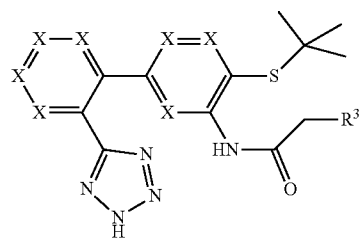

Formula II or a pharmaceutically acceptable salt thereof, wherein
  in each depicted ring containing Xs, either each X is CH to form a benzene ring, or one X is N while the others are CH to form a pyridine ring;
  the depicted tetrazole may optionally be substituted by a $CH_2OH$, wherein said $CH_2OH$ is optionally converted into a prodrug by converting the $CH_2OH$ group to a $CH_2OC(O)CH_3$, $CH_2OC(O)C(C_{1-4}alkyl)_3$, or $OP(O)(OH)_2$ group, or $OP(O)(OC_{1-4}alkyl)_2$ group;
  $R^3$ is phenyl, or a 4 to 6-membered heterocycle or heteroaryl containing 1 to 4 heteroatoms selected from N, S, and O; and wherein said phenyl, heterocycle, or heteroaryl, may optionally substituted by one to three $C_{1-3}$alkyl groups each of which is optionally substituted by 1-3 halogens.

2. A pharmaceutical composition comprising a compound or salt according to claim 1.

* * * * *